(12) United States Patent
Kawasaki et al.

(10) Patent No.: US 6,635,438 B2
(45) Date of Patent: *Oct. 21, 2003

(54) ENZYMATIC CYCLING ASSAYS FOR HOMOCYSTEINE AND CYSTATHIONINE

(75) Inventors: Glenn Kawasaki, Seattle, WA (US); Heather Kay Webb, San Francisco, CA (US); Jeffrey Owens, Seattle, WA (US); Doreen Forest, Kelso, WA (US); Raymond Liedtke, Bellevue, WA (US); Sobomabo Lawson, Shoreline, WA (US); Mark Legaz, Longview, WA (US)

(73) Assignee: Catch, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/012,762

(22) Filed: Nov. 6, 2001

(65) Prior Publication Data

US 2003/0138872 A1 Jul. 24, 2003

Related U.S. Application Data

(63) Continuation-in-part of application No. 09/704,306, filed on Nov. 1, 2000.
(60) Provisional application No. 60/203,349, filed on May 10, 2000, and provisional application No. 60/163,126, filed on Nov. 2, 1999.

(51) Int. Cl.[7] ............................. C12Q 1/26; C12Q 1/00; C12Q 1/48; C12Q 1/34
(52) U.S. Cl. .................. 435/25; 435/4; 435/975; 435/968; 435/15; 435/18; 530/300

(58) Field of Search .................. 435/25, 4, 975, 435/968, 15, 18; 530/300

(56) References Cited

U.S. PATENT DOCUMENTS 6,174,696 B1 * 1/2001 Seman ........................... 435/4

FOREIGN PATENT DOCUMENTS

WO    WO 01/33187 A2 * 10/2001

* cited by examiner

*Primary Examiner*—Louise N. Leary
(74) *Attorney, Agent, or Firm*—Hovey Williams LLP

(57) ABSTRACT

The present invention provides an enzymatic cycling assay for assessing the amount of homocysteine and/or cystathionine in a solution such as blood, blood derivatives, or urine. The assay comprises the steps of contacting the solution containing homocysteine and/or cystathionine to form a reaction mixture, with CBS, or a derivative thereof, L-serine, and CBL, or a derivative thereof, for a time period sufficient to catalyze the cyclical conversion of homocysteine form to cystathionine and the reconversion of cystathionine to homocysteine with the production of pyruvate and ammonia; determining the amount of homocysteine and/or ammonia present in the reaction mixture; and determining the amount of homocysteine and/or cystathionine present in the solution based on the amount of pyruvate and/or ammonia formed. Expression vectors and isolation procedures for CBS, or derivatives thereof, and CBL, or derivatives thereof, are also provided as well as test kits for carrying out the assay. In preferred embodiments, the assays can be conducted in 15 minutes or less, with a minimum of enzyme usage.

142 Claims, 9 Drawing Sheets

ENZYMATIC CYCLING ASSAYS FOR HOMOCYSTEINE AND CYSTATHIONINE

RELATED APPLICATIONS

This application is a continuation-in-part application of U.S. patent application Ser. No. 09/704,036, filed Nov. 1, 2000 now pending, which claimed benefit from Provisional Patent Applications Ser. No. 60/163,126, filed Nov. 2, 1999 and Ser. No. 60/203,349 filed May 10, 2000, and the content and teachings of each of these previous applications is incorporated herein by reference.

SEQUENCE LISTING

A Sequence Listing containing 21 sequences in the form of a computer readable ASCII file in connection with the present invention is incorporated herein by reference and appended hereto as two (2) original compact disks in accordance with 37 CFR 1.821(c), an identical copy thereof in accordance with 37 CFR 1.821(e), and one (1) identical copy thereof in accordance with 37 CFR 1.52(e).

BACKGROUND OF THE INVENTION

High levels of homocysteine in human plasma are correlated with increased risks for coronary heart disease, stroke, arteriosclerosis, and other diseases. As a result, it is desirable to screen the general population for elevated amounts of this amino acid. To make wide-scale testing for homocysteine feasible, new and less expensive assays need to be developed.

Plasma homocysteine is routinely measured by high-pressure liquid chromatography (HPLC) and gas chromatography/mass spectrometry (GC/MS) at a cost of over $100 per assay, making these physical separation methods too costly for a population-wide study. For example, urine or blood samples can be prepared for amino acid chromatography, and L-homocysteine measured by HPLC separation and detection. Fiskerstrand et al. (*Clin. Chem.*, 39:263–271 (1993)) describe a method of assaying L-homocysteine using fluorescent labeling of serum thiols, followed by HPLC separation and detection of the L-homocysteine derivative from the various other sulfur-containing compounds. However, such methods are typically time consuming, costly, and not readily available to many laboratories.

Indirect immunoassays for homocysteine have also been developed, however, these antibody methods are still relatively expensive at about $24 per test. One particular indirect immunoassay enzymatically converts homocysteine to adenosyl homocysteine and the amount of adenosyl homocysteine is determined by a competitive ELISA (enzyme linked immunoassay), using an anti-adenosyl homocysteine antibody (for example, see U.S. Pat. No. 5,827,645, the content of which is incorporated herein by reference).

Indirect enzyme assays have been developed for the quantitation of L-homocysteine. For example, the enzyme S-adenosyl-homocysteine hydrolase and adenosine are added to a test sample. The resulting concentration, or change in the concentration, of adenosine in the reaction mixture is used as an indicator for the initial concentration of homocysteine in the sample.

Direct enzyme assays have also been reported for measuring homocysteine. Typically, these protocols irreversibly convert homocysteine to other compounds that are quantifiable. For example, the enzyme homocysteine dehydratase has been used to remove the sulfhydryl group from homocysteine. The concentration of the removed sulfhydryl moiety is then measured. A major drawback with this and other enzyme assays for homocysteine is that the enzymes employed react with other sulfur containing amino acids and compounds related to homocysteine, leading to a high and inconsistent background and measurements of homocysteine from plasma that are inaccurate.

Enzymatic (or enzymic) cycling assays have been reported for a very small number of analytes. In an enzymatic cycling assay two or more enzymes activities are used which recycle substrate and do not irreversibly convert the measured compound. Instead the "compound" is used catalytically to control the rate of conversion to the quantitated compound in the assay. As a result, the analyte of interest remains in a steady-state concentration which is low enough to create a pseudo-first order rate of reaction. The steady-state concentration of the analyte is thereby linearly related to the rate of the overall assay. By measuring reaction rates, the amount of the analyte is easily determined. Enzymatic cycling assays are sometime called "amplification" assays, because the methods typically increase the sensitivity of measurement for an analyte by 100- to 1000-fold. The amplification in measurement is a direct result of not reducing the steady-state concentration of the compound. No enzymatic cycling assay has been reported for measuring homocysteine.

The present invention provides an enzymatic cycling assay for homocysteine and/or cystathionine which is less expensive, and provides a higher sample throughput than the diagnostic assays currently available. Further, the invention provides methods and vectors for the recombinant production of enzymes which can be used in the production of assay reagents and test kits for assessing the amount of homocysteine and cystathionine in a sample.

SUMMARY OF THE INVENTION

The present invention provides an enzymatic cycling assay method for assessing the amount of homocysteine and/or cystathionine in a solution. The assay takes advantage of the reaction of homocysteine and L-serine to form cystathionine by the enzyme cystathionine β-synthase (CBS), or a derivative thereof, and the enzymatic conversion by cystathionine β-lyase (CBL) of cystathionine to homocysteine, pyruvate and ammonia. The assay provides a steady-state concentration of the homocysteine and/or cystathionine which is linearly related to the rate of the overall reaction. The amount of homocysteine and/or cystathionine determined in a sample is based on the amount of pyruvate and/or ammonia which is formed or the amount of serine removed from the reaction mixture. Solutions which can be tested using the assay of the present invention can include laboratory samples of blood, serum, plasma, urine, and other biological samples. Additionally, any other liquid sample can be tested.

In one embodiment, the present invention provides a method for assessing the amount of homocysteine and/or cystathionine in a solution comprising the step of:

(a) contacting the solution containing homocysteine and/or cystathionine (either before and/or after performing a disulfide reduction step) to form a reaction mixture, with CBS, or a derivative thereof, L-serine and CBL, or a derivative thereof, for a time period sufficient to catalyze the cyclical conversion of homocysteine to cystathionine, and the reconversion of cystathionine to homocysteine with the production of pyruvate and ammonia;

(b) determining the amount of pyruvate and/or ammonia present in the reaction mixture; and (c) assessing the amount of homocysteine and/or cystathionine present in the solution based on the amount of pyruvate and/or ammonia formed.

More particularly, the method provides for the assessment of the amount of homocysteine by the addition of the inexpensive amino acid L-serine. The amount of pyruvate present in the reaction mixture can be measured in a number of ways. In one particular embodiment of the present invention lactate dehydrogenase (LDH), or a derivative thereof, and NADH (reduced nicotinamide cofactor), or a derivative thereof, are present in the reaction mixture. LDH in the presence of NADH converts pyruvate to lactate with the oxidation of NADH to NAD+ (oxidized nicotinamide cofactor).

The oxidation of NADH to NAD+ can be measured by a number of methods known in the art including monitoring the reaction mixture at 340 nm. Production of NAD+ can also be monitored by the oxidation of a dye to produce an observable color change. Dyes preferred for use in the present invention include, but are not limited to, 5,5'-dithiobis(2-nitrobenzoic acid), 2,6-dichlorophenylindophenol, tetrazolium compounds, phenazine methosulfate, methyl viologen, or derivatives of any of these dyes. The amount of homocysteine and/or cystathionine present in the solution is based on the intensity of the observed color compared to a standard curve constructed for samples of known concentration of the analyte.

In an alternative embodiment pyruvate oxidase, with horseradish peroxidase, in the presence of hydrogen peroxide and a chromogen are used to detect the amount of pyruvate present in the sample. Sodium N-ethyl-N-2-hydroxy 3-sulfopropyl)m-toluidine (TOOS) and other N-ethyl-N-(2-hydroxy-3-sulfopropyl)-aniline derivatives are preferred chromogens for this calorimetric reaction. As above, the amount of homocysteine and/or cystathionine present in the sample is based on the intensity of the observed color compared to a standard curve constructed for samples of known concentrations of the analyte.

The amount of homocysteine and/or cystathionine present in a solution can also be measured based on the amount of ammonia present in the reaction mixture. Methods for determining the concentration of ammonia in a solution are legion. In one particular embodiment of the present invention, the amount of ammonia is measured using a commonly available standard ammonia sensor.

In another embodiment, the present invention is directed to a method for assessing the amount of homocysteine and/or cystathionine in a sample comprising the steps of contacting the solution with a reducing agent for a time period sufficient to reduce substantially all homocysteine and other disulfides that are present in the solution to homocysteine. Treatment with a reducing agent can also act to release homocysteine which is attached to a protein and/or other molecules present in a solution through a disulfide bond. After reduction the solution is then contacted with CBS, or a derivative thereof, L-serine, and CBL, or a derivative thereof, for a time period sufficient to catalyze the cyclical conversion of homocysteine to cystathionine and the conversion of cystathionine to homocysteine with the production of pyruvate and ammonia. To assess the amount of homocysteine and/or cystathionine present in the solution the amount of pyruvate and/or ammonia present in the reaction mixture can be determined as set forth above. Preferred reducing agents for use in the present invention include borohydride salts and thiol reducing agents. Typical thiol reducing agents appropriate for use in the present embodiment include dithioerythritol (DTE), dithiothreitol (DTT), β-mercaptoethanol (βME), tris-(carboxyethyl) phosphine hydrochloride (TCEP), or thioacetic acid, or any derivatives thereof, and the like.

In yet another embodiment for assessing the amount of homocysteine and/or cystathionine present in a solution, the solution can be pretreated with cystathionine γ-lyase (CGL), or a derivative thereof, for a time period sufficient to remove any cystathionine from the reaction mixture by the conversion of cystathionine to α-ketoglutarate. Following cystathionine removal the cystathionine γ-lyase is removed from the reaction mixture or destroyed. In a typical embodiment, the cystathionine γ-lyase is destroyed by heating the solution for a time period sufficient to remove substantially its enzymatic activity. The cystathionine γ-lyase can also be immobilized on an insoluble substrate or surface, such as, for example, a micro particle or bead, which can be easily removed.

In still another embodiment of the present invention a method is provided for assessing the amount of homocysteine and/or cystathionine present in a solution comprising the reaction of the solution with L-serine and CBS, or a derivative thereof, and CBL, or a derivative thereof, which have been immobilized on a solid surface. The solid surface can be, for example, paper, filter paper, nylon, glass, ceramic, silica, alumina, diatomaceous earth, cellulose, polymethacrylate, polypropylene, polystyrene, polyethylene, polyvinylchloride, and derivatives thereof. The solid surface can be the sides and bottom of the test container or can be a material added to the test container. In a preferred embodiment the solid surface comprises a bead which is added to the test container.

The CBS, or derivative thereof, CBL, or derivative thereof, and cystathionine γ-lyase, or derivative thereof, useful in the present invention can be obtained as a crude extract from a cell. In one embodiment of the present invention the cystathionine β-synthase (CBS), or derivative thereof, cystathionine β-lyase CBL, and/or cystathionine γ-lyase (CGL) are purified from human, yeast or bacterial cells. In a particularly preferred embodiment of the present invention the genes which encode the enzymes are isolated or synthesized and are expressed as a recombinant protein in a host cell. It is particularly preferred that a DNA sequence which encodes an affinity tag be added to the gene construct to aid in the purification and/or detection of the recombinantly produced enzymes. Recombinant methods can also be used to provide fusion proteins which comprise the enzyme activities of CBS and CBL in a single protein. An affinity tag can also be included as part of the fusion protein construct to aid in the purification of the fusion protein.

The present invention also provides as a method for assessing the amount of homocysteine in a sample an assay format which correlates the amount of homocysteine/transcription factor complex which is bound to a consensus polynucleotide binding sequence. In a particular embodiment the method comprises contacting the sample with a reducing agent for a time period sufficient to release homocysteine from any associated protein; contacting the reduced homocysteine with a homocysteine metabolite binding transcription factor under conditions conducive for complex formation, admixing the sample with a consensus polynucleotide sequence specifically recognized by the homocysteine/transcription factor complex; and assessing from the amount of homocysteine/transcription factor complex bound to the consensus polynucleotide sequence the amount of homocysteine present in the sample. Reducing agents which are applicable for use in the method comprise borohydride salt or thiol reducing agents including dithio-erythritol (DTE), dithiothreitol (DTT), β-mercaptoethanol, tris-(carboxyethyl)phosphine (TCEP), or thioacetic acid, or any salt of each. Homocysteine metabolite binding transcription factors include MetR of *E. coli* which recognizes a consensus polynucleotide sequence, for example, the polynucleotide sequence as depicted in SEQ ID NO: 11 (Marconi et al., *Biochem. Biophys. Res. Commun.*, 175:1057–1063 (1991)) or a derivative thereof.

Yet another embodiment of the present invention provides a test kit comprising a container for holding the solution to be assessed for the amount of homocysteine and/or cystathionine, L-serine, CBS, or a derivative thereof, CBL, or a derivative thereof, and any buffers, auxiliary substances and solvents required to provide conditions conducive to high enzyme activity. The test kit can further comprise lactate dehydrogenase, or a derivative thereof, and NADH, or a derivative thereof. NADH can be measured directly at 340 nm or, a dye capable of providing a color change when oxidized can be included. The quantity of homocysteine and/or cystathionine is correlated with the change in absorbance measure over time.

In a preferred embodiment the enzymes are provided immobilized to a solid support. The solid support can comprise the surface of the container provided to hold the test sample or can be a bead or other article added to the container. In an additional embodiment of the present invention, cystathionine γ-lyase can be provided as part of the test kit to remove any cystathionine from the test solution prior to the enzymatic cycling assay. Substantially all of the activity of the cystathionine γ-lyase, or derivative thereof, must be removed from or destroyed in the reaction mixture prior to the addition of the remaining components for the enzymatic cycling of homocysteine.

It has been found that the preferred assay of the invention can be carried out in a relatively short period of time and with relatively small amounts of enzyme, giving an assay which has substantial commercial advantages. For example, the preferred assay involves creation of a reaction mixture including a homocysteine-containing sample, serine, CBS, CBL, lactate dehydrogenase, NADH and a reductant such as DTE or DTT, with the CBS/CBL ratio in the mixture being from about 1:1 to 25:1, more preferably from about 1:10, and most preferably from about 2:1 to 5:1. Advantageously, it has been found that the reductant can be present along with the detection system (i.e., the lactate dehydrogenase and NADH) without deleteriously affecting the assay. Accordingly, the assay of the invention can be carried out without a separate reduction step so that total assay times are reduced. Thus, where a plurality of samples are to be assayed by sequentially creating a reaction mixture in a container (e.g., a spectrophotometric cuvette) made up of a sample, serine, CBS, CBL, lactate dehydrogenase, NADH and the reductant, and assessing the amount of pyruvate present in the reaction mixture by monitoring the production of NAD+ over time, the time interval between the respective reaction-creation steps maybe as short as 10–50 seconds with the total reaction time being up to about 20 minutes for a given sample. More preferably, the total reaction time for a given sample is up to about 15 minutes, and still more preferably up to about 13 minutes. The total number of samples assayed per hour may be about 15–30 for slower instruments, but as high as 200–400 for faster instruments. In this preferred assay, a first reaction mixture comprising the sample, serine, lactate dehydrogenase, NADH and the reductant is prepared, with a suitable incubation period to permit liberation of a preponderance (and preferably essentially all) of the homocysteine (total homocysteine) present in the bound, oxidized and/or free states in the sample. Thereafter, CBS and CBL are added to complete the reaction mixture and initiate enzymatic cycling of homocysteine and/or cystathionine.

In another preferred embodiment, cystathionine can be used to make a calibrator(s) for the enzyme assay (since the enzymatic cycling assay interconverts homocysteine and cystathionine). In other words, varying known levels of cystathionine can be used in the assay system to "calibrate" or "standardize" the assay and/or instrument which allows for quantitation of sample results. In this embodiment, a known concentration of cystathionine is added to a biological sample and then subjected to the assay used for one of the other embodiments. The results will be used to establish a calibration line which will then be used to set the homocysteine line, due to the high degree of correlation between the two lines. Alternatively, known levels of cystathionine can be used as a quality control measure, to insure that the assay is working properly. In this quality control embodiment, these "known" levels of cystathionine are assayed as if they were unknown samples, and the results are compared to their known (expected) values, in order to insure that the assay system is functioning properly.

The preferred assays are carried out using isolated (purified) CBL and CBS enzymes having at least about 80% (and preferably at least about 90%) sequence identity with the enzymes selected from the group consisting of SEQ ID Nos. 19 and 20. As used herein, "sequence identity" as it is known in the art refers to a relationship between two or more protein or polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48:1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., *Nucleic Acids Research,* 12(1):387 (1984)), BLASTP, BLASTN and FASTA (Altschul, S. F. et al., *J. Molec. Biol.,* 215:403–410 (1990). The BLASTX program is publicly available from NCBI and other sources (BLAST Manual, Altschul, S. et al., NCVI NLM NIH Bethesda, Md. 20894, Altschul, S. F. et al., *J. Molec. Biol.,* 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Reagents useful in the present invention include CBS, CBL, L-serine, LDH, NADH, DTE, βME, DTT, TCEP, thioacetic acid, and CGL. Concentrations of CBS enzyme useful in the present invention range from about 0.1 to about 100 KU/l. More preferably, the CBS concentration is from about 0.5 to about 75 KU/l, and still more preferably from about 1 to about 50 KU/l. Most preferably, the concentration of CBS is from about 1 to about 30 KU/l. Concentrations of CBL enzyme useful in the present invention range from about 0.01 to about 100 KU/l. More preferably, CBS concentration is from about 0.05 to about 50 KU/l, and still more preferably, from about 0.1 to about 30 KU/l. Most preferably, the CBS concentration is from about 0.1 to about 15 KU/l. L-serine may be present at a final concentration of from about 1 $\mu$M to about 50 mM. More preferably, the L-serine is added at a final concentration of from about 10 $\mu$M to about 40 mM, and still more preferably at a final concentration of from about 100 $\mu$M to about 20 mM. Most preferably, the final concentration of L-serine added is from about 0.2 mM to about 10 mM. When used in any embodiment, LDH is present in the reaction mixture at a final concentration of from about 30 to about 5000 U/L. More preferably, the final concentration of the LDH present in the reaction mixture is from about 30 to about 3000 U/L, and still more preferably from about 50 to about 2500 U/L. Most preferably, LDH is present in the reaction mixture at a final concentration of from about 100 to about 2000 U/L. Additionally, when NADH is used in any embodiment, the amount of NADH present in the reaction mixture can vary between about 0.1 mM to about 2 mM. More preferably, NADH is present in the reaction mixture at a final concentration of from about 0.1 mM to about 1.5 mM, and still more preferably between about 0.1 to about 1 mM. Most preferably, NADH is present in the reaction mixture at a final concentration of from about 0.2 to about 0.8 mM. When DTE is used in the present invention, it can range in final concentration from about 0.01 mM to about 100 mM. More preferably, concentrations of DTE will range from about 0.01 mM to about 50 mM, and still more preferably from about 0.1 mM to about 25 mM. Most preferably, final concentrations of DTE will range from about 0.1 mM to about 10 mM. Similarly, when DTT is used in the present invention, it can range in final concentration from about 0.01 mM to about 100 mM. More preferably, concentrations of DTT will range from about 0.01 mM to about 50 mM, and still more preferably from about 0.1 mM to about 25 mM. Most preferably, final concentrations of DTT will range from about 0.1 mM to about 10 mM. Finally, when CGL is used in the present invention, it can range in final concentration from about 0.1 KU/l to about 100 KU/l. More preferably, CGL will range from about 0.5 KU/l to about 75 KU/l, and still more preferably from about 1 KU/l to about 50 KU/l. Most preferably, final concentrations of CGL will range from about 1 KU/l to about 30 KU/l.

In some preferred embodiments, the buffer of Reagent 1 is TRIS, 250 mM at pH 8.4. However, when TRIS is used as the buffer the pH may range from 7.0–9.0. More preferably, the pH ranges from 7.5–8.5 and still more preferably from about 8.1–8.5. The use of increased concentration of TRIS improves assay consistency by helping to maintain a more constant pH as it is a more concentrated buffer. Additionally, CBS and CBL are substantially more active in this preferred pH range, and especially from about pH 8.1–8.5.

The present invention also provides an assay which works equally well with turbid samples. Problems with turbidity are reduced by adding lipase and α-cyclodextrin to R1. These help to decrease turbidity by the hydrolysis of triglycerides to glycerol and free fatty acids by lipase and by the formation of complexes with the free fatty acids by the α-cyclodextrin. The addition of these two components helped to clear the reaction mixture before the addition of Reagent 3. Replacing lipase and α-cyclodextrin with EDTA provides another means of accurately analyzing turbid samples.

Another variation of the present invention tested the effects of varying volumes of the reagents. Such variations did not have a substantial effect on the accuracy of the assay.

The present invention also tested the effects of different detergents and concentrations thereof. For example, Genapol X-80 may be present in Reagent 1 at a concentration between about 0.05–0.5%. More preferably, the concentration is between 0.1–0.5% and still more preferably between about 0.2–0.4%. Of these, three concentrations (0.1%, 0.3%, and 0.5%) were tested with the 0.3% concentration providing the most accurate results. Brij-35 was also varied in concentration in Reagent 1. Brij-35 may be used with the present invention in R1 at a concentration between about 0.01–0.5%. More preferably, this concentration ranges from about 0.015–0.1%, and still more preferably from about 0.020–0.030%. Of the concentrations tested (0.025%, 0.05%, 0.1% and 0.5%), the most accurate and consistent results were obtained using a concentration of 0.025%.

The present invention also tested replacing the reducing agent DTE with Tris (2-carboxyethylphosphine) hydrochloride (TCEP) which is stable in purified water for an extended period of time. Such a substitution reduced the reagent blank reaction from about 12–15 mA/min to about 4–5 mA/min which enables a greater degree of precision for this assay. When TCEP is used in the present invention, it may range in concentration from about 6–53 mM. More preferably, this concentration ranges from about 10–45 mM and still more preferably from about 20–30 mM. In the concentrations tested in this application, 26.44 mM provided the most accurate assay results.

The mixture comprising Reagent 3 was also varied in composition. For example, the Tris buffer was replaced with a phosphate buffer and glycerol was added to the buffer. The phosphate was effective at concentrations ranging from about 50 mM to about 500 mM at pH 7.6. The glycerol concentrations ranged from about 0.5% to 15.0% (v/v). Phosphate and glycerol were used to provide longer shelf-life for the enzymes, which was not possible with the TRIS buffer.

One of the advantages of the present invention is that it may be used with any of a number of instruments. For example, the assay was adapted for testing on two different instruments, the Hitachi 911 and the Beckman CX5. Notably, accurate and consistent results were obtained with either machine. Additionally, the assay can be run using just 2 reagents by mixing the components of R1 and R2 together in the correct ratio based on the instrument requirements.

Finally, the present invention can be adapted for use with a single calibration point. Importantly, the results from single point calibration was just as accurate as a multi-point calibration curve.

DESCRIPTION OF THE SPECIFIC EMBODIMENTS

Figure 1:
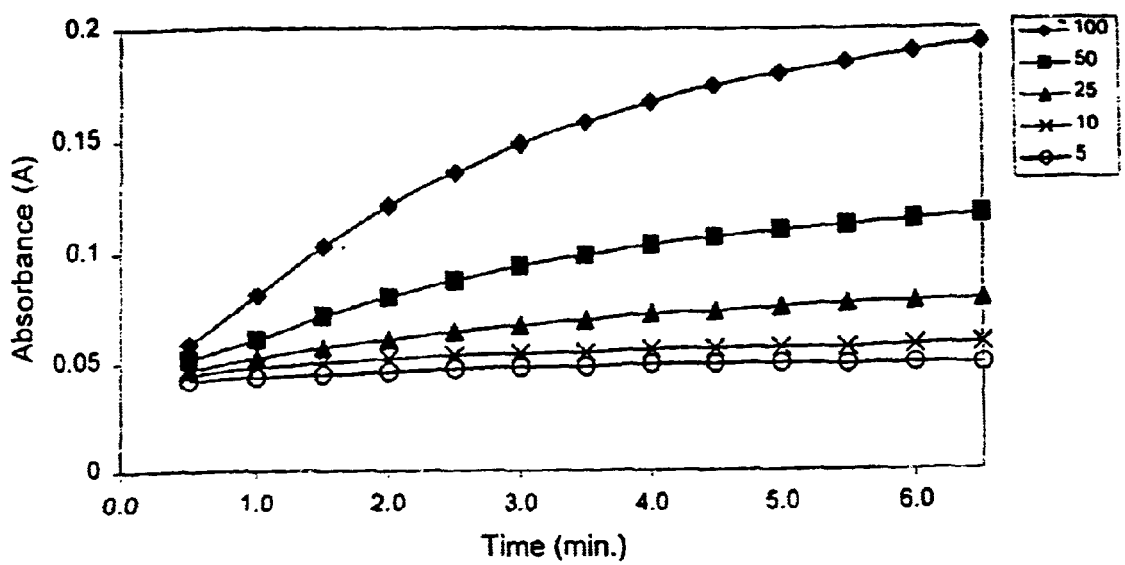
FIG. 1 depicts absorbance versus time plots obtained using aqueous solutions of pyruvate (5–100 μM) demonstrating the quantitation of pyruvate. Reagent components were those described in Table 1. and instrument settings those described in Table 2.

The present invention provides a homogeneous enzymatic cycling assay for assessing the amount of homocysteine in a sample. Enzymatic cycling maintains a steady-state level of homocysteine and further provides an increase in the sensitivity of assaying homocysteine. Further, the present invention provides genes and expression vectors for the recombinant production of enzymes that are useful in the present invention. Test kits for assessing the amount of homocysteine and/or cystathionine in a solution are also provided.

Homocysteine is present in cells as an intermediary amino acid produced when methionine is metabolized to cysteine. Generally, homocysteine produced in the body is rapidly metabolized by one of two routes: (1) condensation with serine to form cystathionine or (2) conversion to methionine, and its concentration (and that of its oxidized form, homocystine) in the body under normal conditions is low. The average plasma homocysteine level for a healthy adult is about 12 μM for males ranging from about 8.6 to about 17.1 μM and 10 μM for females ranging from about 3.9 to 16.8 μM (Vester et al., *Eur. J. Clin. Chem. Biochem.*, 29:549–554 (1991); Jacobsen et al. *Clin. Chem.*, 40:873–881 (1994)).

Recently it has been determined that the amount of homocysteine levels in a biological sample is of clinical significance in a number of conditions. Elevated amounts of homocysteine in the blood have been correlated with the development of atherosclerosis (Clarke et al., *New Eng. J.*

Med., 324:1149–1155 (1991)). Also, moderate homocysteinemia is now regarded as a risk factor for cardiac and vascular disease. Accuracy in the normal range of homocysteine found in normal adults is very important since the risk for heart disease has been determined to increase markedly with as little as 30% over the normal concentration increasing the associated risk factor by 3.4 fold (Stampfer et al., JAMA 268:877–881 (1992)).

As used herein the term "assessing" is intended to include both quantitative and qualitative determination of the amount of homocysteine and/or cystathionine present in a test solution. A "solution" or "test solution" as used herein refers to a clinical or biological fluid sample or tissue extract and can include, for example, blood, blood derivatives, such as plasma, or urine, and the like.

A sample containing homocysteine reacts with L-serine to form cystathionine in the presence of the enzyme CBS. Cystathionine can then be converted to homocysteine, pyruvate, and ammonia with a second enzyme, CBL. The result of using these anabolic and catabolic enzymes operating simultaneously is a "futile cycle," whereby (1) cystathionine and homocysteine are continuously interconverted, (2) serine is degraded, and (3) pyruvate and ammonia are created.

Use of relatively high concentrations of serine compared to homocysteine provides for conditions conducive to an overall reaction rate which follows pseudo-first order kinetics dependent directly upon the amount of homocysteine and cystathionine in the reaction. If the concentration of cystathionine is very low compared to the concentration of homocysteine, the rate of the overall reaction will vary linearly with the amount of homocysteine. By measuring the reduction in serine or the increase in either pyruvate or ammonia, the amount of homocysteine in an unknown solution or sample can be determined by a comparison with control reactions comprising known concentrations of homocysteine undergoing the identical enzyme reactions. The enzymatic cycling method of the present invention provides an amplification process producing far greater amounts of end products than the amount of homocysteine likely to be in a test solution, i.e., blood. Therefore, the assays to determine the amount of pyruvate or ammonia produced by the reaction do not have to be extremely sensitive and can be measured by existing processes known to the skilled artisan.

Pyruvate is typically measured by the enzymatic conversion into lactate with lactate dehydrogenase, or a derivative thereof. This enzymatic conversion reaction requires the cofactor NADH (reduced nicotinamide cofactor), or a derivative thereof, which is converted to NAD+ (oxidized nicotinamide cofactor). The reaction can be monitored by measuring the absorbance at 340 nm. As used herein, the term "derivatives," with respect to cofactors, refers to salts, solvates, and other chemically modified forms that retain overall cofactor activity, but can have extended stability in aqueous solutions. Derivatives can include, but are not limited to acetyl derivatives of NADH, including 3-pyridinealdehyde-NADH, 3-acetylpyridine-NADH, 3-thioicotinamide-NADH, and the like (See, for example, U.S. Pat. No. 5,801,006).

Other convenient assays to determine the oxidation of NADH, or a derivative thereof, include for example, the measurement of fluorescence, as described by Passoneau et al., in Enzymatic Analysis, A Practical Guide, pages 219–222 (1993), (incorporated herein by reference). In another embodiment, NADH, or a derivative thereof, reacts with pyruvate in the presence of lactate dehydrogenase to form NAD+, which further reacts with a dye capable of producing a color change, preferably in the visible range, when oxidized. The color change of the dye can be used to determine the total amount of oxidation of NADH to NAD+ which corresponds to the amount of pyruvate formed from the enzymatic cycling reaction. Examples of dyes which can be used in the present invention include, but are not limited to, 5,5'-dithiobis(2-nitrobenzoic acid), 2,6-dichlorophenolindophenol, tetrazolium compounds, phenazine methosulfate, methyl viologen, and derivatives of each.

Pyruvate can also be measured in a reaction with pyruvate oxidase, or a derivative thereof, in the presence of a peroxidase, i.e., horseradish peroxidase, and the like. The amount of pyruvate converted to hydrogen peroxide is determined by the oxidative condensation of, for example, a water soluble hydrogen donor which provides a colored compound for photometric determination of the concentration of peroxide. Particularly preferred hydrogen donors which provide a stable color reaction product include water soluble derivatives of N-alkyl-N-sulfopropylaniline derivatives, i.e., the sodium salt of N-ethyl-N-(2-hydroxy-3-sulfopropyl)-m-toluidine (TOOS) (Tamaoku et al., Chem. Pharm. Bull. 30:2492–2497 (1982)). The quantity of $H_2O_2$ can also be measured electrometrically. This includes amperometric and potentiometric measurements. The determination of the amount of homocysteine and/or cystathionine is determined from the correlation of the amount of peroxide produced from the conversion of pyruvate by pyruvate oxidase over a defined time period.

Ammonia also can be measured by different methods, including by use of an ammonia sensor (Willems et al., Clin. Chem. 34:2372 (1988). Ammonia can also be readily detected using known calorimetric techniques. For example, ammonia generated in the sample can be reacted to form a colored product, the formation of which can be detected spectrophotometrically. One such method, described in Methods of Enzymatic Analysis (Bergmeyer) 1:1049–1056 (1970), incorporated herein by reference, relies upon the reaction of ammonia with phenol in the presence of hypochlorite in alkaline conditions to form the colored dye indophenol. Sodium nitroprusside can be used as a catalyst. Modifications of the method using for example various derivatives can also be used. The colored end product is formed in amounts directly proportional to the concentration of ammonia, and hence homocysteine. Other methods can include, for example, microdiffusion analysis (Seligson et al., J. Lab. Clin. Med., 49:962–974 (1957), an ion exchange technique (Forman, Clin. Chem., 10:497–508 (1964), and various enzymatic methods (See, for example, Mondzac et al., J. Lab. Clin. Med., 66:526–531 (1979)).

The enzymatic cycling method for assessing the amount of homocysteine and/or cystathionine reduces the difficulties seen in other prior assays where background compounds and background reactions produced "noise." In the assay of the present invention, large amounts of an inexpensive amino acid, e.g., L-serine, can be added to provide for the overall conversion of L-serine to pyruvate and ammonia. In a preferred embodiment, a serine concentration of 250 $\mu$M or more can be used, and subsequently converted to pyruvate and ammonia. Plasma, typically contains about 100 $\mu$M serine. This amount of endogenous serine is immaterial to the present assay since the assay measures a rate of conversion that is limited by the amount of homocysteine and not the amount of serine. L-serine concentrations of about 0.1 mM to 10 mM would not be expected to affect the sensitivity or accuracy of the disclosed assay.

Further, the enzymatic cycling reaction of the present invention provides a rate of L-serine conversion that is dependent upon the concentration of homocysteine in a pseudo-first order reaction. Normal blood pyruvate levels are typically between about 0.4 and 2.5 mg/100 ml (Lehninger, AL. Principles of Biochemistry. 1982. Worthington Publishers, Inc. p. 707, incorporated herein by reference), which corresponds to about 45–284 $\mu$M. This concentration of pyruvate could provide a minor background measurement, but the present assay measures a change over time and can be easily adjusted for the starting level of pyruvate in a solution. In addition, pyruvate may be removed by prior incubation with lactate dehydrogenase or other enzymes. More importantly, cysteine and other sulfur-bearing compounds in, for example, blood, do not contribute significantly to the enzymatic cycling reaction and, therefore, are considered insignificant noise in the system.

In an alternative embodiment of the present invention the sample can be treated to remove cystathionine to increase the accuracy of the homocysteine measurement. As a particular example, treatment comprises contacting cystathionine γ-lyase with the solution to convert cystathionine to α-ketoglutarate (a compound which can not participate in the enzymatic cycling described above). Prior to proceeding with the enzyme cycling assay to assess the amount of homocysteine, the cystathionine γ-lyase activity must be removed from the sample or destroyed, i.e., by heat, or the like.

This particular embodiment of the invention can also be used for the assessment of the amount of cystathionine by comparing the differences in the rate of production of pyruvate and/or ammonia in a sample treated and untreated with cystathionine γ-lyase prior to undergoing the enzymatic cycling assay. Therefore, the present invention can be used to determine the amount of cystathionine in an unknown sample, even if the sample contains homocysteine.

In certain biological samples, such as blood, homocysteine is often bound through a disulfide linkage to proteins, thiols, and other cellular components. Typically, the sample can be treated with a reducing agent, such as sodium or potassium borohydride; a thiol, such as dithioerythritol, β-mercaptoethanol, dithiothreitol, thioglycolic acid or glutathione; or a phosphine or a trialkylphosphine, such as tributylphosphine and tris(2-carboxyethyl)phosphine (TCEP), and the like, to liberate bound and disulfide linked homocysteine. Prior assays which require antibodies for the detection step must change the redox conditions of the reaction mixture (most antibodies are held together with a disulfide bond). However, in the present method it is not necessary to wash or alter redox conditions because the CBS and CBL used are active under reducing conditions. Therefore, fewer steps are required for the assays of the present invention than for many prior art immunoassays.

In a typical embodiment, a sample comprising blood, blood fractions, serum, plasma, or urine will be treated with a reducing agent and directly assayed for homocysteine. Heating of the sample prior to the assay to speed up the liberation of homocysteine and to inactivate degradative enzymes and other factors that may interfere with the assay may also be preferred. The general handling of blood samples for homocysteine assays is known to those skilled in the art for other methods such as HPLC tests.

CBS and CBL are enzymes commonly found in nature. Humans and yeast use CBS for the synthesis of methionine; and the human cDNA for CBS can substitute for the CBS gene in brewer's yeast (Kruger et al., *Hum. Molec. Genet.*, 4:1155–1161 (1995)). CBL is found in many bacteria, including *E. coli* (Laber et al., *FEBS Lett.*, 379:94–96 (1996). The entire DNA sequences for the CBS and CBL genes are known in these organisms and in other species, providing a skilled molecular biologist with a source to easily clone or synthesize these genes, or derivatives thereof.

As used herein "derivative" with respect to enzymes refers to mutants produced by amino acid addition, deletion, replacement, and/or modification; mutants produced by recombinant and/or DNA shuffling; and salts, solvates, and other chemically modified forms of the enzyme that retain enzymatic activity of the isolated native enzyme. A method for creating a derivative enzyme by DNA shuffling useful in the present invention is described in U.S. Pat. No. 5,605,793 (incorporated herein by reference). Even without cloning, the two enzymes have been purified from a number of different organisms. See, for example, Ono et al., *Yeast* 10:333–339 (1994); Dwivedi et al., *Biochemistry* 21:3064–3069 (1982), incorporated herein by reference. In a preferred embodiment of the present invention genetically modified organisms are provided to produce a CBS, or a derivative thereof, and to produce a CBL, or a derivative thereof, which can be used in the enzymatic cycling assay to provide reagents at a reduced cost and to increase the ease of purifying the enzymes.

Similarly, the term "derivative" with respect to nucleotide sequences refers to variants and mutants produced by nucleotide addition, deletion, replacement, and/or modification, and/or combinatorial chemistry; mutants produced by recombinant and/or DNA shuffling; and salts, solvates, and other chemically modified forms of the sequence that retains the desired activity of the sequence such as the binding characteristics of MetR. Preferably, when modified derivative sequences are used, the sequences have at least about 60% sequence identity with the original sequence. More preferably, this identity is at least about 70% and more preferably at least about 85%. Most preferably, such sequences have at least about 95% sequence identity with the original sequence.

The CBS gene and the entire genome of *Saccharomyces cerevisiae* have been sequenced. Likewise the CBL gene and the remaining genes of *E. coli* are also known. Therefore, using techniques common to the art of molecular biology, the genes encoding CBS and CBL can be cloned and expressed in both organisms. Published methods for purifying the two enzymes are known which use standard protein purification methods. However each of the enzymes can be constructed as fusion proteins including for example, a portion of another protein which assists in solubilization and/or refolding of the active enzyme or amino acid sequences which can be added to aid in purification. An example of amino acid sequences added for purification include, affinity tags, such as poly-His, or glutathione-S-transferase (GST) can be added to allow for the more rapid purification of the proteins over a single affinity column. Although the enzymes do not require purification to homogeneity for a diagnostic test of the present invention, proteases and other activities that convert serine to pyruvate can be reduced to insignificant levels by purification.

In addition, concentration of the enzymes generally leads to higher stability of enzyme activity during the reaction and upon long term storage. CBS and CBL from organisms other than *S. cerevisiae* and *E. coli*, especially thermophiles, are expected to be sources of enzymes having even greater stability. The isolated enzymes can also be selected for a higher affinity to homocysteine. In addition, protein engineering of the yeast CBS and bacterial CBL can lead to enzymes with improved commercial properties, including higher affinities, faster reaction rates, easier purification, and a longer half-life upon storage.

Similarly, cystathionine γ-lyase (CGL) has been described in detail in many species (see, for example, Yamagata, et al., J. Bacteriol., 175:4800–4808 (1993) incorporated herein by reference). Manipulation of the genes which encode CGL can be further modified genetically by standard recombinant methods and inserted into a host cell to develop higher level production strains.

Recombinant expression of the genes for CBS, CBL, and CGL are typical. These methods can provide large quantities of purified enzyme and the genes can be modified, for example, to add a defined peptide sequence (an affinity tag) to the expressed enzymes that can be used for affinity purification. Through the use of affinity tags in the expression of the recombinant enzymes, the purification and immobilization of these enzymes can be greatly simplified, leading to lower costs. Affinity tags are known in the art and include for example, but not limited, poly-histidine, GST (glutathione-S-transferase), strep-tag, "flag," c-myc sequences, and the like. Tags are widely used for affinity purification of recombinantly expressed proteins, and many are commercially available.

In a preferred embodiment, CBS and CBL are immobilized on a solid surface in a manner that maintains the activities of the enzymes and in a manner that keeps homocysteine free to interact directly with the proteins. By immobilizing the enzymes at high densities, the diffusion distances between the different proteins are reduced relative to enzymes in solution. As a result, the overall rate of reaction of the assay increases greatly, since the product of one enzyme can be reacted upon by the other enzyme and vice versa. Acceleration of the reaction rates is due to a local increase in the concentrations of the intermediates, which are in closer proximity to the next enzyme as a result of immobilization. Increasing the rate of the homocysteine assay can be an important factor for the marketability of the diagnostics product because the $K_m$ of CBS and of CBL are in the millimolar range but the blood concentrations of homocysteine are approximately 10 μM. Diffusion-limited reactions are known to require a high concentration of the enzymes to provide a rapid reaction rate. Immobilization of the enzymes in the cycling assay overcomes difficulties which might be presented by the low affinities of these two enzymes for their respective substrates.

In yet another preferred embodiment CBS and CBL are immobilized as a fusion protein. The distance and orientation of the two different proteins relative to each other can be controlled during the construction of the fusion gene expression vector. By properly positioning the two activities in a fusion protein, homocysteine and cystathionine interconversion can occur extremely rapidly virtually within the protein, since diffusion distances can be minimized between the two active centers. The homocysteine, therefore, behaves like a cofactor in the overall enzymatic cycling reaction, which makes pyruvate and ammonia from L-serine.

The enzymatic cycling assay of the present invention can be provided in a number of assay formats. The simplest format of the assay provides a reagent solution comprising L-serine, CBS, or a derivative thereof, CBL, or a derivative thereof, and various buffers and auxiliary substances necessary for optimization of the enzyme reactions. In a particularly preferred embodiment of the present invention CBS, or a derivative thereof, and CBL, or a derivative thereof, are provided immobilized on a solid surface.

Immobilization of enzymes to a solid surface while retaining substantially all the activity of the enzyme are well known in the art. Several methods have been used for immobilization including, covalent binding, physical absorption, entrapment, and electrochemical deposition. As one example glutaraldehyde has been used to immobilize creatinine deaminase and glutamate oxidase to propylamine derivatized controlled pore glass beads (Rui et al., Ann. NY Acad. Sci., 672:264–271 (1992)). Other examples include, but are not limited to, the use of carbodiimides to covalently attach enzymes to succinate derivatized glass beads (Rui et al., supra), and the use of hetero- or homo-bifunctional cross-linking reagents (e.g., SPDP, N-succinimidyl 3-(2-pyridyldithio)propionate; SMPT, succinimidyloxycarbonyl-α-methyl-α-(2-pyridyldithio)-toluene; DSP, dithiobis (succinimidylpropionate); DTSSP, 3,3'-dithiobis (sulfosuccinimidylpropionate); DSS, disuccinimidyl suberate, and the like) to covalently attach an enzyme through, for example an amine or sulfhydryl group to a derivatized solid surface (Wilson, et al., Biosens. Bioelectro., 11:805–810 (1996)).

The "solid surface" as used herein can include a porous or non-porous water insoluble material that can have any one of a number of shapes, such as a strip, rod particle, including a bead or the like. Suitable materials are well known in the art and can include, for example, paper, filter paper, nylon, glass, ceramic, silica, alumina, diatomaceous earth, cellulose, polymethacrylate, polypropylene, polystyrene, polyethylene, polyvinylchloride, and derivatives of each thereof. The solid surface can be the sides and bottom of the test container or can be a material added to the test container. In one preferred embodiment the solid surface comprises a bead which is added to the test container.

Both yeast and bacteria have enzymes that convert L-serine to pyruvate, activities that are sometimes referred to as serine deaminase or serine dehydratase. Well established mutagenic methods can be used to greatly reduce or eliminate these activities, which can contributed significantly to the background in the homocysteine cycling assay. Saccharomyces cerevisiae, in particular, maybe genetically manipulated to delete out the serine deaminase activities, which are necessary for (1) isoleucine synthesis and (2) growth on serine as a carbon or nitrogen source, by using a simple method known as "gene disruption." By deleting the cha1 gene of yeast, a major serine deaminase activity is removed, thereby eliminating one potential background problem to the cycling assay. In addition, the cha1 deletion can be useful for selecting CBS-CBL fusion proteins and for genetically engineering those fusion proteins. The cha 1 deletion strain is unable to grow on serine as the sole carbon or nitrogen source. The CBS-CBL fusion gene is able to complement the deletion, so long as homocysteine is available as a "cofactor," because the cycling system produces the same net result as the serine deaminase. Therefore, the cha 1 deletion can be used to select for and maintain improved CBS-CBL fusions, especially if a population of the fusion genes is mutated and placed on single-copy vectors or onto chromosomes in yeast. Cells that grow faster on serine media or have a reduced requirement for homocysteine may contain mutations that code for faster enzymes or proteins with higher affinities for homocysteine and cystathionine.

The present invention also provides, as an alternative method for assessing the amount of homocysteine in a sample, the use of a metabolite binding transcription factor. When a metabolite binding transcription factor is bound to their respective metabolite the factor complex binds to a specific receptor polynucleotide sequence. The binding of the transcription factor complex to its receptor consensus sequence can be monitored and correlated to the amount of the metabolite present in the sample.

A number of transcription factors that bind to specific DNA binding sites upon association with a small molecule or metabolite are known in the art. For example, *E. coli* has an operon regulatory element, the transcription factor MetR which regulates the Met operon in response to binding to homocysteine (Cai et al., *Biochem. Biophys. Res. Commun.*, 163:79–83 (1989)). MetR or derivatives thereof regulate genes such as MetE (cobolamin independent methionine synthase), MetH (cobolamin dependent methionine synthase) and GlyA (serine hydrogenase). MetR and its derivatives preferentially bind to its consensus DNA sequence in the presence of homocysteine and is free in the cell cytoplasm in its absence. The binding of MetR in the presence of homocysteine can be exploited to assess the amount of homocysteine in a sample suspected of containing homocysteine.

In a particular embodiment of the invention the assay comprises a polynucleotide sequence encoding the consensus sequence for a receptor polynucleotide for MetR immobilized on a solid support in a manner which allows for the accessibility of the consensus receptor sequence for binding to MetR. The nucleotide sequence can be, for example:

GTTAATGTTGAACAAATCTCATGTTGCGTG (SEQ ID NO: 11)

A sample, such as plasma, blood or urine, is treated to release any protein bound homocysteine prior to admixing the sample with a reagent solution comprising MetR in a buffering agent in the presence of the immobilized consensus receptor sequence under conditions conducive to complex formation. After an incubation period the solid support is washed to remove unbound reagents and the amount of MetR that remains bound to the solid support is assessed. The determination of the amount of MetR that remains bound to the solid surface typically can be an ELISA, surface plasmon resonance, i.e., BIACORE, or simply a standard protein assay, and this amount is correlated with the amount of homocysteine present in the sample.

Treatment of the sample to release homocysteine can be accomplished with a reducing agent. As described above a number of agents are well known in the art. Typically a sample will be admixed with a buffer solution containing a sufficient amount of reducing agent to release substantially all of the homocysteine from any associated proteins present in the sample. Commonly used reducing agents include, but are not limited to, sodium and potassium borohydride, β-mercaptoethanol, dithiothreitol, dithioerythritol, thioglycolic acid or glutathione; or a phosphine or a trialkylphosphine, such as tributylphosphine and tris(2-carboxyethyl)phosphine (TCEP), and the like.

The MetR protein can also be modified to incorporate a detectable label, such as a chromophore, a fluorophore, and the like, to improve the speed and sensitivity of the assay. The addition of the detectable label can reduce the time period required to run the assay by eliminating certain sample handling steps, for example, additional washing steps. Incorporation of a fluorophore that emits light at the wavelength absorbed by oligonucleotides into the consensus binding sequence allows for the measurement of fluorescent energy transfer to quantify the binding of the protein to the consensus sequence. Methods which can be used to measure fluoresence transfer include, for example, Fluorescence resonance energy transfer (FRET) or a proximity scintillation assay. Additional modification of the MetR binding consensus sequence by the addition of an additional detectable label within the binding domain can also improve the specificity of the assay.

Additionally, a defined peptide sequence (an affinity tag) can be added to the MetR protein to aid in purification and detection. Affinity tags are known in the art and include for example, but not limited, poly-histidine, strep-tag, "flag," c-myc sequences, and the like. Tags are widely used for affinity purification of recombinantly expressed proteins, and many are commercially available. Further, mutational alterations to improve binding affinity of a recombinantly expressed MetR can be used to provide additional assay reagents.

In a separate embodiment of the present invention, the amount of homocysteine in a sample can be determined by the enzymatic utilization of homocysteine in the sample. Conversion of homocysteine in cellular metabolism typically releases a proton from the sulfhydryl residue of homocysteine. Release of this proton was used to measure the binding affinity of homocysteine to *E. coli* cobolamin dependent methionine synthase (Jerret et al., *Biochemistry*, 36:15739–15748 (1997)). Enzyme reactions catalyzed by proteins, such as methionine synthase, generally require cofactors or additional substrates to complete the reaction. If these cofactors and substrates are not present, the homocysteine remains bound to the enzyme. In the present method, measurement of the released proton removes the proton released by the enzymatic reaction driving the reaction toward consumption of the homocysteine present in the sample. The measurement of the change in pH associated with the released protons provides a determination of the amount of homocysteine in the sample. In a preferred embodiment, for example, cobolamin independent methionine synthase, can be used in the assay.

As a matter of convenience, the reagents for use in the present invention can be provided in a test kit for use in the assay method. A typical kit comprises a packaged combination of a container to hold the test solution, L-serine, CBS, or a derivative thereof, and CBL, or a derivative thereof, and auxiliary buffers and substances required for optimal reaction conditions. Importantly, a variety of preservatives and/or stabilizing agents may also be included with any/all kit reagents and/or enzymes to elongate shelf life as well as "on-line" life for sample testing. The kit can further comprise reducing agents or CGL for pretreating the sample prior to the cycling assay. Further, the kit can include lactate dehydrogenase, NADH and a dye capable of an observable color change upon oxidation.

Under appropriate circumstances one or more of the reagents in the kit can be provided in solution (with or without preservatives and/or stabilizing agents) or as a dry powder, usually lyophilized, including excipients, preservatives, and/or stabilizing agents, which on dissolution can provide for a reagent solution having the appropriate concentrations for performing the assay in accordance with the present invention. To enhance the versatility of the subject invention, the reagents can be provided in packaged combination, in the same or separate containers, so that the ratio of the reagents provides for substantial optimization of the method and assay. The reagents can each be in separate containers or various reagents can be combined in one or more containers depending on the stability of the reagents. As a matter of convenience, the reagents employed in the assay method of the present invention can be provided in predetermined amounts. The test kit can also contain written instructions on how to use the reagents and/or how to perform a particular assay, for example in the form of a package insert.

The following examples are offered by way of illustration, not by way of limitation.

EXAMPLE 1

Cloning and Expression of the E. coli Cystathionine β-Lyase Gene

In this example standard PCR procedures were used to clone the E. coli CBL gene. The isolated gene was inserted into an expression vector with an affinity tag sequence (6HIS), and the expressed protein was purified with an affinity column. A substantial amount of the CBL enzyme activity in the host cells transformed with the expression vector construct was purified from the cell lysates.

Cloning of the E. coli Cystathionine β-lyase (CBL, EC 4.4.1.8) Gene

Standard PCR procedures using EXPAND HIGH FIDELITY PCR system (Roche Biochemicals) were employed to amplify the E. coli CBL gene using ONE SHOT TOP10 competent E. coli cells (Invitrogen) as the genomic DNA source. PCR primer sequences for CBL cloning were as follows: (CBL N-terminal primer: 5'-CGACGGATCC GATGGCGGACAAAAAGCTTG-3'; SEQ ID NO: 1) and (CBL C-terminal primer: 5'-CGCAGCAGCT GTTATACAATTCGCGCAAA-3'; SEQ ID NO: 2). The PCR amplified CBL gene product was then purified by agarose gel electrophoresis, digested with BamHI and PvuII restriction endonucleases, and purified again by agarose gel electrophoresis. The purified E. coli CBL gene was then ligated into gel purified, BamHI/PvuII digested pRSETB protein expression vector (Invitrogen). The resulting construct provided the CBL gene under control of the T7 transcriptional promoter, cloned in frame with an amino terminal six Histidine (6HIS) residue leader sequence (hereafter referred to as 6HISCBL) which allows for convenient expression, affinity purification, and immunostaining analysis of recombinant 6HISCBL protein from E. coli cells. The DNA sequence of E. coli Cystathionine β-lyase (CBL) gene is presented (SEQ ID: 21). The protein sequence of the cloned E. coli Cystathionine β-lyase (CBL) having an amino-(NH3)-terminal 6Histidine (6His) affinity tag, resulting from cloning the CBL gene into the pRSETB bacterial expression plasmid is also presented (SEQ ID: 19).

Cystathionine β-lyase Protein Expression and Purification

The pRSETB(6HISCBL) plasmid construct was transformed into BL21(DE3)pLysS E. coli strain (Invitrogen), spread on LB/Agar plates containing (100 μg/ml ampicillin, 35 μg/ml chloramphenicol), and was then incubated overnight at 37° C. Single bacterial colonies were then transferred and grown overnight in flasks containing 100 ml LB growth medium containing ampicillin and chloramphenicol. The 100 ml overnight culture was then added to multiple flasks containing 1 L of fresh LB growth medium containing ampicillin, and allowed to grow until reaching an $A_{600}$ of 0.6 (approx. 2.5 hours). In order to induce CBL protein expression (driven by the T7 promoter), isopropyl-β-D-thiogalactopyranoside (IPTG) was then added to the growth medium to a 0.1 to 1 mM final concentration. The CBL enzyme cofactor pyridoxal 5'-phosphate (PLP) was also added to a final concentration of 100 μM in the growth medium during induction. After monitoring cell growth and 6HISCBL protein expression over a 5 hour period, E. coli cells were harvested by centrifugation, resuspended, and lysed by the addition of BUGBUSTER Protein Extraction Reagent (Novagen Inc.) in the presence of EDTA free complete protease inhibitor (Roche Biochemicals) as described in the manufacture's protocol. The cell lysate was then treated with DNase I, cleared by centrifugation and loaded onto an affinity column containing Poly-His Protein Purification Resin (Roche Biochemicals). The column was then washed with 10 bed volumes of equilibrating buffer (50 mM KPi, pH 7.8, 0.5 M NaCl), followed by elution with 5 bed volumes of elution buffer 1 (50 mM KPi, pH 7.8, 0.5 M NaCl, 10 mM imidazole; EB1), 5 bed volumes of elution buffer 2 (50 mM KPi, pH 7.8, 0.5 M NaCl, 50 mM imidazole; EB2), and 5 bed volumes of elution buffer 3 (50 mM KPi, pH 7.8, 0.5 M NaCl, 500 mM imidazole; EB3). Samples taken during each step of the purification procedure were then analyzed by denaturing protein gel electrophoresis (SDS-PAGE) and stained with either Coomassie Brilliant Blue, or subjected to Western blot analysis using a monoclonal anti-polyhistidine peroxidase conjugated mouse immunoglobulin for detection as described by the manufacturer (Sigma).

The purified 6HISCBL protein was found to elute primarily in elution buffers 2 and 3 (EB2 and EB3). The CBL containing eluate was then concentrated using centrifugal filtration chambers (Amicon) and dialyzed overnight at 4° C. against storage buffer (50 mM TrisHCl, pH 8, 100 mM NaCl, 5 mM PLP), aliquoted and stored frozen at −80° C. The concentration of purified homogenous CBL enzyme was then calculated on the basis of the extinction coefficient at 280 nm and a subunit weight of 43,312 Da. (Clausen et al. Biochem. 36:12633–42 (1997)). A typical yield of purified 6HISCBL was in the range of 20–30 mg 6HISCBL per gram of E. coli cell paste.

CBL Activity Assay

The CBL activity of affinity purified recombinant 6His-CBL protein expressed from the pRSETB(6HisCBL) plasmid construct was performed essentially as described previously (Clausen et al., Biochem. 36:12633–42 (1997) incorporated herein by reference). Briefly, assay mixtures contained 100 mM Tris/HCl (pH 8.5), 5 mM L-cystathionine, 1 mM 5,5'-dithiobis(2-nitrobenzoic acid) (DTNB; Ellman's reagent), and 6HisCBL enzyme in a final reaction volume of 1 mL. The reaction was followed by recording the increase in absorbance at 412 nm with time. The same enzyme reaction was also carried out on samples having known concentrations of substrate to produce a standard curve. Substantially all of the CBL activity detected in the whole cell lysate was recovered and found present in the experimentally purified samples of recombinant 6His-CBL enzyme produced from the pRSETB(6HisCBL) plasmid construct.

EXAMPLE 2

Cloning and Expression of the Yeast Cystathionine β-Synthase (CBS) Gene in Yeast In this example PCR methods were used to clone the CBS gene from yeast. The PCR fragment comprising the CBS gene was inserted into an expression vector both with and without an affinity tag which was added to assist in purification of the expressed gene product.

A laboratory strain of Saccharomyces cerevisiae (5153-11-1 (his3 met2)) was used as the source of the CBS gene. The cells were grown on YEPD at 32° C., spun down, washed with water, and transferred into 200 μl of Yeast Plasmid Buffer (100 mM NaCl, 10 mM Tris (pH 8), 1 mM EDTA, 0.2% SDS). The cell suspension was mixed with an equal volume of 0.45 mm glass beads and vortexed at high speed for 3×30 seconds. The liquid was removed by pipetting and centrifuged for two minutes in a microfuge to remove cell debris. The supernatant was extracted with PCI (phenol:chloroform:isoamyl alcohols (25:24:1) and chloroform. Sodium chloride (5 M) was added (about 20 µl), and the DNA was precipitated with an equal volume of isopropanol.

This genomic yeast DNA was amplified by PCR with primers CI-001 (CGGGGATCCTGATGCATGCATGATAAGGA; SEQ ID NO: 3) and CI-012 (CGGCATTACCGTTT CACTAATTTATTG; SEQ ID NO: 4), which are published nucleotide sequences that flank the structural gene for the yeast CBS. Primer CI-001 (SEQ ID: 3) contains a BamHI site found on the untranslated 3' side of the CBS gene. To add a BamHI sequence to the 5' side of the PCR fragment, the gene was further amplified by PCR with CI-001 (SEQ ID NO: 3) and CI-002 (GTTGGATCCGGCATTACCGTTTCAC; SEQ ID NO: 5). The resulting PCR product was a DNA sequence of approximately 1937 base pairs, including 1521 base pairs that encode the CBS protein. The additional DNA that flanks the coding sequence comprises the natural promoter and transcription termination sequences of the yeast CBS gene.

A stronger promoter was inserted upstream of the CBS gene to promote higher levels of protein expression. The yeast TPI1 promoter was cloned from the same genomic yeast DNA using the primers CI-009 (GGTGGATCCATCAATAGATACGTA CGTCCT; SEQ ID NO: 6) and CI-010 (TTTTAGTTTATGTATGTGTTTTTTG; SEQ ID NO: 7) in a standard PCR reaction. To attach the CBS coding region to the TPI1 promoter, an adapter primer is used: CI-011 (AACACATACATAAACTAAAAATGACT AAATCTGAGCAGCAA; SEQ ID NO: 8), which contains 20 bases of the TPI1 promoter and the first 21 bases of the CBS gene. The CBS sequence obtained above was amplified by PCR with primers CI-001 (SEQ ID NO: 3) and CI-011 (SEQ ID NO: 8). The resulting PCR product was mixed with the TPI1 promoter product from above, and the mixture was amplified by PCR with primers CI-001 (SEQ ID NO: 3) and CI-009 (SEQ ID NO: 6) to produce a fusion gene designated "TPICBS," that comprising the TPI1 promoter, the CBS coding sequence, and the CBS transcription terminator.

The CBS and TPICBS PCR products each comprise BamHI sites on both the 5' and 3' sides of the coding region. These PCR products were purified with a PCR WIZARD PREP (Promega), according to the manufacturer's recommendations, and were cut with BamHI. The resulting BamHI nucleotide fragments were run on a 1% Agarose TBE Gel and purified with NA45 paper (S&S). The yeast, *E. coli* shuttle vector C1-1 has a unique BamHI site in the gene for tetracycline resistance was used for expression of the CBS gene. C1-1 vector was cut with BamHI and treated with shrimp alkaline phosphatase, according to the manufacturer's instructions (Roche Biochemicals). The CBS and TPICBS BamHI fragments were ligated into the linearized C1-1 vector. The ligation reaction was transformed into TOP10 cells (Invitrogen), which were plated onto LB ampicillin plates. Amp-resistant transformants were transferred onto LB amp and LB tet plates to determine tetracycline sensitive clones. Several tet-sensitive colonies were selected from the LB amp plates, grown overnight on LB amp plates, and were further processed by the alkaline lysis method for plasmid DNA. The DNA was cut with BamHI and separated on a 1% agarose gel to determine which plasmids contain the CBS or TPICBS inserts.

C1-1 plasmids that carry inserts were transformed into the yeast strain, INVSc-1, a diploid strain that is commercially available from Invitrogen. INVSc-1 has a mutation in both copies of the LEU2 gene and requires the LEU2 gene from the C1-1 plasmid for selective growth on leucineless media. INVSc-1 was transformed with the C1-1 related plasmids, using the Yeast Transformation Kit from Invitrogen, according to the manufacturer's instructions. This kit involved making spheroplasts of the cells with Zymolyase, followed by a calcium treatment for DNA transformation. The transformants were plated onto a synthetic medium containing 1M sorbitol, yeast nitrogen base, and yeast supplements, excluding leucine. Transformants were visible in the overlay agar after three days of incubation at 32° C.

Attachment of Poly-Histidine to Cystathionine β-synthase for Yeast Expression

DNA sequences that encode six histidines were added to the 3' end of the CBS coding region, in both the CBS and TPICBS vector constructs. Poly-histidine coding sequences were added to the original CBS clone by amplification of the CBS-PCR fragment from above with the primer CI-017 (ATGATGATGATGATGATGACCTGCT AAGTAGCTCAGTAA; SEQ ID NO: 9) and primer CI-002 (SEQ ID NO: 5). The resulting PCR product comprises the natural CBS promoter region, the CBS coding region, and a further coding sequence for glycine and six histidine residues. The glycine residue was added to increase the spatial flexibility of the poly-his peptide after translation. The poly-hisCBS PCR product was gel-purified away from the original CBS DNA and was amplified by PCR sequentially twice thereafter with primers, CI-002 (SEQ ID NO: 5) and CI-017 (SEQ ID NO: 9) to virtually eliminate the original CBS DNA.

Similarly, the TPICBS PCR product from above was amplified with primers, CI-009 (SEQ ID NO: 6) and CI-017 (SEQ ID NO: 9). The PCR product was gel purified and reamplified twice with CI-009 (SEQ ID NO: 6) and CI-017 (SEQ ID NO: 9) to greatly reduce the input TPICBS DNA sequence.

The CBS gene was also cloned by PCR with primers CI-001 (SEQ ID NO: 3) and CI-018 (CATCATCATCATCATCATTAAATAAGAACCCACGCT; SEQ ID NO: 10) to produce a poly-histidine sequence with a TAA stop codon, followed by the transcription terminator sequence. This short PCR product ("terminator") of about 190 bp was also gel purified and cloned by PCR with the same primers. The poly-his CBS and "terminator" fragments were combined into one PCR reaction with the primers, CI-001 (SEQ ID NO: 3) and CI-002 (SEQ ID NO: 5). The resulting amplification produced a nucleic acid molecule designated "CBSH," comprising the natural CBS promoter, the entire CBS coding region, one additional glycyl residue, six histadyl residues with a stop codon, and the CBS transcription terminator.

Likewise, the poly-his TPICBS and terminator fragments were combined into one PCR reaction with the primers, CI-001 (SEQ ID NO: 3) and CI-009 (SEQ ID NO: 6). The resulting nucleic acid product, designated "TPICBSH" was the same as the CBSH sequence, except that the TPI1 promoter replaced the natural CBS promoter. The CBSH and TPICBSH (each containing a poly-histidine affinity tag sequence) were cut with BamHI and ligated into C1-1, as done above for the CBS and TPICBS sequences. The ligation mixes were transformed into INVSc-1. Tet-sensitive colonies were examined for the insertion of the appropriate cloned genes into C1-1 by restriction enzyme analysis.

EXAMPLE 3

Cloning, Expression, and Purification of the Yeast Cystathionine β-Synthase (CBS) Gene in *E. coli*

In this example standard PCR and molecular biology techniques were used to clone the *Saccharomyces cerevisiae*

(INVSc1) Cystathionine β-Synthase (CBS) gene as a fusion protein with an amino-terminal glutathione S-transferase (GST). Addition of this region of glutathione S-transferase allows for the single-step affinity purification of the CBS protein from the *E. coli* culture medium and may also assist in solubilization and/or to promote proper refolding of the enzyme in an active form.

Cloning

The laboratory strain of *Saccharomyces cerevisiae* (INVSc1) (Invitrogen) was used as the source of CBS gene. A single colony of INVSc1 yeast was boiled in 100 μl of deionized water for 5 min. and vortexed rapidly in the presence of an equal volume of 0.45 mm glass beads for 2 min. One microliter of this cell lysate was then used as the source of DNA for PCR amplification of yeast CBS gene using primers CI-024 (GCGGGTCGACTATGACTAAATCTGAGCAGCAAGCC; SEQ ID NO: 12) and CI-025 (GCGTGCGGCCGCGTTATGCTAAGTAGCTCAG; SEQ ID NO: 13) which contain flanking sequences to the published yeast CBS gene and restriction sites for cloning into the pGEX-6P-2 (Amersham Pharmacia) expression vector. The resulting PCR product (approximately 1548 bp) was then isolated and purified by agarose gel DNA extraction using a commercial kit (Roche). The purified PCR product containing the CBS gene flanked by SalI (5'end) and NotI (3' end) restriction enzyme sites was then digested (by SalI and NotI), gel purified, and ligated into the pGEX6P-2 expression vector (Amersham Pharmacia). Restriction enzyme mapping was used to confirm the identity of the PCR amplified DNA as the yeast CBS gene. The DNA sequence for the cloned *Saccharomyces cerevisiae* Cystathionine β-Synthase (CBS) gene is depicted (SEQ ID: 14). The protein sequence of the cloned *Saccharomyces cerevisiae* CBS having an amino-(NH3)-terminal GST fusion protein attached as a result of cloning into the bacterial expression vector pGEX6P-2 is also presented (SEQ ID: 20).

Expression and Purification

The pGEX6P-2 expression vector containing the cloned yeast CBS gene (described above) was transformed into TOP10 *E. coli* cells (Invitrogen). Single colonies were picked and cell cultures were grown in LB media containing 100 μg/ml ampicillin at 30EC until reaching an absorbance at 600 nm of approx. 0.5 OD. In order to induce expression of the GST-CBS fusion protein, (driven by the tac promoter), isopropyl-β-D-thiogalactopyranoside (IPTG) was added to the growth medium to a final concentration of 0.1 mM. The CBS cofactor, pyridoxal 5' phosphate, was also added to the growth medium at 100 μM final concentration during induction. Induced cells were then allowed to grow at 30° C. for an additional 21 hrs before harvesting by centrifugation.

Affinity purification of the GST-CBS protein using Glutathione Sepharose 4B affinity resin was then performed essentially as described in the manufacture's protocol (Amersham Pharmacia). Briefly, cells were suspended in phosphate buffered saline (PBS) and disrupted by sonication on ice. TritonX-100 was then added to a final concentration of 0.1% (v/v), and the sonicate was shaken at room temperature of 30–45 min. The cell lysate was then cleared of insoluble debris by centrifugation, treated with DNase I, and loaded onto a column of Glutathione Sepharose 4B affinity resin. Nonspecifically bound proteins were washed away with 10 column volumes of PBS, and the desired GST-CBS protein was then eluted from the affinity resin by the addition of 5 column volumes of elution buffer (50 mM Tris, pH 8, 1.4mM β-mercaptoethanol (BME), 100 mM NaCl, 0.1% (v/v) TritonX-100, 50 mM reduced glutathione). Purification of the GST-CBS fusion protein was then confirmed by Coomassie Blue stained SDS-PAGE (sodium dodecylsulfate, polyacrylamide gel electrophoresis). The eluted GST-CBS was then dialyzed into storage buffer (50 mM TrisHCl, pH8, 100 mM NaCl, 5 μM PLP), aliquoted and stored at −80° C. The concentration of purified GST-CBS was then determined using the MICRO BCA Protein Assay Kit (Pierce Chemical). A typical yield of purified GST-CBS was in the range of 5–10 mg GST-CBS per gram of *E. coli* paste.

Activity Assay for CBS

The CBS activity of the purified yeast GST-CBS fusion protein was performed as described by Kashiwamata and Greenberg (*Biochim. Biophy. Acta* 212:488–500 (1970)). This assay is based on the ability of CBS to synthesize cystathionine from serine and homocysteine. The amount of cystathionine formed by CBS was then determined spectrophotometrically by detecting the ninhydrin reaction chromagen at 455 nm and compared to a standard curve generated using samples of known cystathionine concentrations. CBS activity was also determined by the enzymatic assays described infra, or by other assays well known to the skilled artisan.

EXAMPLE 4

Construction of ADH2CYS4 Fusion Construct Expression and Purification of Yeast Cystathionine β-Synthase in Yeast In this example a strong promoter, ADH2, was inserted upstream of the CYS4 gene and constructed as a fusion with the yeast CBS gene to promote higher protein expression. The ADH2 promoter is regulated by the Adr1p, and is repressed when yeast cells are grown in glucose containing medium and becomes derepressed when the cells are grown in a non-fermentable carbon source. This allows for regulated expression, if overproduction of a protein is lethal to the cell.

Construction of ADH2CYS4 Gene

Yeast genomic DNA was amplified with primers CI-029 (CTATATCGTAATAATGACTAAATCTGAGCAGCAA GCCGATTCA; SEQ ID NO: 15) and CI-017 (ATGATGATGATGATGATGACCTCGTAAGTAGCTC AGTAA; SEQ ID NO: 9) to produce all of the CYS4 gene without the stop codon and transcription terminator. CI-029 (SEQ ID NO: 15) primer contains the last 13 bases of the ADH2 promoter region cloned in addition to the first ten codons of CYS4 gene. Primer CI-017 (SEQ ID NO: 9) has the sequence for the last six codons of CYS4 gene, except the stop codon plus a glycyl residue and six histadyl residues. The resulting PCR product comprises the CYS4 coding region, and a further coding sequence for glycine and six histidine residues. The glycine was added to increase the spatial flexibility of the poly-his peptide after translation. The "terminator" fragment was produced by amplifying the same genomic DNA with primers CI-018 (CATCATCATCATCATCATTAAATAAG AACCCACGCT; SEQ ID NO: 10) and CI-040 (AGGGCTCGAGGATCCCGGGGGT GCTATTATGAATGCACGG; SEQ ID NO: 16) to produce a poly-histidine sequence with a TAA stop codon, followed by the transcription terminator. The CI-029/CI-017 PCR reaction produced an approximately 1530 bp fragment while CI-018/CI-040 reaction produced an approximately 331 bp fragment. These two fragments were joined by mixing their PCR products and amplifying with primers CI-029/CI-040. The resulting product was designated CYS4H and was approximately 1861 bp in length.

To join the ADH2 promoter to the CYS4H gene fragment, a PCR product was first generated with primer CI-027 (CGGGGATCCGACGTTTTGCCCGCAGGCG GGAAACC; SEQ ID NO: 17)and primer CI-028 (AGATTTAGTCATTATTACGATAT AGTTAATAGT-TGATAG; SEQ ID NO: 18) from the same yeast genomic DNA to produce the ADH2 promoter sequence. Primer CI-028 (SEQ ID NO: 18) contains the first 12 nucleotides of the coding region of CYS4 gene. Therefore, between primers CI-028 (SEQ ID NO: 18) and CI-029 (SEQ ID NO: 15) there are 25 nucleotides of complimentarily DNA in their respective products. The ADH2 PCR product was mixed with CYS4H fragment and amplified with primers CI-027 (SEQ ID NO: 17) and CI-040 (SEQ ID NO: 16), to produce a product fragment of approximately 2201 bp designated ADH2CYS4H. Each of these PCR products was confirmed by restriction endonuclease analysis.

The ADH2CYS4H product was cloned into YEp24 by cutting both DNA with BamHI and ligating using T4 DNA ligase. Ligated products were transformed into *E. coli* (TOP10; Invitrogen) cells and plated on LB-agar plus ampicillin plates. Plasmids, prepared using Plasmid Preparation kit (Roche) according to the manufacture's recommendation from putative recombinants, were analyzed by restriction endonuclease. The plasmids from clones found to have the correct insert were transformed into *S. cerevisiae* (BJ5460) and plated on synthetic complete medium minus uracil (SC-ura), supplemented with 2% glucose. After two days putative recombinants were re-streaked on the same type of plates to isolate colonies. The cells are induced by growing in SC-ura plus 2% ethanol and 1% peptone, usually supplemented with 0.1% glucose to enable the cells to grow within 24 hours. Following overnight growth cells were are collected by centrifugation and the cell pellet was saved at $-70°$ C. until lysis. Cells were lysed by resuspending the cell pellet in 0.05 volume of the original volume in lysis buffer. Glass beads were then added to the meniscus of the buffer.

The whole suspension was vortex for 1 min each for four times. Cells were cooled on ice for 1 min between vortexing. Lysate was transferred to fresh tube and centrifuged for 10 min at 10,000×g. The cleared lysate was layered onto a His-Resin column (Roche) and the protein was purified according to manufacture's recommendation. A partially purified protein was recovered in elution three.

EXAMPLE 5

Examples of Non-Cycling Portion of Assay Formats for Homocysteine

In this example the non-cycling portion of the assay for pyruvate and cystathionine are demonstrated.

Pyruvate Assay

Pyruvate: The present invention provides for the measurement of homocysteine based on the use of the enzymes CBS and CBL to cycle homocysteine with the production of pyruvate and ammonia. The rate of pyruvate and ammonia production was predicted to be proportional to the original homocysteine concentration in the sample. Measurement of this rate using appropriate enzyme(s) presents an opportunity for a homogeneous homocysteine method.

In one aspect of the present invention a highly sensitive method for pyruvate quantitation has been developed. In the method pyruvate oxidase converts pyruvate to acetyl phosphate, carbon dioxide and peroxide. Peroxidase subsequently converts the peroxide, TOOS, and 4-aminoantipyrine to a chromogen, which exhibits an absorption maximum near 550 nm. The molar absorptivity of this chromogen is quite high, about 36 L mol-1 cm-1.

Figure 2:
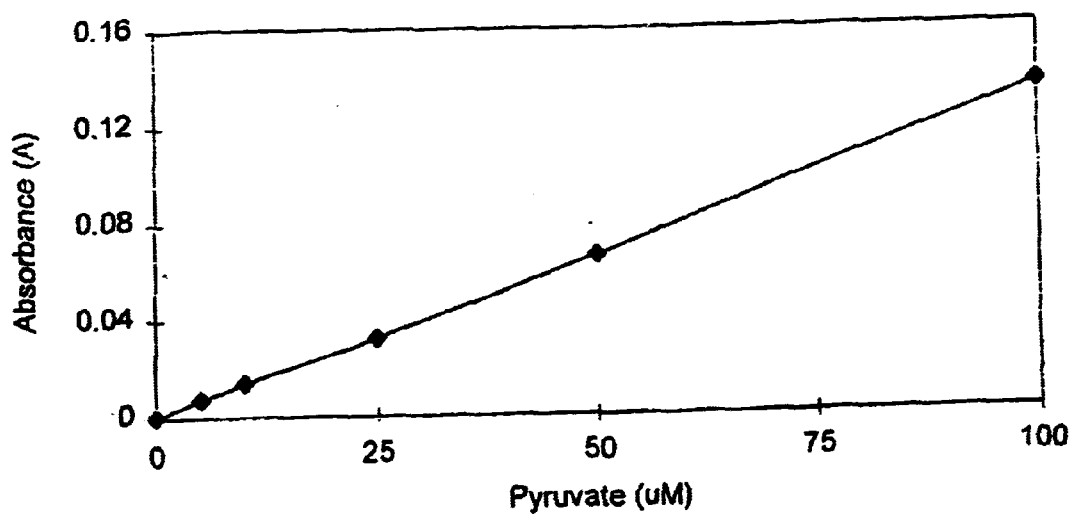
FIG. 2 depicts a standard curve of absorbance values plotted versus known quantities of pyruvate (0–100 μM). Assay time was 5 min.

Using reagent components shown in Table 1 and the Cobas FARA (Roche, Basel, Switzerland) instrument parameters listed in Table 2, pyruvate was easily measured in the $\mu$M range by an early-read blank and endpoint reaction in about 5–10 minutes. Absorbance versus time plots for aqueous calibrators are shown in FIG. 1. An actual calibration curve is shown in FIG. 2.

TABLE 1

Pyruvate Method: Reagent Components

| Chemical | Concentration |
|---|---|
| Reagent 1 | |
| HEPES, hemisodium salt | 21.5 mM |
| HEPES, Acid | 28.6 mM |
| EDTA (4Na) | 5.0 mM |
| Mg $SO_4$.7H2O | 49.8 mM |
| $K_2HPO_4$, dibasic | 7.5 mM |
| TOOS | 1.4 mM |
| TTHA | 0.8 mM |
| TPP | 0.2 mM |
| 4-aminoantipyrine | 1.0 mM |
| BSA | 1.9 g/L |
| Potassium ferrocyanide | 0.07 mM |
| Peroxidase, horseradish | 3.0 KU/L |
| Pyruvate Oxidase | 3.0 KU/L |
| pH = 7.0 | |

TABLE 2

Pyruvate Method: Cobas FARA parameters

| Parameter | Setting |
|---|---|
| GENERAL | |
| measurement mode | ABS |
| reaction mode | P-A |
| Calibration mode | SLOPE AVG |
| reagent blank | REAG/DIL |
| Wavelength | 550 nm |
| Temperature | 37° C. |
| ANALYSIS | |
| sample volume | 40 $\mu$L |
| diluent volume | 10 $\mu$L |
| diluent name | $H_2O$ |
| Reagent volume | 250 $\mu$L |
| incubation time | 60 s |
| start reagent volume | na |
| diluent name | $H_2O$ |
| diluent volume | na |
| incubation time | na |
| start reagent 2 volume | na |
| diluent name | $H_2O$ |
| diluent volume | na |
| Temperature delay | na |
| ABSORBANCE READINGS | |
| First | 0.5 sec |
| Number | 14 |
| Interval | 30 sec |
| CALCULATION | |
| Number of steps | 1 |
| calculation step A | KINETIC |
| First | 1 |
| Last | 14 |
| CALIBRATION | |
| Number of stds | 1 |
| STD1 | 50 $\mu$M |
| Replicate | 2 |

Cystathionine Assay

Figure 3:
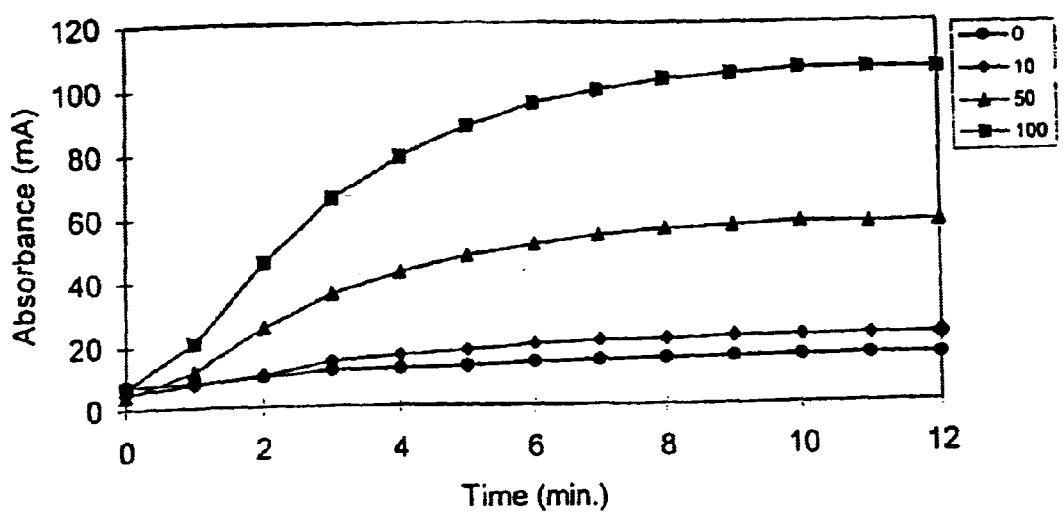
FIG. 3 depicts absorbance versus time plots obtained using aqueous solutions of cystathionine (0–100 μM). Cystathionine was measured by the enzymic conversion of cystathionine to homocysteine, pyruvate and ammonia by CBL.

Cystathionine was measured by adding CBL to the pyruvate reagent described above. CBL converts cystathionine to homocysteine, pyruvate and ammonia. The pyruvate was then measured as described above. The composition of the reagent used to measure cystathionine is shown in Table 3. The measurement can be made using any suitable instrument. In the present example a Cobas FARA (Roche, Basel, Switzerland) was used. Typical reaction parameters are shown in Table 4. FIG. 3 depicts absorbance vs. time plots obtained using aqueous solutions of cystathionine. The reaction reaches endpoint in less than ten minutes.

TABLE 3

Cystathionine Method: Reagent Components

| Chemical | Concentration |
| --- | --- |
| Reagent 1 | |
| HEPES, hemisodium salt | 20.3 mM |
| HEPES, Acid | 27.0 mM |
| EDTA (4Na) | 4.7 mM |
| Mg SO4.7H2O | 47.1 mM |
| K2HPO4, dibasic | 7.1 mM |
| TOOS | 1.3 mM |
| TTHA | 0.8 mM |
| TPP | 0.2 mM |
| 4-aminoantipyrine | 0.9 mM |
| BSA | 1.8 g/L |
| Potassium ferrocyanide | 0.07 mM |
| Peroxidase, horseradish | 2.8 KU/L |
| Pyruvate Oxidase | 2.8 KU/L |
| CBL | 1.9 g/L |
| pH = 7.0 | |

TABLE 4

Cystathione Method: Cobas FARA parameters

| Parameter | Setting |
| --- | --- |
| GENERAL | |
| measurement mode | ABS |
| reaction mode | P-A |
| calibration mode | LIN INTER |
| reagent blank | REAG/DIL |
| wavelength | 550 nm |
| temperature | 37° C. |
| ANALYSIS | |
| sample volume | 30 µl |
| diluent volume | 10 µl |
| diluent name | H₂O |
| reagent volume | 260 µl |
| incubation time | 60 sec |
| start reagent volume | na |
| diluent name | H₂O |
| diluent volume | na |
| incubation time | na |
| start reagent 2 volume | na |
| diluent name | H₂O |
| diluent volume | na |
| temperature delay | na |
| ABSORBANCE READINGS | |
| first | 5 sec |
| number | 21 |
| interval | 60 sec |
| CALCULATION | |
| number of steps | 1 |
| calculation step A | ENDPOINT |

TABLE 4-continued

Cystathione Method: Cobas FARA parameters

| Parameter | Setting |
| --- | --- |
| first | 1 |
| last | 10 |
| CALIBRATION | |
| number of stds | 1 |
| STD1 | 50 µM |
| replicate | 2 |

Figure 4:
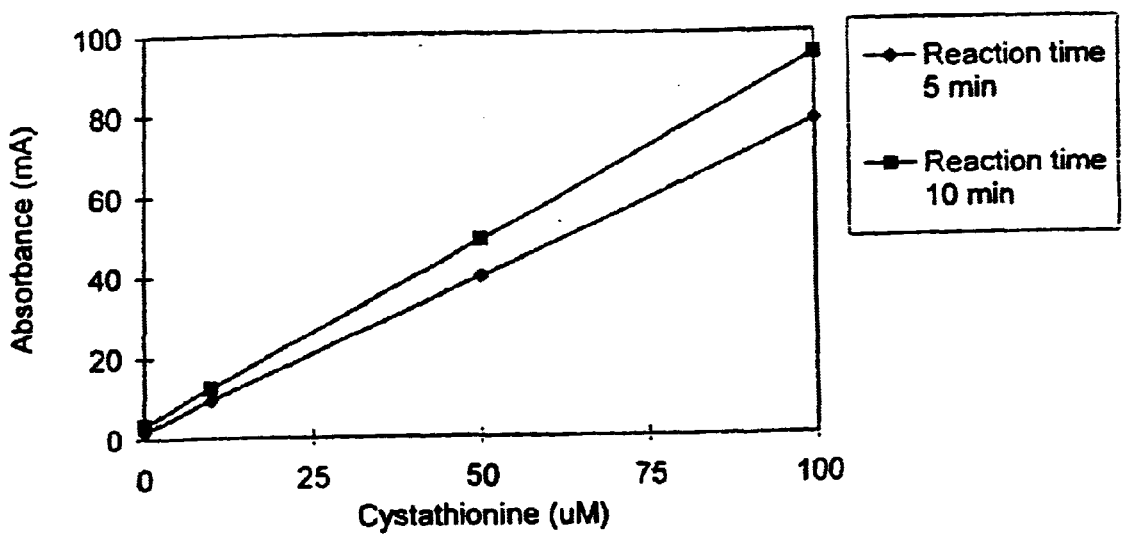
FIG. 4 depicts cystathionine assay standard curves obtained using aqueous solutions of cystathionine (0 to 100 μM). Reaction time was either 5 or 20 min.

FIG. 4 depicts standard curves obtained using aqueous solutions of cystathionine. These curves are linear over at least the cystathionine concentration range of 0–100 µM. The chromophore formed was stable over approximately 15–20 minutes. However, if samples containing 10–20 fold higher cystathionine concentrations were assayed, some instability of the chromophore was evident.

In some experiments serine was included in the reaction mixture. Serine at a level of 250 µM exhibited no significant effect. Higher levels of serine were also tolerated by this assay. The non-interference of serine is an important observation because the presence of serine is necessary for the assay of homocysteine.

EXAMPLE 6

Enzyme Cycling Assays for Homocysteine

In this example the enzyme cycling systems for determining the concentration of homocysteine are provided using either pyruvate oxidase/peroxidase signaling system or lactate dehydrogenase signaling system.

Demonstration of Cycling: CBS/CBL/PO/HRP Enzyme Cycling System

Figure 5:
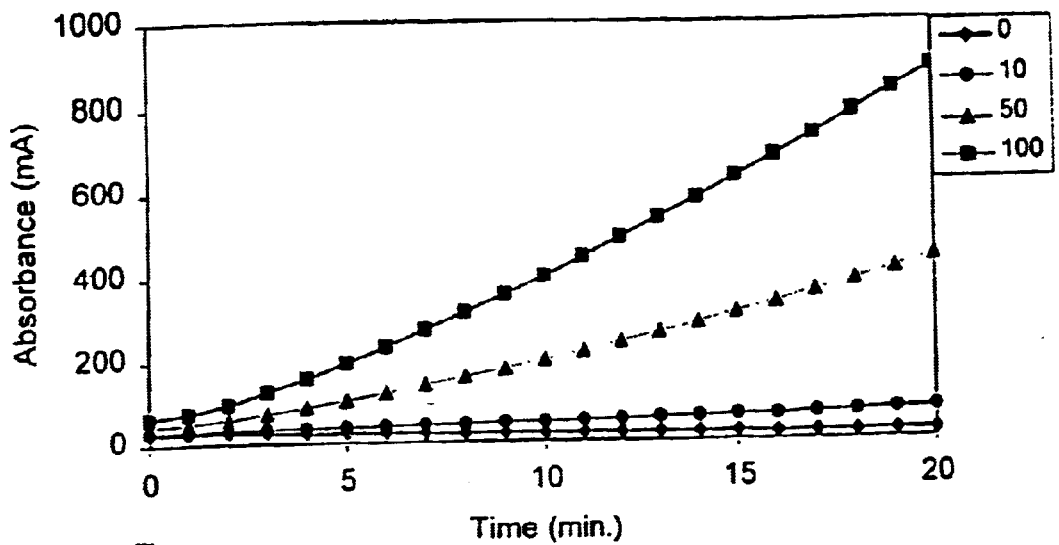
FIG. 5 depicts absorbance versus time plots demonstrating the CBS/CBL/pyruvate oxidase/peroxidase cycling and signaling system. Cystathionine was dissolved in water to prepare standards at concentrations between 1 and 100 μM.
Figure 6:
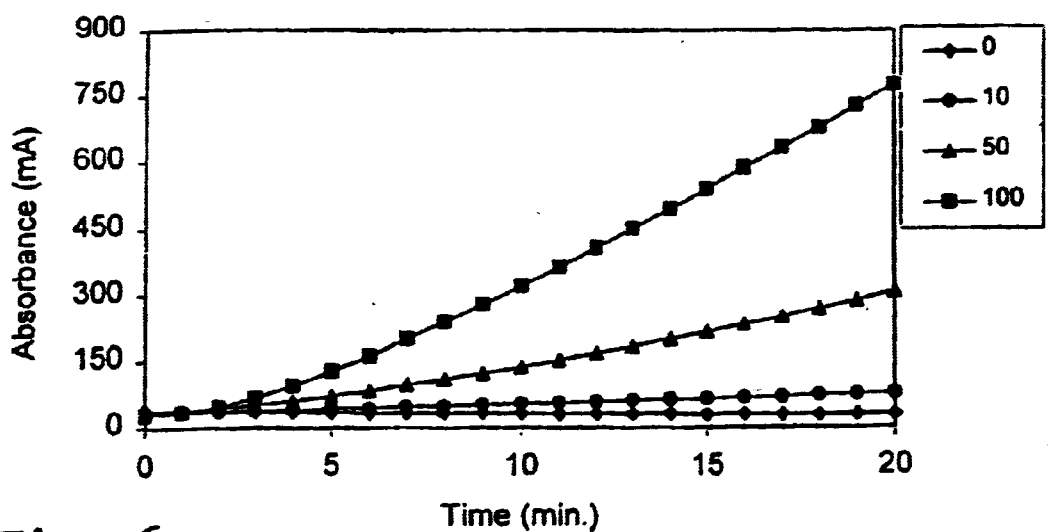
FIG. 6 depicts absorbance versus time plots demonstrating the CBS/CBL/pyruvate oxidase/peroxidase cycling and signaling system. Homocysteine was dissolved in water to prepare standards at concentrations between 0 and 100 μM.
Figure 7:
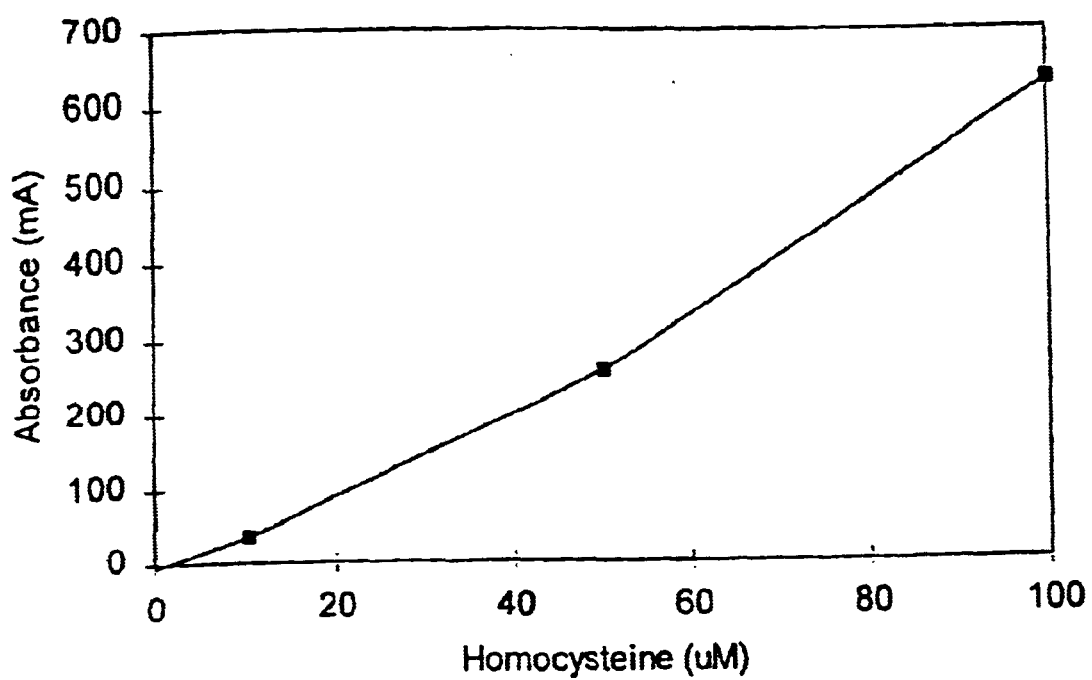
FIG. 7 depicts a typical calibration curve obtained using aqueous solutions of homocysteine (0–100 μM) using the CBS/CBL/PO/HRP cycling and detection system.

The cycling system has been demonstrated wherein the reaction was initiated using either homocysteine or cystathionine. The reagent components used in these experiments are shown in Table 5. CBS and serine were added separately following mixing of the sample with reagent 1 which contains all other components. Pertinent Cobas FARA parameters are shown in Table 6. Cystathionine or homocysteine was dissolved in water to prepare standards at appropriate concentrations. Time versus absorbance plots are shown in FIGS. 5 and 6. After a lag time of three to six minutes the plots are linear. A typical homocysteine calibration curve (FIG. 7) which, while not completely linear, can be used to quantify homocysteine concentrations in suitable specimens using an appropriate curve-fitting technique.

TABLE 5

CBS/CBL Cycling, PO/HPR Method

| Reagent Components Chemical | Concentration |
| --- | --- |
| Reagent 1 | |
| HEPES, hemisodium salt | 20.3 mM |
| HEPES, Acid | 27.0 mM |
| EDTA(4Na) | 4.7 mM |
| MgSO₄.7H2O | 47.1 mM |
| K₂HPO₄, dibasic | 7.1 mM |
| TOOS | 1.3 mM |
| TTHA | 0.8 mM |
| TPP | 0.2 mM |

TABLE 5-continued

CBS/CBL Cycling,
PO/HPR Method

| Reagent Components Chemical | Concentration |
|---|---|
| 4-aminoantipyrine | 0.9 mM |
| BSA | 1.8 g/L |
| Potassium ferrocyanide | 0.07 mM |
| Peroxidase, horseradish | 3.0 KU/L |
| Pyruvate Oxidase | 3.0 KU/L |
| CBL | |
| pH = 7.0 | |
| Reagent SR1 | |
| Serine | 3.1 mM |
| Reagent SR2 | |
| CBS | 1.23 g/L |

TABLE 6

CBS/CBL/PO/HPR cycling system:
Cobas FARA parameters

| Parameter | Setting |
|---|---|
| GENERAL | |
| measurement mode | ABS |
| reaction mode | P-I-SR1-I-SR2-A |
| Calibration mode | LIN INTER |
| reagent blank | REAG/DIL |
| Wavelength | 550 nm |
| Temperature | 37° C. |
| ANALYSIS | |
| sample volume | 30 μl |
| diluent volume | 10 μl |
| diluent name | H$_2$O |
| reagent volume | 260 μl |
| Incubation time | 60 sec |
| start reagent volume | 30 μl (serine) |
| diluent name | H$_2$O |
| diluent volume | 5 μl |
| Incubation time | 10 sec |
| start reagent 2 volume | 30 μl (CBS) |
| diluent name | H$_2$O |
| diluent volume | 5 μl |
| temperature delay | na |
| ABSORBANCE READINGS | |
| First | 0.5 sec |
| Number | 14 |
| Interval | 30 sec |
| CALCULATION | |
| number of steps | 1 |
| Calculation step A | ENDPOINT or KINETIC |
| First | 1 |
| Last | 14 |
| CALIBRATION | |
| number of stds | 1 |
| STD1 | 50 μM |
| Replicate | 2 |

Reduction of Disulfide Bonds

Very little homocysteine is present in the reduced, non-disulfide bonded state in human plasma. Most homocysteine is coupled to proteins or small molecules through disulfide bonds. Disulfide reduction of these compounds is necessary to liberate homocysteine for measurement by any method for total homocysteine determination. This example demonstrates that use of a reducing agent is compatible with a system using lactate dehydrogenase and NADH. Potential candidate reducing agents include DTE, DTT, n-acetylcysteine, thioglycolic acid, TCEP and the like. For use of these compounds in the method of the present invention, precise adjustment of reducing agent concentration and instrument parameters are necessary. Early indications that certain reducing agents could hinder the action of pyruvate oxidase and or horseradish peroxidase led to the investigation of the alternative pyruvate detection system described below.

Demonstration of Cycling: CBS/CBL/LDH System

Pyruvate reacts with NADH in the presence of the enzyme lactate dehydrogenase to produce lactic acid and NAD. Pyruvate can be quantified by measuring the absorbance decrease at 340 nm. The molar absorptivity of NADH is about six-fold less than that of the peroxidase generated chromogen. However, this does not effect the system of the present invention because CBL/CBS homocysteine cycling is able to generate relatively large amounts of pyruvate.

The reagent system used to generate the data presented in FIGS. 8, 9, 10, & 11 comprises serine, CBL and lactate dehydrogenase in HEPES buffer (pH 7.2) as the first reagent. NADH in TRIS buffer (pH 8.5) and CBS are then added in sequence. All of the components can, however, be combined differently to form either a two or three reagent homocysteine measurement system. Reagent concentrations are shown in Table 7, and Cobas FARA parameters are shown in Table 8. The NADH concentration was adjusted to provide sufficient linearity while allowing for plasma sample absorption at 340 nm.

TABLE 7

| CBS/CBL/LDH CYCLING SYSTEM: Reagent Components | |
|---|---|
| Chemical | Concentration |
| Reagent 1 | |
| HEPES, hemisodium salt | 39.4 mM |
| HEPES, acid | 12.6 mM |
| Serine | 0.72 mM |
| Lactate dehydrogenase | 33,000 U/L |
| CBL | 6.05 ug/L |
| pH = 7.2 | |
| Reagent SR1 | |
| NADH | 4.16 mM |
| TRIS | 50 mM |
| pH = 8.5 | |
| Reagent SR2 | |
| CBS | 996 mg/L |
| TRIS | 50 mM |
| Sodium Chloride | 100 mM |
| pyridoxal phosphate | 5 uM |
| Sample Diluent | |
| DTT | 13 mM |
| HEPES, hemisodium salt | 56.7 mM |
| HEPES, Acid | 18.1 mM |
| pH = 7.2 | |

TABLE 8

CBS/CBL/LDH cycling system: Cobas FARA parameters

| Parameter | Setting |
|---|---|
| GENERAL | |
| measurement mode | ABS |
| reaction mode | P-T-I-SR1-I-SR2-A |
| calibration mode | LIN INTER |
| reagent blank | REAG/DIL |
| Wavelength | 340 nm |
| temperature | 37° C. |
| ANALYSIS | |
| sample volume | 30 µl |
| diluent volume | 10 µl |
| diluent name | H$_2$O (or reducing agent) |
| reagent volume | 250 µl |
| incubation time | 60 sec |
| start reagent volume | 15 µl (NADH) |
| diluent name | H$_2$O |
| diluent volume | 5 µl |
| incubation time | 10 sec |
| start reagent 2 volume | 30 µl (CBS) |
| diluent name | H$_2$O |
| diluent volume | 10 µl |
| temperature delay | NA |
| ABSORBANCE READINGS | |
| First | 5 sec |
| Number | 16 |
| Interval | 30 sec |
| CALCULATION | |
| Number of steps | 1 |
| calculation step A | ENDPOINT or KINETIC |
| First | 6 |
| Last | 20 |
| CALIBRATION | |
| Number of stds | 1 |
| STD1 | 25 or 50 µM |
| Replicate | 2 |

Analysis of Aqueous Solutions

Figure 8:
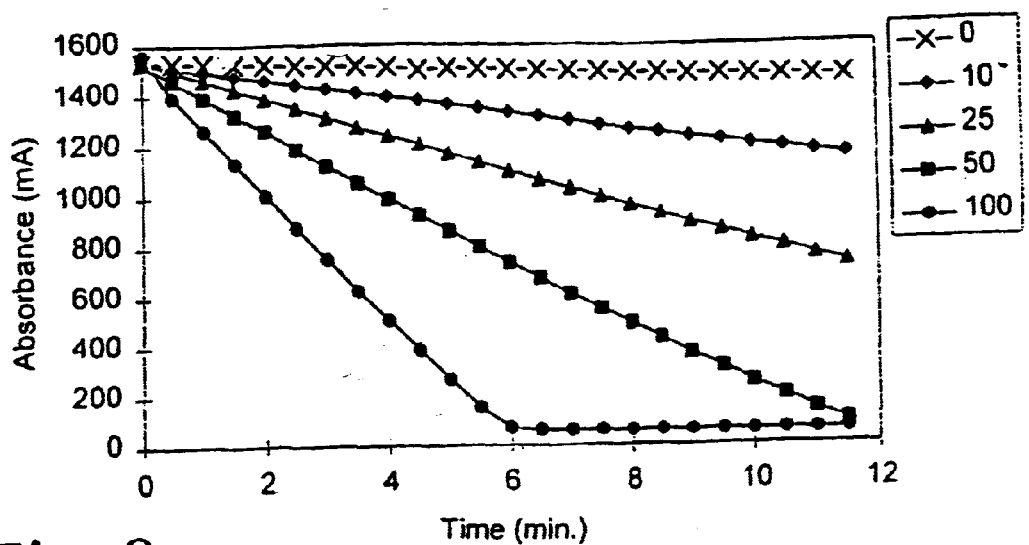
FIG. 8 depicts typical absorption versus time plots obtained using homocysteine (0–100 μM) in aqueous solution using the CBS/CBL/LDH system without dithiotreitol.
Figure 9:
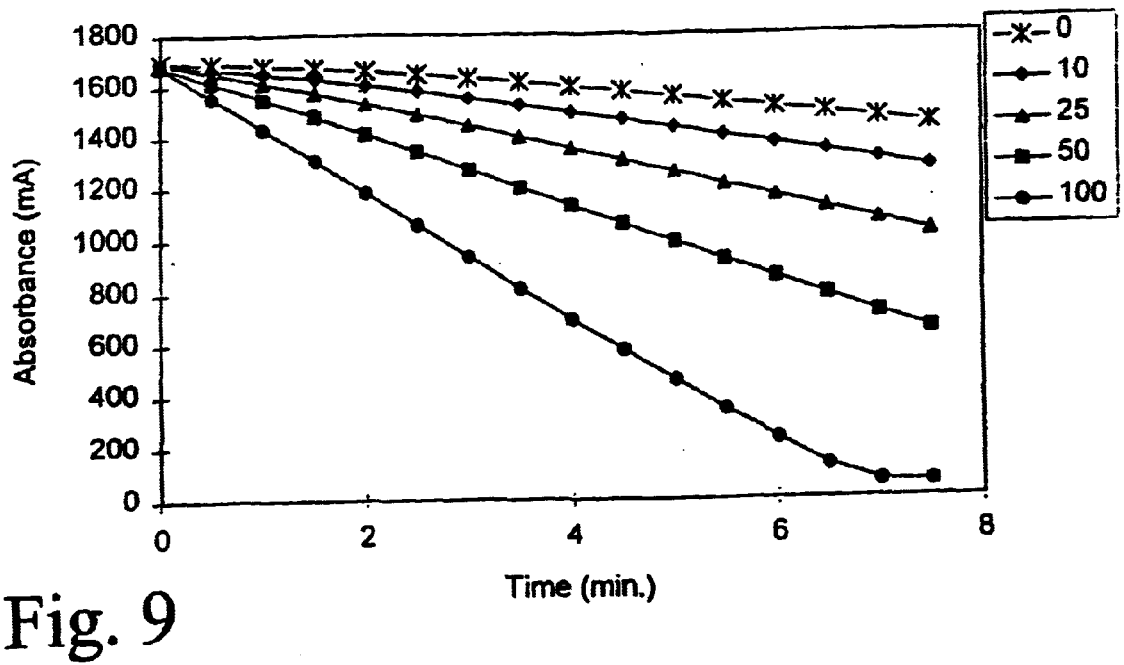
FIG. 9 depicts typical absorption versus time plots obtained using homocysteine (0–100 μM) in aqueous solution using the CBS/CBL/LDH cycling system with dithiotreitol.
Figure 10:
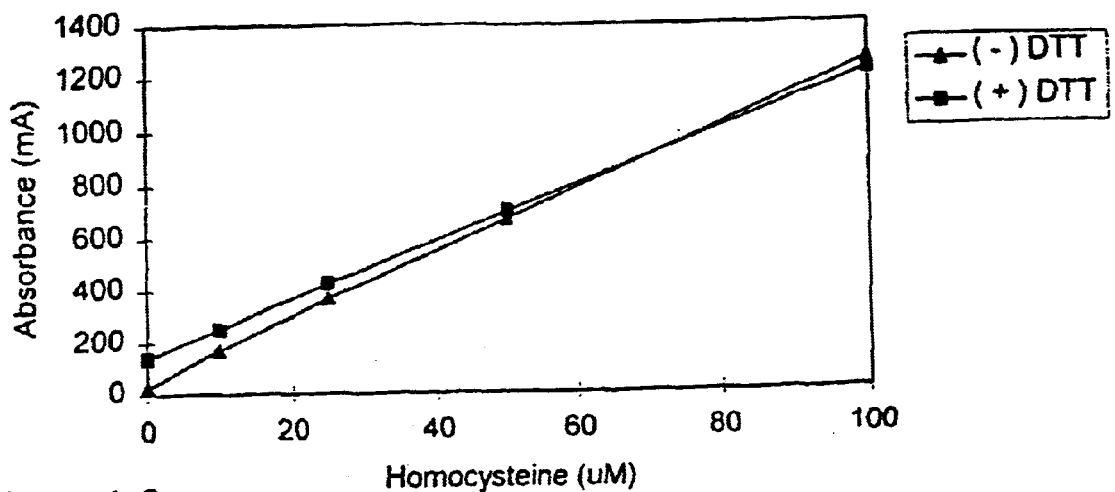
FIG. 10 depicts a calibration plot of homocysteine concentration (0 to 100 μM) versus absorbance with and without dithiotreitol. Reaction time was 5 minutes.

The system performed well for the detection of homocysteine in aqueous solution. Typical absorption versus time plots are shown in FIGS. 8 and 9. These plots were linear with little or no apparent lag phase. Rates of NADH disappearance were relatively high. Moreover, the calibration plot of homocysteine concentration versus absorbance was linear over the range of 0–100 µM in the sample (FIG. 10). Thus, only one calibrator, e.g. 25 µM, together with a reagent blank was necessary for calibration.

Homocysteine solutions were prepared at various concentrations to demonstrate performance of the method over a homocysteine concentration range of 2–20 µM. Results are shown in Table 9 both in the presence and absence of DTT. As mentioned above, DTT serves to reduce disulfide bonds in samples (eg serum, plasma, etc.). DTT does not significantly interfere with the lactate dehydrogenase catalyzed reaction.

TABLE 9

Demonstration of Linearity: CBS/CBL/LDH cycling system

| | Reaction time = 3 min. Observed value (uM) | |
|---|---|---|
| Homocysteine conc. (uM) | (−) DTT | (+) DTT |
| 2 | 2 | 1.2 |
| 5 | 5.2 | 4.3 |
| 8 | 8.2 | 7.4 |
| 10 | 10.4 | 9.9 |
| 12.5 | 12.7 | 12.5 |
| 16.7 | 16.8 | 16.3 |
| 20 | 20.5 | 20 |

Analysis of Human Plasma Based Control Products

Accurate performance of the CBS/CBL/LDH cycling system has been demonstrated herein using human plasma based homocysteine control products manufactured by the Bio-Rad Co. Various concentrations of DTT have been used, and incubation times have been varied in order to achieve optimum homocysteine recovery. Incubation times of 5–15 min with DTT concentrations of 1.6–3.2 mM gave homocysteine measurements well within the ranges specified for various other methods.

Human Plasma Samples

Figure 11:
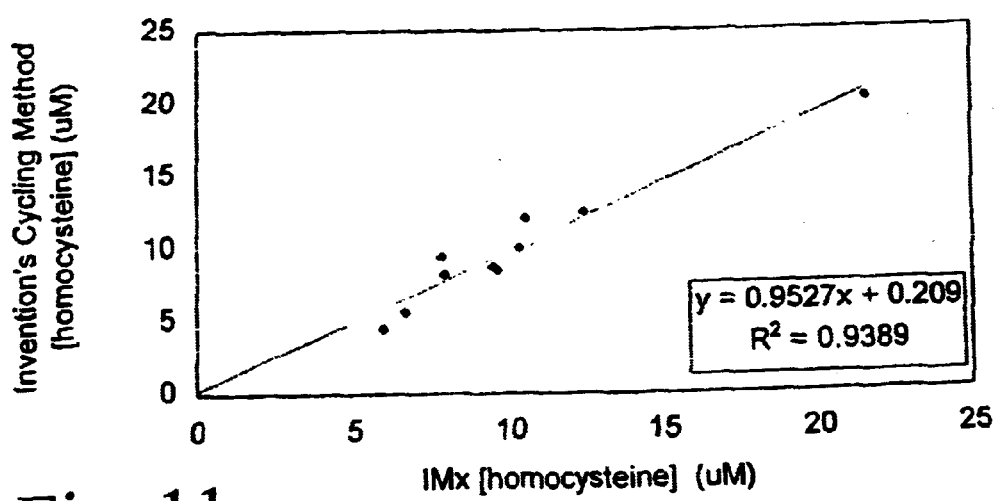
FIG. 11 depicts a correlation between the quantitation results obtained using the CBS/CBL/LDH enzyme cycling system to measure homocysteine in human plasma samples using DTT as the reducing agent compared with quantitation results obtained by the Abbott IMx homocysteine method.

The homocysteine cycling assay has demonstrated good performance using human plasma samples with DTT as the reducing agent. Results agree well with those obtained by an independent laboratory using the Abbott IMx homocysteine method (FIG. 11). Cobas FARA parameters used in this experiment are shown in Table 10 and reagent components are shown in Table 7. In this assay an aqueous homocysteine calibrator (25 uM) was used. Absorbance vs. time plots for aqueous based samples were linear in the absence of DTT and nearly linear in the presence of DTT. However, plots obtained using plasma samples were different, i.e., not linear after the first three minutes. Under the conditions outlined in Table 7 and Table 10, cycling appears to gradually slow down over time. Nevertheless, the correlation study presented in FIG. 11 demonstrates relatively close agreement between the present method (outlined in Table 7 and Table 10) with those obtained by IMx when testing human serum samples.

TABLE 10

CBS/CBL/LDH cycling system: Cobas FARA parameters for human plasma correlation study

| Parameter | Setting |
|---|---|
| GENERAL | |
| measurement mode | ABS |
| reaction mode | P-T-I-SR1-I-SR2-A |
| Calibration mode | LIN INTER |
| reagent blank | REAG/DIL |
| Wavelength | 340 nm |
| Temperature | 37° C. |
| ANALYSIS | |
| sample volume | 30 µl |
| diluent volume | 10 µl |
| diluent name | H$_2$O (or reducing agent) |
| Temperature delay | 900 sec |
| reagent volume | 250 µl |
| Incubation time | 60 sec |
| start reagent volume | 15 µl (NADH) |

TABLE 10-continued

CBS/CBL/LDH cycling system: Cobas FARA parameters for human plasma correlation study

| Parameter | Setting |
|---|---|
| diluent name | H₂O |
| diluent volume | 5 µl |
| Incubation time | 10 sec |
| start reagent 2 volume | 30 µl (CBS) |
| diluent name | H₂O |
| diluent volume | 10 µl |
| Temperature delay | NA |
| ABSORBANCE READINGS | |
| First | 5 sec |
| Number | 24 |
| Interval | 30 sec |
| CALCULATION | |
| number of steps | 1 |
| Calculation step A | ENDPOINT or KINETIC |
| First | 1 |
| Last | 6 |
| CALIBRATION | |
| number of stds | 1 |
| STD1 | 25 or 50 µM |
| Replicate | 2 |

In a preferred embodiment, the rates were measured in the first three minutes after reaction initiation. Additional optimization of the system, including variation in salt and detergent concentrations, will likely result in more consistent performance with aqueous and plasma samples. The assay has been equally accurate when components were combined into two or three mixtures of reagents.

EXAMPLE 7

Comparison of Homocysteine Assays

In this example, a preferred homocysteine assay in accordance with the invention was tested and compared with two existing assays, namely a conventional HPLC technique and the commercially available IMx assay.

The assay of the invention was carried out using three reagents as shown in Table 11. The first reagent R1 was initially in the form of powder and was reconstituted to a level of 1.5 g powder per 100 mL water. The overall assay kit also included calibrators containing L-cystathionine spiked at various levels in a human plasma matrix, as well as two control samples made up in a processed human plasma matrix.

TABLE 11

CBS/CBL/LDH CYCLING SYSTEM: Reagent Components

| Chemical | Concentration | |
|---|---|---|
| Reagent 1 | | |
| HEPES, hemisodium salt | 43.3 | mM |
| Hepes, acid | 12.7 | mM |
| Serine | 1.295 | mM |
| Lactate dehydrogenase | >800 | U/L |
| NADH | 1.06 | mM |
| Triton X-100 | 0.05% | v/v |
| Sodium azide | 7.7 | mM |
| pH = 8.0 | | |

TABLE 11-continued

CBS/CBL/LDH CYCLING SYSTEM: Reagent Components

| Chemical | Concentration | |
|---|---|---|
| Reagent SR1 | | |
| DTE | 6.75 | mM |
| Citric acid | 20 | mM |
| pH = 2.0 | | |
| Reagent SR2 | | |
| CBS | 18.7 | KU/L |
| CBL | 8.9 | KU/L |
| Sorbitol | 1.65 | M |
| Sodium chloride | 100 | mM |
| Pyrdoxal phosphate | 5 | uM |
| Sodium azide | 7.7 | mM |
| TRIS/HCl | 50 | mM |
| pH = 8.0 | | |

TABLE 12

CBS/CBL/LDH Cycling System: Cobas MIRA Parameters

| Parameter | Setting |
|---|---|
| GENERAL | |
| Measurement Mode | Absorb |
| Reaction Mode | R-S-SR1-SR2 |
| Calibration Mode | Lin Regre |
| Reagent Blank | Reag/Dil |
| Cleaner | No |
| Wavelength | 340 nm |
| Decimal Position | 2 |
| Unit | umol/L |
| ANALYSIS | |
| Post Dil. Factor | No |
| Conc. Factor | No |
| Sample cycle | 1 |
| volume | 30.0 uL |
| Diluent name | H2O |
| volume | 25.0 uL |
| Reagent cycle | 1 |
| volume | 90 uL |
| Start R1 cycle | 2 |
| volume | 25 ul |
| Diluent name | H2O |
| volume | 25 uL |
| Start R2 cycle | 17 |
| volume | 35 uL |
| Diuent name | H2O |
| volume | 15 uL |
| CALCULATION | |
| Sample Limit | No |
| Reac. Direction | Decrease |
| Check | Off |
| Antigen Excess | No |
| Covers. Factor | 1.00 |
| Offset | 0.00 |
| Test range Low | On |
| High | On |
| Normal range Low | No |
| High | No |
| Number of Steps | 1 |
| Calc. Step A | Kinetic |
| Readings First | 18 |
| Last | 32 |
| Reaction Limit | No |
| CALIBRATION | |
| Calib. Interval | Each Run |
| Blank Reag. | No |
| Range Low | |

TABLE 12-continued

CBS/CBL/LDH Cycling System: Cobas MIRA Parameters

| Parameter | Setting |
|---|---|
| High | No |
| Blank Range Low | No |
| High | No |
| Standard Position | 1 |
| 1 | 3.5 umol/L |
| 2 | 7.0 umol/L |
| 3 | 17 umol/L |
| 4 | 27 umol/L |
| 5 | 47 umol/L |
| 6 | No |
| 7 | No |
| Replicate | Single |
| Deviation | |
| Correction Std. | No |
| Control | |
| CS1 position | No |
| CS2 position | No |
| CS3 position | No |

In performing this assay, the commercially available Cobas MIRA instrument was used. The Cobas MIRA software allows for 50 programable, 25 second cycles. In particular, the instrument was programmed according to the parameters in Table 12. In cycle 1, 30 μL of the sample was added to a cuvette, followed by 25 μL of flush water and 90 μL of liquid reagent R1. At the beginning of cycle 2, 25 μL of reagent SR1 was added with an additional 25 μL of flush water. Thereupon, the mixture was allowed to incubate for 15 cycles (6.25 min.) to allow the reductant to liberate any bound homocysteine and to destroy any endogenous pyruvate present. At this point, 35 μL of the CBS/CBL enzyme reagent was added with an additional 15 μL of flush water. The decrease in absorbance at 340 nm was measured over time between cycles 18 and 32 as a measure of homocysteine in the sample. The total assay time between sample addition and the final absorbance reading was 32 cycles, or 13 min. and 20 sec. Since multiple samples are run in parallel, additional sample results are produced by the MIRA at a rate of approximately one every 30–90 seconds depending on the length of the run and the number of instrument calibrators used. Using similar programming parameters, this assay may be adapted to even faster instruments (eg. Roche INTEGRA, Hitachi, ACE, etc) which could yield even greater throughput rates.

Figure 12:
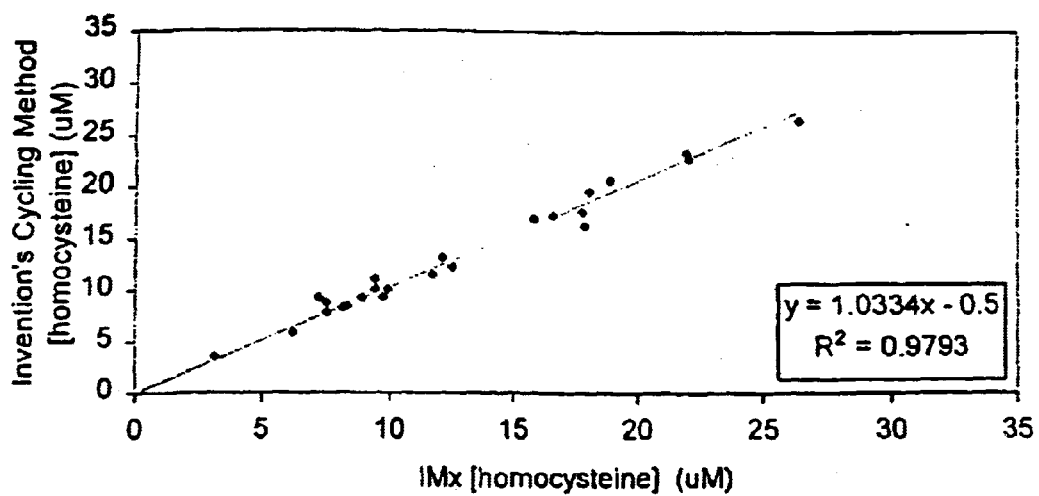
FIG. 12 depicts a correlation graph illustrating the correlation between the assay of the present invention (y) versus the commercially available IMx assay (x), as described in Example 7.
Figure 13:
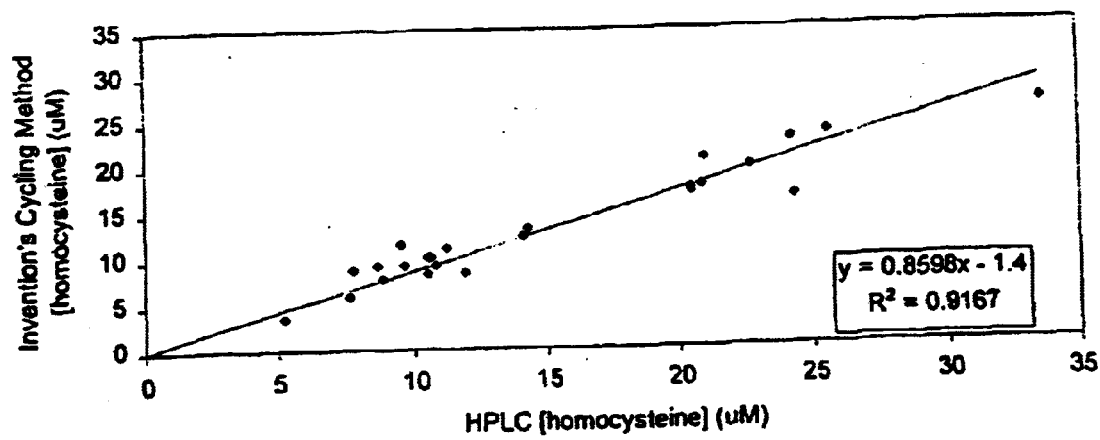
FIG. 13 depicts a correlation graph illustrating the correlation between the assay of the present invention (y) versus a conventional HPLC assay (x), as described in Example 7.
Figure 14:
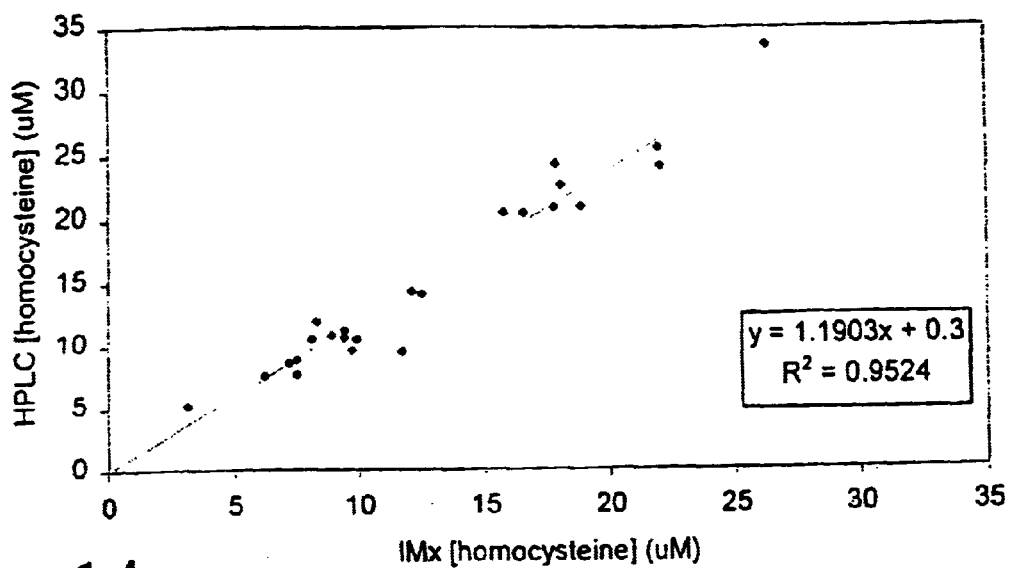
FIG. 14 depicts a correlation graph illustrating the correlation between the IMx assay (x) and the HPLC assay (y), as described in Example 7.

A total of 24 samples were tested using the assay of the invention and the comparative known assays. Table 13 below sets forth the homocysteine concentrations obtained using these three methods. FIGS. 12–14 are respective correlation graphs depicting graphically the results of Table 13. As can be seen, the method of the invention correlates closely with both IMx and HPLC; with closer agreement typically seen with IMx. However, the present method is substantially less expensive, can be run faster, and can be performed using generally available chemical analyzers.

The invention exhibits very good between-run precision as shown in Table 14. Typical within-run CV's were found to be less than 4% over homocysteine concentrations of about 7–20 μmol/L.

TABLE 13

Comparison of Homocysteine Assays

| | Homocysteine Concentration [μM] | | |
|---|---|---|---|
| Sample # | HPLC | Invention | IMx |
| 1 | 9.5 | 11.5 | 11.7 |
| 2 | 14.3 | 13.1 | 12.1 |
| 3 | 8.8 | 7.8 | 7.5 |
| 4 | 10.6 | 10.1 | 9.4 |
| 5 | 10.5 | 10.1 | 9.9 |
| 6 | 8.6 | 9.2 | 7.2 |
| 7 | 7.6 | 5.8 | 6.2 |
| 8 | 5.2 | 3.5 | 3.1 |
| 9 | 9.6 | 9.3 | 9.7 |
| 10 | 7.7 | 8.7 | 7.5 |
| 11 | 11.2 | 11.1 | 9.4 |
| 12 | 10.5 | 8.3 | 8.1 |
| 13 | 11.9 | 8.4 | 8.3 |
| 14 | 10.8 | 9.2 | 8.9 |
| 15 | 14.1 | 12.3 | 12.5 |
| 16 | 24.3 | 16.3 | 17.9 |
| 17 | 20.9 | 17.7 | 17.8 |
| 18 | 24.2 | 22.7 | 22.1 |
| 19 | 33.6 | 26.4 | 26.4 |
| 20 | 21.0 | 20.7 | 18.9 |
| 21 | 22.7 | 19.6 | 18.1 |
| 22 | 20.5 | 17.3 | 16.6 |
| 23 | 25.6 | 23.3 | 22.0 |
| 24 | 20.5 | 17.0 | 15.8 |
| Average | 15.2 | 13.3 | 12.8 |
| Intercept [HPLC] | | 1.4 | 0.9 |
| Slope [HPLC] | | 1.2 | 1.2 |
| R [HPLC] | | 0.957 | 0.974 |
| Intercept [IMx] | −0.3 | 0.5 | |
| Slope [IMx] | 0.8 | 1.0 | |
| r [IMx] | 0.976 | 0.990 | |

TABLE 14

Between-Run Precision

| | Homocysteine (μmol/L) | | | |
|---|---|---|---|---|
| Sample | Run 1 | Run 2 | Average | % CV |
| 1 | 16.35 | 16.46 | 16.41 | 0.47 |
| 2 | 12.13 | 12.58 | 12.36 | 2.58 |
| 3 | 19.45 | 21.6 | 20.53 | 7.41 |
| 4 | 16.29 | 16.79 | 16.54 | 2.14 |
| 5 | 11.13 | 10.01 | 10.57 | 7.49 |
| 6 | 7.33 | 7.56 | 7.45 | 2.18 |
| 7 | 6.31 | 7.24 | 6.78 | 9.71 |
| 8 | 7.13 | 5.54 | 6.34 | 17.75 |
| 9 | 14.87 | 14.5 | 14.69 | 1.78 |
| 10 | 13.81 | 13.41 | 13.61 | 2.08 |
| 11 | 26.86 | 28.66 | 27.76 | 4.58 |
| 12 | 12.45 | 13.05 | 12.75 | 3.33 |
| 13 | 10.15 | 10.74 | 10.45 | 3.99 |
| 14 | 9.6 | 10.39 | 10.00 | 5.59 |
| 15 | 12.53 | 13.67 | 13.10 | 6.15 |
| 16 | 14.60 | 15.20 | 14.90 | 2.85 |
| 17 | 25.03 | 25.65 | 25.34 | 1.73 |
| 18 | 20.77 | 20.03 | 20.40 | 2.56 |
| 19 | 31.83 | 32.10 | 31.97 | 0.60 |
| 20 | 36.86 | 36.43 | 36.65 | 0.83 |
| 21 | 11.65 | 11.48 | 11.57 | 1.04 |
| 22 | 40.22 | 38.25 | 39.24 | 3.55 |
| 23 | 31.68 | 32.62 | 32.15 | 2.07 |
| 24 | 7.68 | 6.38 | 7.03 | 13.08 |

Average CV (%) = 4.22

EXAMPLE 8

Effect of Reagent Concentration Variations

In this example, the preferred assay of the invention described in Example 7 was performed with variations in some of the reagent components, namely LDH, NADH and serine. This was done in order to determine the optimum amounts for these reagent components. The assays were performed as described above, with the respective components varied in concentration. Table 15 sets forth the results from these tests.

TABLE 15

Effect of Reagent Component Concentration Variations

| Final Reaction Mixture | SLOPE (mA/min/uM) | INTERCEPT mA/min | BLANK mA/min | Target Homocysteine range of control sample: 25–35 $\mu$M |
|---|---|---|---|---|
| [LDH] (U/L) | | | | |
| 114.5 | 1.21 | −0.14 | −10.2 | 25.8 |
| 229.3 | 1.14 | 0.12 | −11.2 | 28.1 |
| 458.7 | 1.17 | 0.14 | −11.3 | 26.6 |
| 917.5 | 0.88 | 1.89 | −11.3 | 27.2 |
| [NADH] (mM) | | | | |
| 0.130 | 0.77 | 4.23 | −10.7 | 32.9 |
| 0.259 | 1.12 | 0.05 | −11 | 25.2 |
| 0.389 | 1.09 | 0.45 | −10.7 | 26.8 |
| 0.519 | 1.13 | 0.49 | −11.1 | 26.0 |
| [SERINE] (mM) | | | | |
| 0.125 | 0.64 | 2.23 | −6.7 | 30.9 |
| 0.25 | 0.92 | 1.26 | −9.0 | 28.1 |
| 0.5 | 1.13 | 0.63 | −10.8 | 27.1 |
| 1 | 1.16 | 0.15 | −13.6 | 28.3 |
| 2 | 1.23 | 0.33 | −15.4 | 28.2 |

The results shown in Table 15 enabled the selection of final reagent component levels which provided adequate sensitivity with a minimal blank rate while also trying to minimize reagent costs.

EXAMPLE 9

Effect of R1 Formulation Change on the Cycling Assay

This example determined the effect of altering the pH by changing the buffer to TRIS, 250 mM at a pH of 8.4 and by adding lipase and α-cyclodextrin to Reagent 1. The performance of the assay was then tested after making these formulation changes. Table 16 details the reagent components used for these experiments.

TABLE 16

CBS/CBL/LDH CYCLING SYSTEM: Reagent Components

| Chemical | Concentration |
|---|---|
| Reagent 1 | |
| TRIS | 250 mM |
| L-cyclodextrin | 0.1% |
| Lipase | ≧200 kU/L |
| Serine | 1.295 mM |
| Lactate dehydrogenase | >800 U/L |
| NADH | 1.06 mM |
| Triton X-100 | 0.05% v/v |
| Sodium azide | 7.7 mM |
| pH = 8.2 | |
| Reagent SR1 | |
| TCEP | 26.3 mM |

TABLE 16-continued

CBS/CBL/LDH CYCLING SYSTEM: Reagent Components

| Chemical | Concentration |
|---|---|
| Reagent SR2 | |
| CBS | 28.5 KU/L |
| CBL | 9.4 KU/L |
| Glycerol | 10% |
| Sorbitol | 1% |
| Pyridoxal phosphate | 5 $\mu$M |
| Sodium azide | 7.7 mM |
| Potassium phosphate | 100 mM |
| pH = 7.6 | |

By changing the buffer of the Reagent 1 to TRIS, 250 mM at pH 8.4, improved assay consistency. This was because CBS and CBL are substantially more active at pH 8.4 and the rate of cycling is increased by about a factor of three.

Lipase and α-cyclodextrin were added to combat the problems associated with turbid (lipemic) samples which are sometimes encountered in the clinical laboratory. Such samples may arise when the patient from whom the sample is drawn has eaten shortly before the blood sample is drawn or when the patient has certain disease processes going on. Turbidity can interfere with results of this testing by producing such a high absorbance at 340 nm that the instrument cannot accurately measure the small changes in absorbance produced by the conversion of NADH to NAD. Turbidity can also interfere with the results of this testing dynamically by changing over time during the time when the NADH to NAD conversion is measured. For example, if the amount of turbidity is decreasing, the absorbance at 340 nm also decreases because light scattering is less. This effect adds to the absorbance decrease caused by the reduction of pyruvate and the resulting homocysteine determination may be substantially too high. The addition of lipase and α-cyclodextrin to R1 did decrease the turbidity of samples, presumably by the hydrolysis of triglycerides to glycerol and free fatty acids by lipase and by the free fatty acids forming complexes with the α-cyclodextrin. Thereby, turbid reaction mixtures clear by the time that SR2 (R3) is added allowing for accurate measurement of the rate of pyruvate production. Absorbances at 340 nm of many turbid reaction mixtures did rapidly decrease and level off in several minutes. Homocysteine results were accurate. However, the clearing of some turbid samples was not complete before the addition of SR2 (R3) and therefore, the results for some samples were somewhat inaccurate. Nonetheless, the use of lipase and alpha-cyclodextrin appears to be a very promising approach for achieving accurate results for turbid samples.

In addition to the changes made in the reagent constituents, the volumes were also varied in order to assess their effects on the performance of the assay. These changes are reflected in Table 17, which shows a typical cycling parameter on the Cobas MIRA. Following these changes a correlation study was carried out on 86 human samples with the results shown in Table 18.

TABLE 17

CBS/CBL/LDH Cycling System: Cobas MIRA Parameters

| Parameter | Setting |
|---|---|
| GENERAL | |
| Measurement Mode | Absorb |
| Reaction Mode | R-S-SR1-SR2 |
| Calibration Mode | Linear Regression |
| Reagent Blank | Reag/Sol |
| Cleaner | No |
| Wavelength | 340 nm |
| Decimal Position | 2 |
| Unit | µmol/L |
| ANALYSIS | |
| Post Dil. Factor | No |
| Conc. Factor | No |
| Sample cycle | 1 |
| volume | 20.0 µL |
| Diluent name | H$_2$O |
| volume | 45.0 µL |
| Reagent cycle | 1 |
| volume | 90 µL |
| Start R1 cycle | 2 |
| volume | 21 µl |
| Diluent name | H$_2$O |
| volume | 26 µL |
| Start R2 cycle | 17 |
| volume | 13 µL |
| Diuent name | H$_2$O |
| volume | 10 µL |
| CALCULATION | |
| Sample Limit | No |
| Reac. Direction | Decrease |
| Check | Off |
| Antigen Excess | No |
| Covers. Factor | 1.00 |
| Offset | 0.00 |
| Test range Low | On |
| High | On |
| Normal range Low | No |
| High | No |
| Number of Steps | 1 |
| Calc. Step A | Kinetic |
| Readings First | 20 |

TABLE 17-continued

CBS/CBL/LDH Cycling System: Cobas MIRA Parameters

| Parameter | Setting |
|---|---|
| Last | 31 |
| Reaction Limit | No |
| CALIBRATION | |
| Calib. Interval | Each Run |
| Blank Reag. Range Low | |
| High | No |
| Blank Range Low | No |
| High | No |
| Standard Position | 1 |
| 1 | 0.0 µmol/L |
| 2 | 8.5 µmol/L |
| 3 | 17.2 µmol/L |
| 4 | 25.2 µmol/L |
| 5 | 43.0 µmol/L |
| 6 | No |
| 7 | No |
| Replicate | Duplicate |
| Deviation | |
| Correction Std. Control | No |
| CS1 position | No |
| CS2 position | No |
| CS3 position | No |

TABLE 18

Correlation Data with Improvement listed in Tables 16 and 17.

| Sample | IMx (µmol/L) | Catch (µmol/L) |
|---|---|---|
| 2-01 | 11.0 | 12.0 |
| 2-02 | 17.7 | 17.3 |
| 2-03 | 18.6 | 18.4 |
| 2-04 | 22.1 | 21.2 |
| 2-05 | 12.2 | 13.8 |
| 2-06 | 15.2 | 14.9 |
| 2-07 | 17.6 | 20.4 |
| 2-09 | 51.8 | 49.9 |
| 2-11 | 29.1 | 28.2 |
| 2-13 | 19.6 | 19.2 |
| 2-15 | 25.0 | 24.7 |
| 2-16 | 22.9 | 23.7 |
| 2-17 | 21.9 | 21.3 |
| 2-18 | 25.0 | 23.80 |
| 2-19 | 22.2 | 22.10 |
| 2-21 | 23.6 | 20.80 |
| 2-22 | 13.0 | 13.60 |
| 2-23 | 23.1 | 21.80 |
| 2-24 | 17.0 | 17.60 |
| 2-26 | 15.9 | 14.80 |
| 2-27 | 8.8 | 9.30 |
| 2-28 | 9.1 | 9.40 |
| 2-29 | 5.2 | 5.40 |
| 2-30 | 8.2 | 8.10 |
| 2-31 | 4.7 | 5.40 |
| 2-32 | 6.6 | 6.80 |
| 2-33 | 7.8 | 8.10 |
| 2-34 | 7.0 | 7.0 |
| 2-35 | 6.9 | 7.3 |
| 2-36 | 4.8 | 5.7 |
| 4-01 | 7.2 | 7.3 |
| 4-02 | 7.3 | 9.1 |
| 4-03 | 6.2 | 5.8 |
| 4-04 | 9.5 | 9.5 |
| 4-05 | 6.2 | 7.4 |
| 4-06 | 8.2 | 8.0 |
| 4-07 | 6.8 | 6.7 |
| 4-08 | 8.1 | 7.4 |
| 4-09 | 6.5 | 7.9 |

TABLE 18-continued

Correlation Data with Improvement listed in Tables 16 and 17.

| Sample | IMx ($\mu$mol/L) | Catch ($\mu$mol/L) |
|---|---|---|
| 4-10 | 7.5 | 8.5 |
| 4-11 | 8.1 | 8.6 |
| 4-12 | 6.1 | 5.7 |
| 4-13 | 6.19 | 6.20 |
| 4-14 | 5.31 | 5.90 |
| 4-15 | 7.17 | 6.80 |
| 4-16 | 5.05 | 7.00 |
| 4-17 | 5.93 | 7.80 |
| 4-18 | 8.57 | 8.10 |
| 4-19 | 4.87 | 5.70 |
| 4-21 | 19.37 | 19.50 |
| 4-22 | 8.61 | 9.30 |
| 4-23 | 11.02 | 12.50 |
| 4-24 | 12.75 | 13.30 |
| 4-25 | 12.28 | 12.00 |
| 4-26 | 14.63 | 14.30 |
| 4-27 | 9.33 | 11.30 |
| 4-29 | 18.39 | 19.60 |
| 4-30 | 14.13 | 14.20 |
| 4-31 | 8.63 | 8.60 |
| 4-32 | 9.95 | 9.80 |
| 4-33 | 8.08 | 10.20 |
| 4-34 | 12.34 | 12.00 |
| 4-35 | 12.16 | 13.10 |
| 4-36 | 15.75 | 16.30 |
| 4-37 | 14.37 | 14.30 |
| 4-38 | 14.72 | 15.20 |
| 4-39 | 10.26 | 11.20 |
| 4-40 | 12.26 | 14.00 |
| 4-41 | 24.62 | 25.00 |
| 4-43 | 27.25 | 29.50 |
| 4-46 | 21.26 | 19.60 |
| 4-47 | 22.08 | 23.30 |
| 4-50 | 15.14 | 15.50 |
| E1 | 4.74 | 4.90 |
| E2 | 8.24 | 8.00 |
| E3 | 5.10 | 5.30 |
| E6 | 13.79 | 14.50 |
| E8 | 8.79 | 10.00 |
| E9 | 10.57 | 11.50 |
| E11 | 7.10 | 7.40 |
| E13 | 7.65 | 7.30 |
| E14 | 12.19 | 12.30 |
| E15 | 6.47 | 6.14 |
| E16 | 5.28 | 4.70 |
| E20 | 7.93 | 7.80 |
| Av. | 12.6 | 12.9 |
| Slope | | 0.957 |
| Intercept | | 0.8135 |
| R | | 0.9927 |

As shown by this comparison table, the results of this assay with the changed formulation was very accurate when compared with the commercially available IMx assay.

EXAMPLE 10

Use of Other Detergents and Their Concentration Variation

In this example, different detergents were used in combination with EDTA as components of R1. EDTA is known to stabilize lipid particles. Again the goal was to achieve accurate results when samples are turbid. In particular, the detergents Brij-35 and Genapol X-80 were studied. It was found that EDTA was particularly effective at the concentration of 2.5 mM to help minimize non-specific decrease in absorbance due to turbidity changes when lipemic samples are analyzed. Detergent concentrations were also varied as shown in Tables 19 and 20. One preferred composition for reagent R1 is shown in Table 21. Brij 35 was present at the level of 0.025% v/v and EDTA was present at 2.5 mM. Lipase and alpha-cyclodextrin were not present because they do not seem to be necessary to achieve accuracy with turbid samples when EDTA is present. Brij-35 (0.025%) was also put into SR2 (R3) in the place of Triton X-100. This may be a promising substitution because Triton X-100 is considered to be an environmental hazard by some countries. Table 22 shows the results of correlation study performed with the preferred reagent components.

TABLE 19

Varying Genapol X-80 Concentration

| | IMx | Results ($\mu$mol/L) change of Genapol X-80 concentration in R1 | | |
|---|---|---|---|---|
| Samples | ($\mu$mol/L) | 0.1% | 0.3% | 0.5% |
| Low | 7.00 | 6.31 | 6.19 | 5.64 |
| Medium | 12.50 | 11.96 | 11.48 | 10.37 |
| High | 25.00 | 23.08 | 22.96 | 22.86 |
| D910 | 14.30 | 14.38 | 14.50 | 14.11 |
| D912 | 9.40 | 9.41 | 10.60 | 9.50 |
| D913 | 5.00 | 5.58 | 6.47 | 4.53 |
| D915 | 21.20 | 23.85 | 21.93 | 20.92 |
| PBI 27 | 7.40 | 7.69 | 7.70 | 6.82 |
| PBI 28 | 6.80 | 7.33 | 7.19 | 5.96 |
| PBI 29 | 7.10 | 7.83 | 7.50 | 6.85 |
| PBI 10 | 8.90 | 9.61 | 9.07 | 7.67 |
| MAS 1 | 5.90 | 4.63 | 4.45 | 4.15 |
| MAS 2 | 14.50 | 14.46 | 15.33 | 14.47 |
| MAS 3 | 23.10 | 22.60 | 23.07 | 23.65 |
| D913X2 | 2.50 | 2.45 | 2.46 | 2.17 |
| Average | 11.37 | 11.41 | 11.39 | 10.64 |

TABLE 20

Varying Brij-35 Concentration in R1

| | IMx | Catch Results ($\mu$mol/L) as a function of Brij-35 Concentration in R1 | | | |
|---|---|---|---|---|---|
| Samples | ($\mu$mol/L) | 0.025% | 0.05% | 0.1% | 0.5% |
| 1 | 5.88 | 5.03 | 5.35 | 5.26 | 5.09 |
| 2 | 14.57 | 15.46 | 16.20 | 15.92 | 15.60 |
| 3 | 23.52 | 24.66 | 24.89 | 23.67 | 24.02 |
| 2 | 6.49 | 6.80 | 7.04 | 8.44 | 10.74 |
| 18 | 10.15 | 10.72 | 11.29 | 9.95 | 10.42 |
| 21 | 4.62 | 4.86 | 5.84 | 5.73 | 4.96 |
| 32 | 8.90 | 8.17 | 8.38 | 8.67 | 8.43 |
| Average | 10.59 | 10.81 | 11.28 | 11.09 | 11.32 |

TABLE 21

CBS/CBL/LDH CYCLING SYSTEM: Reagent Components

| Chemical | Concentration |
|---|---|
| Reagent 1 | |
| TRIS | 250 mM |
| EDTA | 2.5 mM |
| Serine | 1.295 mM |
| Lactate dehydrogenase | >800 U/L |
| NADH | 1.06 mM |
| Brij 35 | 0.025% w/v |
| Sodium azide | 7.7 mM |
| pH = 8.2 | |

TABLE 21-continued

CBS/CBL/LDH CYCLING SYSTEM: Reagent Components

| Chemical | Concentration |
|---|---|
| Reagent SR1 | |
| TCEP | 26.3 mM |
| Reagent SR2 | |
| CBS | 28.5 KU/L |
| CBL | 9.4 KU/L |
| Glycerol | 10% |
| Sorbitol | 1% |
| Pyridoxal phosphate | 5 µM |
| Sodium azide | 7.7 mM |
| Potassium phosphate | 100 mM |
| pH = 7.6 | |

TABLE 22

Correlation Data with best improvement

| Sample | IMx (µmol/L) | Catch (µmol/L) |
|---|---|---|
| 1 | 5.90 | 5.15 |
| 2 | 14.57 | 15.36 |
| 3 | 23.52 | 23.52 |
| 701 | 17.95 | 17.03 |
| 702 | 11.51 | 11.55 |
| 703 | 11.81 | 12.97 |
| 704 | 10.13 | 10.64 |
| 705 | 22.37 | 21.87 |
| 706 | 16.97 | 16.79 |
| 707 | 7.76 | 7.76 |
| 708 | 9.35 | 9.90 |
| 709 | 7.33 | 6.60 |
| 710 | 7.24 | 6.90 |
| 711 | 8.50 | 8.54 |
| 712 | 19.93 | 19.00 |
| 713 | 6.82 | 6.04 |
| 715 | 6.91 | 6.93 |
| 716 | 7.35 | 7.05 |
| 717 | 9.44 | 9.26 |
| 718 | 14.16 | 15.61 |
| 719 | 5.73 | 5.25 |
| 720 | 6.32 | 6.00 |
| 721 | 11.30 | 12.75 |
| 722 | 16.23 | 17.55 |
| 723 | 11.77 | 12.11 |
| 724 | 8.39 | 9.72 |
| 725 | 10.17 | 11.48 |
| 726 | 6.69 | 6.14 |
| 727 | 8.01 | 7.50 |
| 728 | 10.45 | 10.64 |
| 729 | 11.73 | 11.27 |
| 730 | 14.39 | 14.87 |
| 731 | 8.61 | 8.76 |
| 732 | 7.56 | 7.67 |
| 733 | 7.35 | 7.56 |
| 734 | 6.54 | 8.34 |
| 735 | 8.39 | 7.91 |
| Av. | 10.79 | 10.92 |
| slope | | 1.0035 |
| intercept | | 0.0195 |
| R | | 0.9873 |

When Brij-35 and EDTA were substituted for Triton X-100 and lipase plus α-cyclodextrin, there was some clearing of the turbid reaction mixtures. However, perhaps not as much as in the case when lipase and alpha-cyclodextrin are also used. Importantly, the absorbances at 340 nm quickly stabilized with zero rates of change. Thus when SR2 (R3) was added, the rate of pyruvate production is accurately measured and accurate results are obtained even in the cases of samples appearing like milk. This is even the case when the time between addition of R1 and SR2 (R3) is shortened by 2–4 minutes, which may be necessary to apply the homocysteine assay of the present invention to other automated instruments.

EXAMPLE 11

Results From Changing Reducing Agent to TCEP and Alterations in Concentration of TCEP For this example, the reducing agent DTE was replaced with Tris (2-carboxyethylphosphine)hydrochloride (TCEP). TCEP has the advantage of being stable in purified water for an extended period of time. Replacement of DTE with TCEP reduced the reagent blank reaction from about 12 to 15 mA/min to about 4 to 5 mA/min. The lower reagent blank enables better Homocysteine assay precision. To find the optimum concentration of TCEP for this Homocysteine assay, a range of concentration was tested. The results from these experiments are given in Table 23.

TABLE 23

Varying TCEP Concentration in SR1

| | | Homocysteine Results (µmol/L) | | | | | |
|---|---|---|---|---|---|---|---|
| SR1 | IMx | Catch Assay | | | | | |
| Formulation | | A | B | C | D | E | F |
| MAS 1 | 5.88 | 6.37 | 6.18 | 5.48 | 5.51 | 4.42 | 4.17 |
| MAS 2 | 14.57 | 16.49 | 15.67 | 15.95 | 16.03 | 15.80 | 14.77 |
| MAS 3 | 23.52 | 23.19 | 21.98 | 23.33 | 25.11 | 24.02 | 23.09 |
| PBI 20 | 7.2 | 5.81 | 6.24 | 7.81 | 8.00 | 6.95 | 8.33 |
| PBI 22 | 7.8 | 7.61 | 7.66 | 8.28 | 8.69 | 8.44 | 8.23 |
| PBI 36 | 5.1 | 4.16 | 4.61 | 4.71 | 5.05 | 5.18 | 4.71 |
| PBI 39 | 4.6 | 3.11 | 4.25 | 4.38 | 4.47 | 3.68 | 4.09 |
| Doreen 709 | 7.33 | 6.68 | 6.64 | 6.71 | 7.28 | 6.23 | 6.43 |
| Average | 9.50 | 9.17 | 9.15 | 9.58 | 10.02 | 9.34 | 9.22 |

TCEP Concentrations:
A = 6.3 mM;
B = 13.85 mM;
C = 26.44 mM;
D = 32.74 mM;
E = 39.03 mM;
F = 52.88 mM

EXAMPLE 12

Determination of the Effect of Changing the R3 Buffer to Phosphate and the Addition of Glycerol to the Buffer In order to have enzyme mixtures that would have longer stability and assay compatibility, the enzyme formulation was changed to a mixture that provides significantly longer shelf-life than the previous formulation. The significant changes involved replacement of Tris buffer with a phosphate and addition of glycerol to the buffer. Potassium phosphate at concentrations ranging from 50 mM to 500 mM at pH 7.6 were used and glycerol concentrations ranging from 0.5% to 15.0% (v/v) were used. As a result from these changes, the shelf life was increased significantly from weeks to more than a year at 4° C. In preferred forms, potassium phosphate can range from about 50 mM to about 250 mM. More preferably, potassium phosphate can range from about 75 mM to about 150 mM. A particularly effective concentration of potassium phosphate in this experiment was 100 mM. Glycerol can range from about 1–15%. More preferably, this range is from about 5–13%. A particularly effective concentration of glycerol in this experiment was 10%.

EXAMPLE 13

Results Obtained Using Different Instruments

To determine the overall improvement resulting from all the changes to the assay, precision evaluations were done on several instruments by writing protocol that is specific to that instrument. Table 24 sets forth the parameters and settings used in accordance with the present invention with the Roche Hitachi 911 and Table 25 sets forth the same parameters and settings when the Beckman CX-5 is used. Below are the tables showing the results of these precision tests. These results are significantly better than what was obtained with the earlier formulations of the assay. On the Hitachi 911 (Table 26) and Beckman CX5 (Table 27) instruments, each sample shown was run 20× and the within run precision was determined. Percent C. V. for samples as low as 5.92 $\mu$mol/L was 3.31% and samples in the range of 23.01 $\mu$mol/L to 25.4 $\mu$mol/L was 1.9% to 2.03%. A total precision (Table 28) of between 7.3% and 2.6% was obtained on samples with homocysteine values of 4.6 $\mu$mol/L and 27.0 $\mu$mol/L on the Cobas MIRA Plus. Each sample was run in duplicate, 2× per day for a total of 20 days.

TABLE 24

Catch Homocysteine Method Parameters for the Roche Hitachi 911

| Test | THCY |
|---|---|
| Assay Code | Rate-A, 15 |
| Wavelength (2nd/Primary) | 376/340 |
| Assay Point | 35-49-0-0 |
| Serum | |
| S. Vol. (Normal) | 28 |
| S. Vol. (Decrease) | 20 |
| S. Vol. (Increase) | 30 |
| Urine | |
| S. Vol. (Normal) | 10 |
| S. Vol. (Decrease) | 10 |
| S. Vol. (Increase) | 10 |
| ABS. Limit | 0-0-Decrease |
| Prozone Limit | 0-0-Lower |
| Reagent | |
| T1 | 200 $\mu$L - 0-0-00322-0 |
| T2 | 25 $\mu$L - 0-0-00322-0 |
| T3 | 0 - 0-0-00322-0 |
| Calibration Type | Linear-2-2-0 |
| Auto Time Out | |
| Blank | 0 |
| Span | 0 |
| 2 Point | 0 |
| Full | 0 |
| Auto Change | |
| Lot | Cancel |
| Bottle | Cancel |
| Select Tests via Keyboard: | ENTER |
| SD Limit | 100 |
| Duplicate Limit | 1000 |
| Sensitivity Limit | 0 |
| S1 ABS Limit | (−32000) (32000) |
| Compensated Limit | Blank |
| PARAMETER PAGE 2 | |
| Test | THCY - 00322 |
| Test Name | THCY Unit: $\mu$mol/L |
| Data Mode | On Board |

TABLE 24-continued

Catch Homocysteine Method Parameters for the Roche Hitachi 911

| Test | THCY |
|---|---|
| Report Name | Homocysteine |
| Control Interval | 0 |
| Instrument Factor (Y = aX + b) | |
| a | 1 |
| b | 0 |
| Expected Values | user defined |
| Technical Limit | |
| Serum | 0-10000 |
| Urine | (−99999) (999999) |
| STD | Conc.-Pos.-Sample-Pre.-Dil.-Calib. |
| 1 | 0.0-18-28-0-0-501 |
| 2 | 25.2-26-28-0-0-026 |
| 3 | 0 |
| 4 | 0 |
| 5 | 0 |
| 6 | 0 |

For this experiment, T1 is prepared by mixing R1 and deionized water in the ratio of 9 to 8.1. Reagents T2 and T4 correspond to Reagents SR1 and SR2, respectively.

TABLE 25

Catch Homocysteine Method Parameters for the Beckman CX-5

| Chemistry Name: | HOMOCYSTEINE |
|---|---|
| Test Name | HOMO |
| Calculation Factor: | 0 |
| Reaction Type: | RATE 1 |
| Math Model: | Linear |
| Cal Time Limit: | 24 Hrs |
| Reaction Direction: | Decreasing |
| No. of Calibrators: | 2 |
| Units: | $\mu$mol/L |
| Decimal Precision | X.XX |
| Primary Wavelength: | 340 nm |
| Secondary Wavelength: | 380 nm |
| Sample Volume | 25 $\mu$L |
| Primary Inject Rgt: | |
| A | 179 $\mu$L |
| B | 22 $\mu$L |
| Secondary Inject Rgt: | |
| C | 14 $\mu$L |
| Add Time: | 592 sec |
| CALIBRATORS | |
| #1 | 0.00 |
| #2 | 24.8 |
| MULTIPOINT SPAN | |
| 1–2: | −0.001 |
| REAGENT BLANK | |
| Start Read: | 100 sec |
| End Read: | 200 sec |
| Low ABS Limit: | −1.5 |
| High ABS Limit | 1.5 |
| USABLE RANGE | |
| Lower Limit: | 0.00 |
| Upper Limit: | 99999.00 |
| SUBSTRATE DEPLETION | |
| Initial Rate: | −99.999 |
| Delta ABS | 1.5 |

For this example, Reagent A is prepared by mixing R1 and deionized water in the ration of 9 to 8.1. Reagents B and C correspond to MIRA reagents SR1 and SR2.

TABLE 26

Within Run Precision on Hitachi 911

|  |  | Within Run |
|---|---|---|
| Low | Std. Dev. | 0.224 |
| Mean = 8.3 μmol/L | % C.V. | 2.17 |
| Medium | Std. Dev. | 0.324 |
| Mean = 11.9 μmol/L | % C.V. | 2.71 |
| High | Std. Dev. | 0.516 |
| Mean = 25.4 μmol/L | % C.V. | 2.03 |

TABLE 27

Within Run Precision on Beckman CX5

|  |  | Within Run |
|---|---|---|
| Low | Std. Dev. | 0.196 |
| Mean = 5.92 μmol/L | % C.V. | 3.31 |
| Medium | Std. Dev. | 0.195 |
| Mean = 11.12 μmol/L | % C.V. | 1.70 |
| High | Std. Dev. | 0.437 |
| Mean = 23.01 μmol/L | % C.V. | 1.90 |

TABLE 28

Total Precision on Roche MIRA-Plus

|  |  | Within Run | Between Run | Between Day | Total |
|---|---|---|---|---|---|
| Low | Std. Dev. | 0.31 | 0.14 | 0.04 | 0.34 |
| Mean = 4.6 μmol/L | % C.V. | 6.6 | 3.1 | 0.8 | 7.3 |
| Medium | Std. Dev. | 0.40 | 0.08 | 0.23 | 0.47 |
| Mean = 11.6 μmol/L | % C.V. | 3.5 | 0.7 | 2.0 | 4.0 |
| High | Std. Dev. | 0.44 | 0.39 | 0.39 | 0.71 |
| Mean = 27.0 μmol/L | % C.V. | 1.6 | 1.5 | 1.4 | 2.6 |

EXAMPLE 14

Adaptability of the Assay to a 2-Reagent System

The present invention can also be adapted to system which uses only two reagents. This makes the invention adaptable to wider range of instruments including those that can only use two reagents. Table 29 shows the reagent contents of the two-reagent system and Table 30 shows the MIRA plus parameters of how the assay was performed on that chemistry analyzer. Shown in Table 31 are the comparison data obtained using the 3-reagents system versus the 2-reagents system.

TABLE 29

CBS/CBL/LDH CYCLING SYSTEM: Reagent Components for 2-Reagents

| Chemical | Concentration |
|---|---|
| Reagent 1 | |
| TRIS | 250 mM |
| EDTA | 2.5 mM |
| Serine | 1.295 mM |
| Lactate dehydrogenase | >800 U/L |
| NADH | 1.06 mM |
| Brij 35 | 0.025% v/v |
| Sodium azide | 7.7 mM |
| TCEP | 4.05 mM |
| pH = 8.2 | |
| Reagent SR1 | |
| CBS | 28.5 KU/L |
| CBL | 9.4 KU/L |
| Glycerol | 10% |
| Sorbitol | 1% |
| Pyrdoxal phosphate | 5 μM |
| Sodium azide | 7.7 mM |
| Potassium phosphate | 100 mM |
| pH = 7.6 | |

TABLE 30

CBS/CBL/LDH Cycling System for 2-Reagents: Cobas MIRA Parameters

| Parameter | Setting |
|---|---|
| GENERAL | |
| Measurement Mode | Absorb |
| Reaction Mode | R-S-SR1 |
| Calibration Mode | Linear Regression |
| Reagent Blank | Reag/Sol |
| Cleaner | No |
| Wavelength | 340 nm |
| Decimal Position | 2 |
| Unit | μmol/L |
| ANALYSIS | |
| Post Dil. Factor | No |
| Conc. Factor | No |

TABLE 30-continued

CBS/CBL/LDH Cycling System for 2-Reagents: Cobas MIRA Parameters

| Parameter | | Setting |
|---|---|---|
| Sample | cycle | 1 |
| | volume | 20.0 μL |
| Diluent | name | $H_2O$ |
| | volume | 45.0 μL |
| Reagent | cycle | 1 |
| | volume | 137 μL |
| Start R1 | cycle | 16 |
| | volume | 13 μL |
| Diuent | name | $H_2O$ |
| | volume | 10 μL |
| CALCULATION | | |
| Sample Limit | | No |
| Reac. Direction | | Decrease |
| Check | | Off |
| Antigen Excess | | No |
| Covers. Factor | | 1.00 |
| Offset | | 0.00 |
| Test range | Low | On |
| | High | On |
| Normal range | Low | No |
| | High | No |
| Number of Steps | | 1 |
| Calc. Step A | | Kinetic |
| Readings | First | 19 |
| | Last | 30 |
| Reaction Limit | | No |
| CALIBRATION | | |
| Calib. Interval | | Each Run |
| Blank Sol-Pos | | 1 |
| Reag. Range | Low | No |
| | High | No |
| Blank Range | Low | No |
| | High | No |
| Standard Position | | 1 |
| 1 | | 0.0 μmol/L |
| 2 | | 8.5 μmol/L |
| 3 | | 17.2 μmol/L |
| 4 | | 25.2 μmol/L |
| 5 | | 43.0 μmol/L |
| 6 | | No |
| 7 | | No |
| Replicate | | Duplicate |
| Deviation | | |
| Correction Std. | | No |
| Control | | |
| CS1 position | | No |
| CS2 position | | No |
| CS3 position | | No |

TABLE 31

Comparison of 2-Reagent System versus 3-Reagent System.

| Samples | IMx (μmol/L) | Catch Inc. 2-Reagent System | Hcy Assay (μmol/L) 3-Reagent System |
|---|---|---|---|
| MAS 1 | 5.88 | 5.55 | 5.17 |
| MAS 2 | 14.57 | 16.14 | 15.70 |
| MAS 3 | 23.52 | 23.99 | 23.47 |
| P 10 | 8.90 | 9.32 | 9.65 |
| P 11 | 7.60 | 7.45 | 7.27 |
| P 33 | 7.80 | 8.11 | 8.29 |
| P 34 | 5.93 | 5.21 | 5.69 |
| 754 + 848 | 16.00 | 15.68 | 16.15 |
| Average | 11.28 | 11.43 | 11.42 |

EXAMPLE 15

Adaptability of the Present Invention for Use with Single-Point Calibration

The homocysteine assay of the present invention has also been adapted to using a single calibration point, with the zero calibrator serving as the blank. Table 32 below shows the parameters for performing a single point calibration on the Mira instrument. The data below (Table 33) shows that using single point calibration in the slope average mode generates results that are substantially equivalent to using the multi-point calibration curve.

TABLE 32

CBS/CBL/LDH Cycling System: Cobas MIRA Parameters for Single Point Calibration

| Parameter | | Setting |
|---|---|---|
| GENERAL | | |
| Measurement Mode | | Absorb |
| Reaction Mode | | R-S-SR1 |
| Calibration Mode | | Slope Average |
| Reagent Blank | | Reag/Sol |
| Cleaner | | No |
| Wavelength | | 340 nm |
| Decimal Position | | 2 |
| Unit | | μmol/L |
| ANALYSIS | | |
| Post Dil. Factor | | No |
| Conc. Factor | | No |
| Sample | cycle | 1 |
| | volume | 20.0 μL |
| Diluent | name | $H_2O$ |
| | volume | 45.0 μL |
| Reagent | cycle | 1 |
| | volume | 137 μL |
| Start R1 | cycle | 16 |
| | volume | 13 μL |
| Diuent | name | $H_2O$ |
| | volume | 10 μL |
| CALCULATION | | |
| Sample Limit | | No |
| Reac. Direction | | Decrease |
| Check | | Off |
| Antigen Excess | | No |
| Covers. Factor | | 1.00 |
| Offset | | 0.00 |
| Test range | Low | On |
| | High | On |
| Normal range | Low | No |
| | High | No |
| Number of Steps | | 1 |
| Calc. Step A | | Kinetic |
| Readings | First | 19 |
| | Last | 30 |
| Reaction Limit | | No |
| CALIBRATION | | |
| Calib. Interval | | Each Run |
| Blank Sol-Pos | | 1 |
| Reag. Range | Low | No |
| | High | No |
| Blank Range | Low | No |
| | High | No |
| Standard Position | | 4 |
| 1 | | 25.2 μmol/L |
| 2 | | NO |
| 3 | | NO |
| Replicate | | Duplication |
| Deviation | | |
| Correction Std. | | No |

TABLE 32-continued

CBS/CBL/LDH Cycling System: Cobas MIRA Parameters for Single Point Calibration

| Parameter | Setting |
|---|---|
| Control | |
| CS1 position | No |
| CS2 position | No |
| CS3 position | No |

TABLE 33

Single-Point versus Multi-Point Calibration

| | | Catch Inc. Hcy Assay ($\mu$mol/L) | |
|---|---|---|---|
| Samples | IMx ($\mu$mol/L) | Single Point Calibration | Multi-Point Calibration |
| MAS 1 | 5.88 | 5.03 | 5.17 |
| MAS 2 | 14.57 | 15.18 | 15.70 |
| MAS 3 | 23.52 | 22.97 | 23.47 |
| PB1 10 | 8.90 | 8.82 | 9.65 |
| PBI 11 | 7.60 | 8.26 | 7.27 |
| PBI 33 | 7.80 | 8.05 | 8.29 |
| PBI 34 | 5.93 | 5.80 | 5.69 |
| 754 + 848 | 16.00 | 15.17 | 16.15 |
| Average | 11.28 | 11.16 | 11.42 |

EXAMPLE 16

Study of Homocysteine Assays Described in WO 00/28071

PCT Publication WO 00/28071 describes in detail two homocysteine assays. In the "first embodiment", the assay is performed without a reduction step. To convert that method to one useful for human plasma homocysteine measurements, either a separate off-line or a homogeneous reduction step must be incorporated. Publication WO 00/28071 describes a separate off-line reduction step perhaps because a pyruvate oxidase cycling system is used. That step entails an incubation of 20 min. before the reduced specimen can be analyzed, which greatly increases total assay time and labor cost. Moreover, if the sample is to be assayed for more than one analyte in the clinical laboratory, the primary serum or plasma sample must be split into two aliquots, one for the homocysteine test and one for any other ordered laboratory test. In contrast, the present invention enables homogeneous reduction since a LDH cycling system is used (Example 7).

Figure 15:
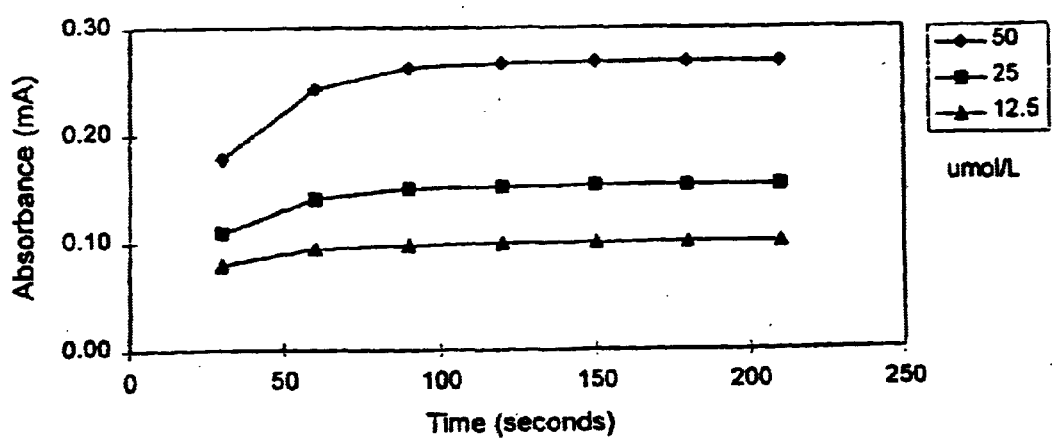
FIG. 15 depicts a graph of absorbance versus time for the no-DTT pyruvate assay described in Example 9.
Figure 16:
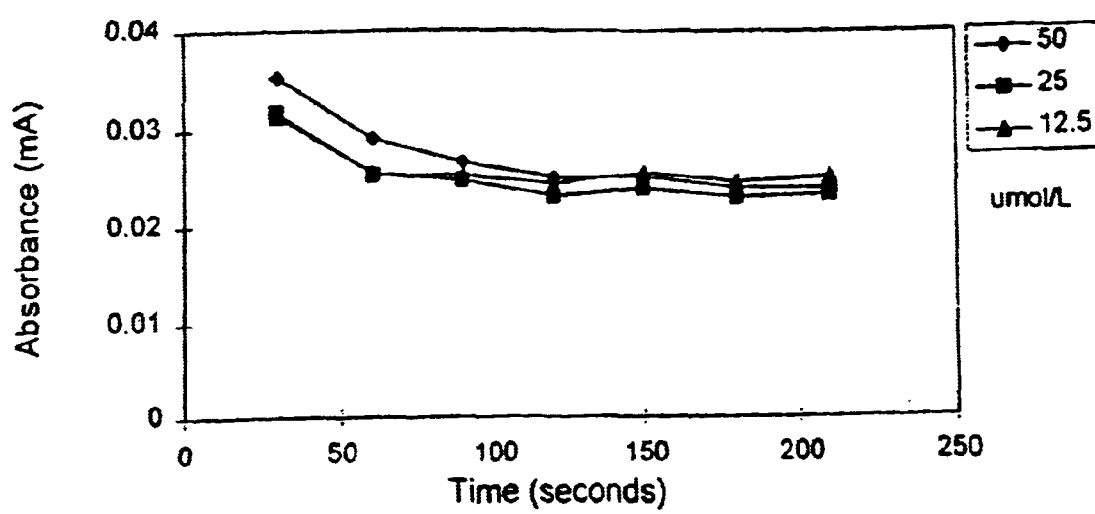
FIG. 16 depicts a graph of absorbance versus time for the DTT-containing pyruvate assay described in Example 9.

Here, in Example 16 (Table 34), it is shown that DTT in fact does interfere with the pyruvate oxidase detection system described in the "second embodiment" of WO 00/28071. In particular, the reagent and DTT compositions described in the "second embodiment" were used, and assays with and without DTT were carried out against known pyruvate standards (12.5, 25, and 50 $\mu$mol/L) using a Cobas FARA instrument. In the case of the DTT test, 40 $\mu$L of each standard was mixed with 30 $\mu$L of the DTT solution, followed by incubation for 100 sec. Thereafter, 90 $\mu$L of pyruvate oxidase reagent was added and incubated for 30 sec. Absorbance readings were then taken at 30, 60, 90, 120, 150, 180 and 210 sec. In the "no DTT" test, the same procedure was followed except that no DTT was added. Table 34 sets forth the results of this experiment using the 210 sec. readings. FIGS. 15 and 16 further illustrate the results of this test.

TABLE 34

Effect of DTT on PO/HRP pyruvate detection system

| | WITHOUT DTT | WITH DTT |
|---|---|---|
| Blank | 0.0021 | −0.0021 |
| Factor | 2212 | −11765 |
| 50 $\mu$mol/L Standard | 51.5 | 35.3 |
| 25 $\mu$mol/L Standard | 24.1 | 0.0 |
| 12.5 $\mu$mol/L Standard | 9.7 | −21.2 |
| Delta change at 30 sec. (50 $\mu$mol std.) | 0.0643 | −0.0062 |
| Delta change at 90 sec. (50 $\mu$mol std.) | 0.0890 | −0.0103 |
| Delta change at 120 sec. (50 $\mu$mol std.) | 0.0903 | −0.0113 |
| Delta change at 210 sec. (50 $\mu$mol std.) | 0.0906 | −0.0113 |

These data clearly demonstrate the necessity of the separate reduction step described in the "second embodiment" of WO 00/28071. The presence of the reductant interferes with the pyruvate oxidase detection system used to assay for pyruvate. Therefore, the data presented here confirm that the time-consuming separate off-line reduction step is essential in the "second embodiment." In addition, the off-line reduction step described in WO 00/28071 will likely elevate significantly the assay complexity and cost relative to the present invention.

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

We claim:

1. In an enzymatic cycling assay for assessing the amount of homocysteine and/or cystathionine in a solution including the steps of:

(a) creating a reaction mixture by reacting the solution containing homocysteine and/or cystathionine with cystathionine β-synthase, or a derivative thereof, L-serine, and cystathionine β-lyase, or a derivative thereof, for a time period sufficient to catalyze the cyclical conversion of homocysteine to cystathionine and the reconversion of cystathionine to homocysteine with the production of pyruvate and ammonia;

(b) determining the amount of pyruvate and/or ammonia present in the reaction mixture; and (c) assessing the amount of homocysteine and/or cystathionine present in the solution based on the amount of pyruvate and/or ammonia produced, the improvement which comprises the step of completing reaction step (a) in less than 15 minutes.

2. The method of claim 1, wherein the L-serine is added to the reaction mixture to a final concentration of at least about 1 μM to about 50 mM.

3. The method of claim 2, wherein said L-serine is added to the reaction mixture to a final concentration of from at least about 10 μM to about 40 mM.

4. The method of claim 1, wherein the amount of pyruvate is determined by the enzymatic conversion of pyruvate to lactate.

5. The method of claim 4, wherein the conversion of pyruvate to lactate is by the addition of lactate dehydrogenase, or a derivative thereof, and NADH, or a derivative thereof.

6. The method of claim 5, wherein said lactate dehydrogenase is added to the reaction mixture to a final concentration of at least about 30 U/l to about 5000 U/l.

7. The method of claim 6, wherein said lactate dehydrogenase is added to the reaction mixture to a final concentration of at least about 30 U/l to about 3000 U/l.

8. The method of claim 5, wherein said NADH is added to the reaction mixture to a final concentration of at least about 0.1 mM to about 2 mM.

9. The method of claim 8, wherein said NADH is added to the reaction mixture to a final concentration of at least about 0.1 mM to about 1.5 mM.

10. The method of claim 5, wherein the total amount of NADH oxidation, or a derivative thereof, to NAD+, or a derivative thereof, is determined by reacting the NAD+, or a derivative thereof, with a dye capable of undergoing a color change when oxidized.

11. The method of claim 10, wherein said dye is selected from the group consisting of 5,5'-dithiobis(2-nitrobenzoic acid), 2,6-dichlorophenolindophenol, a tetrazolium compound, phenazine methosulfate, methyl viologen, or derivatives of each thereof.

12. The method of claim 1, wherein the amount of pyruvate is determined by the enzymatic conversion of pyruvate to hydrogen peroxide.

13. The method of claim 12, wherein said enzyme is pyruvate oxidase.

14. The method of claim 13, wherein the assay further comprises a peroxidase and a water soluble hydrogen donor, which upon donating a hydrogen forms a stable colored product which can be detected spectrophotometrically.

15. The method of claim 14, wherein the water soluble hydrogen donor is a derivative of N-alkyl-N-sulfopropylaniline.

16. The method of claim 15, wherein the derivative of N-alkyl-N-sulfopropylaniline is a sodium salt of N-ethyl-N-(2-hydroxy-3-sulfopropyl)-m-toluidine.

17. The method of claim 1, further comprising the step of treating the solution with a reducing agent for a time period sufficient to reduce substantially all of any homocysteine and mixed disulfides containing half homocysteine that are present in the solution to homocysteine.

18. The method of claim 17, said treating step being performed prior to steps (a)–(c).

19. The method of claim 17, wherein said reducing agent comprises a borohydride salt or a thiol reducing agent.

20. The method of claim 19, wherein said reducing agent is selected from the group consisting of β-mercaptoethanol, dithiothreitol, dithioerythritol, TCEP, or thioacetic acid, or derivatives of each thereof.

21. The method of claim 20, said dithiothreitol being present in an amount of from about 0.2 mM to about 3 mM.

22. The method of claim 20, said dithioerythritol being present in an amount of from about 0.2 mM to about 3 mM.

23. The method of claim 20, said thioacetic acid being present in an amount of from about 0.2 mM to about 3 mM.

24. The method of claim 20, said β-mercaptoethanol being present in an amount of from about 0.2 mM to about 3mM.

25. The method of claim 20, said TCEP being present in an amount of from about 6 mM to about 53 mM.

26. The method of claim 1, wherein the amount of ammonia is determined by an ammonia sensor, a microdiffusion assay, a colorimetric assay, or an enzyme assay.

27. The method of claim 1, further comprising the step of treating the solution with a reagent comprising cystathionine γ-lyase, or a derivative thereof, for a time period sufficient to convert any cystathionine present in the solution to α-ketoglutarate.

28. The method of claim 27, said treating step being performed prior to steps (a)–(c).

29. The method of claim 27, further comprising the step of eliminating substantially all of the activity of cystathionine γ-lyase, or derivative thereof, after said treatment step and prior to performing steps (a)–(c).

30. The method of claim 29, wherein said cystathionine γ-lyase activity is eliminated by heating.

31. The method of claim 1, wherein said cystathionine β-synthase, or a derivative thereof, or cystathionine β-lyase, or a derivative thereof, are provided as an extract isolated from a eukaryotic or prokaryotic cell.

32. The method of claim 31, wherein said eukaryotic cells comprise yeast cells.

33. The method of claim 32, wherein said yeast cells comprise *Saccharomyces cerevisiae*.

34. The method of claim 31, wherein said prokaryotic cells comprise bacterial cells.

35. The method of claim 34, wherein said bacterial cells are selected from the group consisting of *Escherichia coli, Hemophilus influenzae, Rhizobium leguminosarum,* or *Bordetella avium* cells.

36. The method of claim 31, wherein said cystathionine β-synthase, or a derivative thereof, or cystathionine β-lyase, or a derivative thereof, are substantially isolated from said extract.

37. The method of claim 1, wherein said cystathionine β-synthase, or a derivative thereof, or cystathionine β-lyase, or a derivative thereof, are produced by the recombinant expression of a gene encoding cystathionine β-synthase, or a derivative thereof, or cystathionine β-lyase, or a derivative thereof.

38. The method of claim 37, wherein said cystathionine β-synthase, or a derivative thereof, and cystathionine β-lyase, or a derivative thereof, are produced as a fusion protein.

39. The method of claim 38, wherein said fusion protein is expressed from a recombinantly produced gene comprising a region encoding cystathionine β-synthase, or a derivative thereof, operatively associated with a region comprising a gene encoding cystathionine β-lyase, or a derivative thereof.

40. The method of claim 39, wherein said fusion protein is immobilized on a solid support.

41. The method of claim 1, wherein said cystathionine β-synthase is added to a final concentration of from about 0.1 KU/l to about 100 KU/l.

42. The method of claim 41, wherein said cystathionine β-synthase is added to a final concentration of from about 0.5 KU/l to about 75 KU/l.

43. The method of claim 1, wherein said cystathionine β-lyase is added to a final concentration of from about 0.01 KU/l to about 100 KU/l.

44. The method of claim 43, wherein said cystathionine β-lyase is added to a final concentration of from about 0.05 KU/l to about 50 KU/l.

45. The method of claim 1, said reaction mixture including a buffer.

46. The method of claim 45, said buffer operable for maintaining said reaction mixture at a pH of between about 7 to about 9.

47. The method of claim 45, said buffer being selected from the group consisting of HEPES, TRIS, and phosphate.

48. The method of claim 47, said TRIS being at a pH of about 8.4.

49. The method of claim 45, further comprising the step of adding glycerol to said buffer.

50. The method of claim 49, said buffer having a concentration of from about 0.5% to about 15.0% v/v.

51. The method of claim 1, further comprising the step of reducing the turbidity of said solution.

52. The method of claim 51, further comprising the step of contacting said solution with a lipoprotein clearing agent.

53. The method of claim 51, said agent comprising lipase and α-cyclodextrin.

54. The method of claim 52, said lipoprotein clearing agent being in said reaction mixture.

55. The method of claim 1, said reaction mixture containing a detergent.

56. The method of claim 55, said detergent operable for reducing the turbidity of said solution.

57. The method of claim 55, said detergent being selected from the group consisting of Triton X-100, Brij-35, and Genapol X-80.

58. The method of claim 57, said detergent being Genapol X-80.

59. The method of claim 58, said Genapol X-80 being present at a concentration of from about 0.05% to about 0.5% u$\mu$mol/L.

60. The method of claim 57, said detergent being Brij-35.

61. The method of claim 60, said Brij-35 being present at a concentration of from about 0.01% to about 0.5% $\mu$mol/L.

62. The method of claim 1, said reaction mixture including comprising a phosphate.

63. The method of claim 62, said phosphate being present at a concentration ranging from about 50 mM to about 500 mM.

64. The method of claim 1, said reaction mixture including EDTA.

65. The method of claim 64, said EDTA being present at a concentration of from about 0.5 mM to about 10 mM.

66. The method of claim 65, said EDTA being present at a concentration of from about 2 mM to about 3 mM.

67. The method of claim 1, said reaction mixture comprising at least 2 reagent compositions.

68. The method of claim 1, said solution having a volume of from about 10 $\mu$l to about 40 $\mu$l.

69. The method of claim 1, said assay being performed on a clinical chemistry analyzer.

70. The method of claim 1, said assay requiring no off-instrument step.

71. A test kit for use in assessing the amount of homocysteine in a sample solution comprising cystathionine β-synthase, or a derivative thereof, L-serine, cystathionine β-lyase, or a derivative thereof.

72. The test kit of claim 71, further comprising a container for holding said sample.

73. The test kit of claim 71, said cystathionine β-synthase being present in a final concentration of from about 0.1 to about 100 KU/l.

74. The test kit of claim 73, said cystathionine β-synthase being present in a final concentration of from about 0.5 to about 75 KU/l.

75. The test kit of claim 71, said L-serine being present in a final concentration of from about 1 $\mu$M to about 50 mM.

76. The test kit of claim 75, said L-serine being present in a final concentration of from about 10 $\mu$M to about 40 mM.

77. The test kit of claim 71, said cystathionine β-lyase being present in a final concentration of from about 0.01 to about 100 KU/l.

78. The test kit of claim 77, said cystathionine β-lyase being present in a final concentration of from about 0.05 to about 50 KU/l.

79. The test kit of claim 71, further comprising lactate dehydrogenase, or a derivative thereof, and NADH, or a derivative thereof.

80. The test kit of claim 79, said lactate dehydrogenase being present in a final concentration of from about 30 to about 5000 U/l.

81. The test kit of claim 80, said lactate dehydrogenase being present in a final concentration of from about 30 to about 3000 U/l.

82. The test kit of claim 79, said NADH being present in a final concentration of from about 0.1 mM to about 2 mM.

83. The test kit of claim 82, said NADH being present in a final concentration of from about 0.1 mM to about 1.5 mM.

84. The test kit of claim 71, further comprising a dye capable of undergoing a color change when oxidized.

85. The test kit of claim 84, wherein said dye is selected from the group consisting of 5,5'-dithiobis(2-nitrobenzoic acid), 2,6-dichlorophenolindophenol, a tetrazolium compound, phenazine methosulfate, methyl viologen, or a derivative of each, thereof.

86. The test kit of claim 71, further comprising a separate container, said separate container containing a reducing agent.

87. The test kit of claim 86, wherein said reducing agent comprises a borohydride salt or a thiol reducing agent.

88. The test kit of claim 87, wherein said thiol reducing agent is selected from the group consisting of β-mercaptoethanol, dithiothreitol, dithioerythritol, TCEP, or thioacetic acid, or any salt of each, thereof.

89. The test kit of claim 88, said dithiothreitol being present in an amount of from about 0.2 mM to about 3 mM.

90. The test kit of claim 89, said dithioerythritol being present in an amount of from about 0.2 mM to about 3 mM.

91. The test kit of claim 88, said thioacetic acid being present in an amount of from about 0.2 mM to about 3 mM.

92. The test kit of claim 88, said β-mercaptoethanol being present in an amount of from about 0.2 mM to about 3 mM.

93. The method of claim 88, said TCEP being present in an amount of from about 6 mM to about 53 mM.

94. The test kit of claim 71, further comprising cystathionine γ-lyase, or a derivative thereof.

95. The test kit of claim 72, wherein said cystathionine β-synthase, or a derivative thereof, cystathionine β-lyase, or a derivative thereof, cystathionine γ-lyase, or a derivative thereof, lactate dehydrogenase, or a derivative thereof, are immobilized within said container.

96. A method for assessing the amount of homocysteine in a sample, comprising the steps of:
 (a) contacting the sample with a reducing agent for a time period sufficient to release reduced homocysteine from a homocysteine binding protein;
 (b) contacting said reduced homocysteine with a homocysteine metabolite binding transcription factor under conditions conducive for complex formation between said reduced homocysteine and said homocysteine metabolite binding transcription factor;
 (c) admixing said sample with a consensus polynucleotide sequence or a derivative thereof specifically recognized by said homocysteine/transcription factor complex or derivative thereof in order to bind said homocysteine/transcription factor complex with said concensus polynucleotide sequence;
 (d) determining the amount of homocysteine/transcription factor complex bound by the concensus polynucleotide sequence; and (e) correlating the amount of homocysteine present in said sample with said determined amount, wherein steps (a)–(c) are completed in less than 15 minutes.

97. The method of claim 96, wherein said reducing agent comprises a borohydride salt or a thiol reducing agent.

98. The method of claim 97, said thiol reducing agent being selected from the group consisting of comprises β-mercaptoethanol, dithiothreitol, dithioerythritol, TCEP, or thioacetic acid, or any salt of each, thereof.

99. The method of claim 96, wherein said homocysteine metabolite binding transcription factor comprises MetR or derivative thereof.

100. The method of claim 96, wherein said consensus polynucleotide sequence comprises the polynucleotide sequence of SEQ ID NO: 11 or derivative thereof.

101. The method of claim 96, wherein said determined amount of homocysteine/transcription factor complex is determined by fluorescence.

102. The method of claim 96, said method being performed on an analyzer adapted to detect said signal.

103. The method of claim 96, said method being performed with one instrument.

104. An assay for assessing the amount of homocysteine in a sample comprising the steps of:
   (a) creating a reaction mixture including said sample, serine, lactate dehydrogenase, NADH and a reductant capable of liberating protein-bound homocysteine in the sample, or their respective derivatives;
   (b) incubating said reaction mixture for a time sufficient to reduce a preponderance of said protein-bound homocysteine;
   (c) adding an enzyme mixture including cystathionine β-synthase and cystathionine β-lyase, or their respective derivatives, and cyclically converting homocysteine to cystathionine and reconverting cystathionine to homocysteine with attendant production of pyruvate; and
   (d) measuring the production of NAD+ or disappearance of NADH over time as a measure of homocysteine in the sample,
   steps (a)–(c) of said assay being performed in less than 15 minutes.

105. The assay of claim 104, wherein said L-serine is added to the reaction mixture to a final concentration of from at least about 1 μM to about 50 mM.

106. The assay of claim 105, wherein said L-serine is added to the reaction mixture to a final concentration of from at least about 10 μM to about 40 mM.

107. The assay of claim 104, wherein said lactate dehydrogenase is added to the reaction mixture to a final concentration of at least about 30 U/l to about 5000 U/l.

108. The assay of claim 104, wherein said lactate dehydrogenase is added to the reaction mixture to a final concentration of at least about 30 U/l to about 3000 U/l.

109. The assay of claim 104, wherein said NADH is added to the reaction mixture to a final concentration of at least about 0.1 mM to about 2 mM.

110. The assay of claim 109, wherein said NADH is added to the reaction mixture to a final concentration of at least about 0.1 mM to about 1.5 mM.

111. The assay of claim 104, said cystathionine β-synthase being present in a final concentration of from about 0.1 to about 100 KU/l.

112. The assay of claim 111, said cystathionine β-synthase being present in a final concentration of from about 0.5 to about 75 KU/l.

113. The assay of claim 104, said cystathionine β-lyase being present in a final concentration of from about 0.01 to about 100 KU/l.

114. The assay of claim 113, said cystathionine β-lyase being present in a final concentration of from about 0.05 to about 50 KU/l.

115. The assay of claim 104, said assay being completed in a period of up to 15 minutes.

116. The assay of claim 115, said assay being completed in a period of from about 5–12 minutes.

117. The assay of claim 104, said reductant being selected from the group consisting of dithiothreitol, dithioerythritol, TCEP, and combinations thereof.

118. The assay of claim 117, said dithiothreitol being present in an amount of from about 0.2 mM to about 3 mM.

119. The assay of claim 118, said dithioerythritol being present in an amount of from about 0.2 mM to about 3 mM.

120. The assay of claim 104, said assay being performed on a clinical chemistry analyzer.

121. The assay of claim 104, said assay being performed in a single instrument.

122. An assay for assessing the amount of homocysteine in a sample comprising the steps of:
   (a) creating a reaction mixture including said sample, serine, cystathionine β-synthase and cystathionine β-lyase, or their respective derivatives, and cyclically converting homocysteine to cystathionine and reconverting cystathionine to homocysteine with attendant production of pyruvate, the ratio of cystathionine β-synthase to cystathionine β-lyase ranging from about 1:1 to 25:1; and
   (b) assessing the amount of pyruvate present in said reaction mixture by adding lactate dehydrogenase and NADH to said reaction mixture and monitoring the production of NAD+ or disappearance of NADH over time in said reaction mixture,
   wherein step (a) is completed in less than 15 minutes.

123. The assay of claim 122, including the step of adding a reductant to the reaction mixture in the presence of said lactate dehydrogenase and NADH in order to reduce at least a portion of any protein-bound homocysteine in the sample.

124. The assay of claim 123, said reductant being selected from the group consisting of dithiothriotol, dithioerythritol, TCEP, and combinations thereof.

125. The assay of claim 124, said dithiothriotol present in an amount of from about 0.2 mM to about 3 mM.

126. The assay of claim 125, said dithioerythritol being present in an amount of from about 0.2 mM to about 3 mM.

127. The assay of claim 122, said assay being carried out in a period of up to about 20 minutes.

128. The assay of claim 127, said assay being carried out in a period of up to about 15 minutes.

129. The assay of claim 122, said assay being performed on a clinical chemistry analyzer.

130. The assay of claim 122, said assay being performed in a single instrument.

131. A method of sequentially assaying a plurality of liquid homocysteine-containing samples comprising the steps of:
   (a) creating a reaction mixture by placing in a container one of said samples together with serine, cystathionine β-synthase, cystationine β-lyase, lactate dehydrogenase, NADH and a reductant capable of liberating protein-bound homocysteine in the sample, or their respective derivatives;
   (b) cyclically converting homocysteine to cystathionine and reconverting cystathionine to homocysteine in said reaction mixture, with attendant production of pyruvate;

(c) assessing the amount of pyruvate present in the reaction mixture by monitoring the production of NAD+ or disappearance of NADH over time therein; and (d) repeating steps (a)–(c) for each of said samples, the time interval between the respective reaction mixture-creation steps for each of said samples being up to about 15 minutes.

132. The method of claim 131, said time interval being up to about 13 minutes.

133. The method of claim 131, including the steps of first creating a first reaction mixture comprising said sample, serine, lactate dehydrogenase, NADH and said reductant, allowing said first reaction mixture to incubate for a period of time to liberate a preponderance of said protein-bound homocysteine, and thereafter adding said cystathionine β-synthase and said cystathionine β-lyase.

134. The method of claim 131, the ratio of cystathionine β-synthase to cystathionine β-lyase in said reaction mixture being from about 1:1 to 25:1.

135. The method of claim 134, said ratio being from about 1:1 to 10:1.

136. The method of claim 131, said method being performed on a clinical chemistry analyzer.

137. The method of claim 131, said method being performed in a single instrument.

138. An isolated enzyme having at least about 80% sequence identity with an enzyme selected from the group consisting of SEQ ID Nos. 19 and 20.

139. An isolated enzyme selected from the group consisting of SEQ ID Nos. 19 and 20.

140. A method of using cystathionine as a homocysteine assay calibrator comprising the steps of:

(a) taking a known concentration of cystathionine;

(b) adding said known concentration to a biological sample;

(c) using said sample containing cystathionine in an enzymatic reaction which converts cystathionine to homocysteine and reconverts homocysteine to cystathionine with the attendant production of pyruvate and ammonia;

(d) measuring the amounts of pyruvate or ammonia produced; and (e) using said measured amounts of pyruvate or ammonia as reference standards for said homocysteine assay, steps (a)–(c) occurring in less than 15 minutes.

141. A process for controlling the overall rate of enzyme reactions that involve homocysteine, wherein homocysteine is not consumed by the enzyme reactions and the steady-state concentration of homocysteine is proportional to the overall rate of such enzyme reactions.

142. A method of using cystathionine as a homocysteine assay calibrator comprising the steps of:

adding cystathionine to a homocysteine assay; and using the results of said assay as a homocysteine calibrator.

* * * * *

SEQUENCE LISTING

```
<160> NUMBER OF SEQ ID NOS: 21

<210> SEQ ID NO 1
<211> LENGTH: 30
<212> TYPE: DNA
<213> ORGANISM: Artificial
<220> FEATURE:
```

```
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 1
cgacggatcc gatggcggac aaaaagcttg                                           30

<210> SEQ ID NO 2
<211> LENGTH: 29
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<223> OTHER INFORMATION: Description of Artificial Sequence: PCR Primer

<400> SEQUENCE: 2
cgcagcagct gttatacaat tcgcgcaaa                                            29

<210> SEQ ID NO 3
<211> LENGTH: 29
<212> TYPE: DNA
<213> ORGANISM: Artificial Sequence
<220> FEATURE:
<223> OTHER INFORMATION: PCR PRimer
<220> FEATURE:
<221> NAME/KEY: misc_feature
<223> OTHER INFORMATION: Description of Artificial Sequence:  PCR Primer

<400> SEQUENCE: 3
cggggatcct gatgcatgca tgataagga                                            29

<210> SEQ ID NO 4
<211> LENGTH: 27
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 4
cggcattacc gtttcactaa tttattg                                              27

<210> SEQ ID NO 5
<211> LENGTH: 25
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 5
gttggatccg gcattaccgt ttcac                                                25

<210> SEQ ID NO 6
<211> LENGTH: 30
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer
```

<400> SEQUENCE: 6
ggtggatcca tcaatagata cgtacgtcct                                30

<210> SEQ ID NO 7
<211> LENGTH: 25
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 7
ttttagttta tgtatgtgtt ttttg                                     25

<210> SEQ ID NO 8
<211> LENGTH: 41
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 8
aacacataca taaactaaaa atgactaaat ctgagcagca a                   41

<210> SEQ ID NO 9
<211> LENGTH: 39
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 9
atgatgatga tgatgatgac ctgctaagta gctcagtaa                      39

<210> SEQ ID NO 10
<211> LENGTH: 36
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 10
catcatcatc atcatcatta aataagaacc cacgct                         36

<210> SEQ ID NO 11
<211> LENGTH: 30
<212> TYPE: DNA
<213> ORGANISM: Artificial
<220> FEATURE:
<223> OTHER INFORMATION: Consensus MetR receptor Sequence
<220> FEATURE:
<221> NAME/KEY: misc_feature
<223> OTHER INFORMATION: Description of Artificial Sequence:  Consensus
      MetR receptor Sequence

<400> SEQUENCE: 11

```
gttaatgttg aacaaatctc atgttgcgtg                                              30
```

<210> SEQ ID NO 12
<211> LENGTH: 35
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence: PCR Primer

<400> SEQUENCE: 12

```
gcgggtcgac tatgactaaa tctgagcagc aagcc                                        35
```

<210> SEQ ID NO 13
<211> LENGTH: 31
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence: PCR Primer

<400> SEQUENCE: 13

```
gcgtgcggcc gcgttatgct aagtagctca g                                            31
```

<210> SEQ ID NO 14
<211> LENGTH: 1524
<212> TYPE: DNA
<213> ORGANISM: Saccharomyces cerevisiae

<400> SEQUENCE: 14

```
atgactaaat ctgagcagca agccgattca agacataacg ttatcgactt agttggtaac             60
acccattga tcgcactgaa aaaattgcct aaggctttgg gtatcaaacc acaaattat              120
gctaagctgg aactatacaa tccaggtggt ccatcaaag acagaattgc caagtctatg             180
gtggaagaag ctgaagcttc cggtagaatt catccttcca gatctactct gatcgaacct            240
acttctggta acaccggtat cggtctagct ttaatcggcg ccatcaaagg ttacagaact            300
atcatcacct tgccggaaaa aatgtctaac gagaaagttt ctgtcctaaa ggctctgggt            360
gctgaaatca tcagaactcc aactgctgct gcctgggatt ctccagaatc acatattggt            420
gttgctaaga agttggaaaa agagattcct ggtgctgtta cttgacca atataacaat              480
atgatgaacc agaagctca ttactttggt actggtcgcg aaatccaaag acagctagaa             540
gacttgaatt tatttgataa tctacgcgct gttgttgctg gtgctggtac tggtgggact            600
attagcggta tttccaagta cttgaaagaa cagaatgata agatccaaat cgttggtgct            660
gagggattcg gttcaatttt agcccaacct gaaaacttga ataagactga tatcactgac            720
tacaaagttg agggtattgg ttatgatttt gttcctcagg ttttggacag aaaattaatt            780
gatgtttggt ataagacaga cgacaagcct tctttcaaat acgccagaca attgatttct            840
aacgaaggtg tcttggtggg tggttcttcc ggttctacct tcactgcggt tgtgaaatac            900
tgtgaagacc accctgaact gactgaagat gatgtcattg ttgccatatt cccagattcc            960
atcaggtcgt acctaaccaa attcgtcgat gacgaatggt tgaaaagaa caatttgtgg            1020
gatgatgacg tgttggcccg ttttgactct tcaaagctgg aggcttcgac gacaaaatac          1080
gctgatgtgt ttggtaacgc tactgtaaag gatcttcact tgaaaccggt tgtttccgtt          1140
aaggaaaccg ctaaggtcac tgatgttatc aagatattaa aagacaatgg ctttgaccaa          1200
```

```
ttgcctgtgt tgactgaaga cggcaagttg tctggtttag ttactctctc tgagcttcta    1260
agaaaactat caatcaataa ttcaaacaac gacaacacta taaagggtaa atacttggac    1320
ttcaagaaat taaacaattt caatgatgtt tcctcttaca acgaaaataa atccggtaag    1380
aagaagttta ttaaattcga tgaaaactca aagctatctg acttgaatcg tttctttgaa    1440
aaaaactcat ctgccgttat cactgatggc ttgaaaccaa tccatatcgt tactaagatg    1500
gatttactga gctacttagc ataa                                           1524
```

<210> SEQ ID NO 15
<211> LENGTH: 43
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 15

```
ctatatcgta ataatgacta aatctgagca gcaagccgat tca                       43
```

<210> SEQ ID NO 16
<211> LENGTH: 40
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 16

```
agggctcgag gatcccgggg gtgctattat gaatgcacgg                           40
```

<210> SEQ ID NO 17
<211> LENGTH: 35
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 17

```
cggggatccg acgttttgcc cgcaggcggg aaacc                                35
```

<210> SEQ ID NO 18
<211> LENGTH: 39
<212> TYPE: DNA
<213> ORGANISM: Artificial
<220> FEATURE:
<223> OTHER INFORMATION: PCR Primer
<220> FEATURE:
<221> NAME/KEY: misc_feature
<223> OTHER INFORMATION: Description of Artificial Sequence:  PCR Primer

<400> SEQUENCE: 18

```
agatttagtc attattacga tatagttaat agttgatag                            39
```

<210> SEQ ID NO 19
<211> LENGTH: 428
<212> TYPE: PRT
<213> ORGANISM: Escherichia coli -continued

```
<400> SEQUENCE: 19

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Asp Lys Lys Leu Asp Thr Gln Leu Val Asn Ala Gly Arg
        35                  40                  45

Ser Lys Lys Tyr Thr Leu Gly Ala Val Asn Ser Val Ile Gln Arg Ala
    50                  55                  60

Ser Ser Leu Val Phe Asp Ser Val Glu Ala Lys Lys His Ala Thr Arg
65                  70                  75                  80

Asn Arg Ala Asn Gly Glu Leu Phe Tyr Gly Arg Arg Gly Thr Leu Thr
                    85                  90                  95

His Phe Ser Leu Gln Gln Ala Met Cys Glu Leu Glu Gly Gly Ala Gly
                100                 105                 110

Cys Val Leu Phe Pro Cys Gly Ala Ala Val Ala Asn Ser Ile Leu
            115                 120                 125

Ala Phe Ile Glu Gln Gly Asp His Val Leu Met Thr Asn Thr Ala Tyr
    130                 135                 140

Glu Pro Ser Gln Asp Phe Cys Ser Lys Ile Leu Ser Lys Leu Gly Val
145                 150                 155                 160

Thr Thr Ser Trp Phe Asp Pro Leu Ile Gly Ala Asp Ile Val Lys His
                165                 170                 175

Leu Gln Pro Asn Thr Lys Ile Val Phe Leu Glu Ser Pro Gly Ser Ile
                180                 185                 190

Thr Met Glu Val His Asp Val Pro Ala Ile Val Ala Ala Val Arg Ser
            195                 200                 205

Val Val Pro Asp Ala Ile Ile Met Ile Asp Asn Thr Trp Ala Ala Gly
210                 215                 220

Val Leu Phe Lys Ala Leu Asp Phe Gly Ile Asp Val Ser Ile Gln Ala
225                 230                 235                 240

Ala Thr Lys Tyr Leu Val Gly His Ser Asp Ala Met Ile Gly Thr Ala
                245                 250                 255

Val Cys Asn Ala Arg Cys Trp Glu Gln Leu Arg Glu Asn Ala Tyr Leu
            260                 265                 270

Met Gly Gln Met Val Asp Ala Asp Thr Ala Tyr Ile Thr Ser Arg Gly
        275                 280                 285

Leu Arg Thr Leu Gly Val Arg Leu Arg Gln His His Glu Ser Ser Leu
290                 295                 300

Lys Val Ala Glu Trp Leu Ala Glu His Pro Gln Val Ala Arg Val Asn
305                 310                 315                 320

His Pro Ala Leu Pro Gly Ser Lys Gly His Glu Phe Trp Lys Arg Asp
                325                 330                 335

Phe Thr Gly Ser Ser Gly Leu Phe Ser Phe Val Leu Lys Lys Lys Leu
            340                 345                 350

Asn Asn Glu Glu Leu Ala Asn Tyr Leu Asp Asn Phe Ser Leu Phe Ser
        355                 360                 365

Met Ala Tyr Ser Trp Gly Gly Tyr Glu Ser Leu Ile Leu Ala Asn Gln
    370                 375                 380

Pro Glu His Ile Ala Ala Ile Arg Pro Gln Gly Glu Ile Asp Phe Ser
385                 390                 395                 400

Gly Thr Leu Ile Arg Leu His Ile Gly Leu Glu Asp Val Asp Asp Leu
                405                 410                 415
```

Ile Ala Asp Leu Asp Ala Gly Phe Ala Arg Ile Val
            420                 425

<210> SEQ ID NO 20
<211> LENGTH: 1252
<212> TYPE: PRT
<213> ORGANISM: Saccharomyces cerevisiae

<400> SEQUENCE: 20

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Pro Gly Ile Pro Gly Ser Thr Met Thr
225                 230                 235                 240

Lys Ser Glu Gln Gln Ala Asp Ser Arg His Asn Val Ile Asp Leu Val
                245                 250                 255

Gly Asn Thr Pro Leu Ile Ala Leu Lys Lys Leu Pro Lys Ala Leu Gly
            260                 265                 270

Ile Lys Pro Gln Ile Tyr Ala Lys Leu Glu Leu Tyr Asn Pro Gly Gly
        275                 280                 285

Ser Ile Lys Asp Arg Ile Ala Lys Ser Met Val Glu Glu Ala Glu Ala
    290                 295                 300

Ser Gly Arg Ile His Pro Ser Arg Ser Thr Leu Ile Glu Pro Thr Ser
305                 310                 315                 320

Gly Asn Thr Gly Ile Gly Leu Ala Leu Ile Gly Ala Ile Lys Gly Tyr
                325                 330                 335

Arg Thr Ile Ile Thr Leu Pro Glu Lys Met Ser Asn Glu Lys Val Ser
            340                 345                 350

Val Leu Lys Ala Leu Gly Ala Glu Ile Ile Arg Thr Pro Thr Ala Ala

```
            355                 360                 365
Ala Trp Asp Ser Pro Glu Ser His Ile Gly Val Ala Lys Lys Leu Glu
    370                 375                 380

Lys Glu Ile Pro Gly Ala Val Ile Leu Asp Gln Tyr Asn Asn Met Met
385                 390                 395                 400

Asn Pro Glu Ala His Tyr Phe Gly Thr Gly Arg Glu Ile Gln Arg Gln
                405                 410                 415

Leu Glu Asp Leu Asn Leu Phe Asp Asn Leu Arg Ala Val Val Ala Gly
            420                 425                 430

Ala Gly Thr Gly Thr Ile Ser Gly Ile Ser Lys Tyr Leu Lys Glu
        435                 440                 445

Gln Asn Asp Lys Ile Gln Ile Val Gly Ala Asp Pro Phe Gly Ser Ile
450                 455                 460

Leu Ala Gln Pro Glu Asn Leu Asn Lys Thr Asp Ile Thr Asp Tyr Lys
465                 470                 475                 480

Val Glu Gly Ile Gly Tyr Asp Phe Val Pro Gln Val Leu Asp Arg Lys
                485                 490                 495

Leu Ile Asp Val Trp Tyr Lys Thr Asp Asp Lys Pro Ser Phe Lys Tyr
            500                 505                 510

Ala Arg Gln Leu Ile Ser Asn Glu Gly Val Leu Val Gly Gly Ser Ser
        515                 520                 525

Gly Ser Ala Phe Thr Ala Val Val Lys Tyr Cys Glu Asp His Pro Glu
530                 535                 540

Leu Thr Glu Asp Asp Val Ile Val Ala Ile Phe Pro Asp Ser Ile Arg
545                 550                 555                 560

Ser Tyr Leu Thr Lys Phe Val Asp Asp Glu Trp Leu Lys Lys Asn Asn
                565                 570                 575

Leu Trp Asp Asp Val Leu Ala Arg Phe Asp Ser Ser Lys Leu Glu
            580                 585                 590

Ala Ser Thr Thr Lys Tyr Ala Asp Val Phe Gly Asn Ala Thr Val Lys
        595                 600                 605

Asp Leu His Leu Lys Pro Val Ser Val Lys Glu Thr Ala Lys Val
610                 615                 620

Thr Asp Val Ile Lys Ile Leu Lys Asp Asn Gly Phe Asp Gln Leu Pro
625                 630                 635                 640

Val Leu Thr Glu Asp Gly Lys Leu Ser Gly Leu Val Thr Leu Ser Glu
                645                 650                 655

Leu Leu Arg Lys Leu Ser Ile Asn Asn Ser Asn Asn Asp Asn Thr Ile
            660                 665                 670

Lys Gly Lys Tyr Leu Asp Phe Lys Lys Leu Asn Asn Phe Asn Asp Val
        675                 680                 685

Ser Ser Tyr Asn Glu Asn Lys Ser Gly Lys Lys Phe Ile Lys Phe
690                 695                 700

Asp Glu Asn Ser Lys Leu Ser Asp Leu Asn Arg Phe Phe Glu Lys Asn
705                 710                 715                 720

Ser Ser Ala Val Ile Thr Asp Gly Leu Lys Pro Ile His Ile Val Thr
                725                 730                 735

Lys Met Asp Leu Leu Ser Tyr Leu Ala Met Thr Lys Ser Glu Gln Gln
            740                 745                 750

Ala Asp Ser Arg His Asn Val Ile Asp Leu Val Gly Asn Thr Pro Leu
        755                 760                 765

Ile Ala Leu Lys Lys Leu Pro Lys Ala Leu Gly Ile Lys Pro Gln Ile
770                 775                 780
```

-continued

Tyr Ala Lys Leu Glu Leu Tyr Asn Pro Gly Gly Ser Ile Lys Asp Arg
785                 790                 795                 800

Ile Ala Lys Ser Met Val Glu Glu Ala Glu Ala Ser Gly Arg Ile His
            805                 810                 815

Pro Ser Arg Ser Thr Leu Ile Glu Pro Thr Ser Gly Asn Thr Gly Ile
        820                 825                 830

Gly Leu Ala Leu Ile Gly Ala Ile Lys Gly Tyr Arg Thr Ile Ile Thr
        835                 840                 845

Leu Pro Glu Lys Met Ser Asn Glu Lys Val Ser Val Leu Lys Ala Leu
    850                 855                 860

Gly Ala Glu Ile Ile Arg Thr Pro Thr Ala Ala Trp Asp Ser Pro
865                 870                 875                 880

Glu Ser His Ile Gly Val Ala Lys Lys Leu Glu Lys Glu Ile Pro Gly
            885                 890                 895

Ala Val Ile Leu Asp Gln Tyr Asn Asn Met Met Asn Pro Glu Ala His
            900                 905                 910

Tyr Phe Gly Thr Gly Arg Glu Ile Gln Arg Gln Leu Glu Asp Leu Asn
        915                 920                 925

Leu Phe Asp Asn Leu Arg Ala Val Val Ala Gly Ala Gly Thr Gly Gly
    930                 935                 940

Thr Ile Ser Gly Ile Ser Lys Tyr Leu Lys Glu Gln Asn Asp Lys Ile
945                 950                 955                 960

Gln Ile Val Gly Ala Asp Pro Phe Gly Ser Ile Leu Ala Gln Pro Glu
            965                 970                 975

Asn Leu Asn Lys Thr Asp Ile Thr Asp Tyr Lys Val Glu Gly Ile Gly
        980                 985                 990

Tyr Asp Phe Val Pro Gln Val Leu  Asp Arg Lys Leu Ile  Asp Val Trp
    995                 1000                1005

Tyr Lys  Thr Asp Asp Lys Pro  Ser Phe Lys Tyr Ala  Arg Gln Leu
    1010                1015                1020

Ile Ser Asn Glu Gly Val Leu  Val Gly Gly Ser Ser  Gly Ser Ala
    1025                1030                1035

Phe Thr  Ala Val Val Lys Tyr  Cys Glu Asp His Pro  Glu Leu Thr
    1040                1045                1050

Glu Asp  Asp Val Ile Val Ala  Ile Phe Pro Asp Ser  Ile Arg Ser
    1055                1060                1065

Tyr Leu  Thr Lys Phe Val Asp  Asp Glu Trp Leu Lys  Lys Asn Asn
    1070                1075                1080

Leu Trp  Asp Asp Asp Val Leu  Ala Arg Phe Asp Ser  Ser Lys Leu
    1085                1090                1095

Glu Ala  Ser Thr Thr Lys Tyr  Ala Asp Val Phe Gly  Asn Ala Thr
    1100                1105                1110

Val Lys  Asp Leu His Leu Lys  Pro Val Val Ser Val  Lys Glu Thr
    1115                1120                1125

Ala Lys  Val Thr Asp Val Ile  Lys Ile Leu Lys Asp  Asn Gly Phe
    1130                1135                1140

Asp Gln  Leu Pro Val Leu Thr  Glu Asp Gly Lys Leu  Ser Gly Leu
    1145                1150                1155

Val Thr  Leu Ser Glu Leu Leu  Arg Lys Leu Ser Ile  Asn Asn Ser
    1160                1165                1170

Asn Asn  Asp Asn Thr Ile Lys  Gly Lys Tyr Leu Asp  Phe Lys Lys
    1175                1180                1185

```
Leu Asn Asn Phe Asn Asp Val Ser Ser Tyr Asn Glu Asn Lys Ser
    1190            1195            1200

Gly Lys Lys Lys Phe Ile Lys Phe Asp Glu Asn Ser Lys Leu Ser
    1205            1210            1215

Asp Leu Asn Arg Phe Phe Glu Lys Asn Ser Ser Ala Val Ile Thr
    1220            1225            1230

Asp Gly Leu Lys Pro Ile His Ile Val Thr Lys Met Asp Leu Leu
    1235            1240            1245

Ser Tyr Leu Ala
    1250

<210> SEQ ID NO 21
<211> LENGTH: 1188
<212> TYPE: DNA
<213> ORGANISM: Escherichia coli

<400> SEQUENCE: 21
atggcggaca aaaagcttga tactcaactg gtgaatgcag gacgcagcaa aaaatacact    60
ctcggcgcgg taaatagcgt gattcagcgc gcttcttcgc tggtctttga cagtgtagaa   120
gccaaaaaac acgcgacacg taatcgcgcc aatggagagt tgttctatgg acggcgcgga   180
acgttaaccc atttctcctt acaacaagcg atgtgtgaac tggaaggtgg cgcaggctgc   240
gtgctatttc cctgcggggc ggcagcggtt gctaattcca ttcttgcttt tatcgaacag   300
ggcgatcatg tgttgatgac caacaccgcc tatgaaccga gtcaggattt ctgtagcaaa   360
atcctcagca aactgggcgt aacgacatca tggtttgatc cgctgattgg tgccgatatc   420
gttaagcatc tgcagccaaa cactaaaatc gtgtttctgg aatcgccagg ctccatcacc   480
atggaagtcc acgacgttcc ggcgattgtt gccgccgtac gcagtgtggt gccggatgcc   540
atcattatga tcgacaacac ctgggcagcc ggtgtgctgt ttaaggcgct ggatttggc    600 atcgatgttt ctattcaagc cgccaccaaa tatctggttg ggcattcaga tgcgatgatt   660
ggcactgccg tgtgcaatgc ccgttgctgg gagcagctac gggaaaatgc ctatctgatg   720
ggccagatgg tcgatgccga taccgcctat ataaccagcc gtggcctgcg cacattaggt   780
gtgcgtttgc gtcaacatca tgaaagcagt ctgaaagtgg ctgaatggct ggcagaacat   840
ccgcaagttg cgcgagttaa ccaccctgct ctgcctggca gtaaaggtca cgaattctgg   900
aaacgagact ttacaggcag cagcgggcta ttttcctttg tgcttaagaa aaaactcaat   960
aatgaagagc tggcgaacta tctggataac ttcagtttat tcagcatggc ctactcgtgg  1020
ggcgggtatg aatcgttgat cctggcaaat caaccagaac atatcgccgc cattcgccca  1080
caaggcgaga tcgattttag cgggaccttg attcgcctgc atattggtct ggaagatgtc  1140
gacgatctga ttgccgatct ggacgccggt tttgcgcgaa ttgtataa              1188
```